United States Patent
Naismith et al.

(10) Patent No.: US 10,647,977 B2
(45) Date of Patent: May 12, 2020

(54) MODIFIED HETEROCYCLASE

(71) Applicants: THE UNIVERSITY COURT OF THE UNIVERSITY OF ABERDEEN, Aberdeen, Aberdeenshire (GB); THE UNIVERSITY COURT OF THE UNIVERSITY OF ST. ANDREWS, St. Andrews, Fife (GB)

(72) Inventors: James Naismith, St. Andrews (GB); Jesko Koehnke, St. Andrews (GB); Andrew Bent, St. Andrews (GB); Nicholas Westwood, St. Andrews (GB); Greg Mann, St. Andrews (GB); Wael Houssen Ibrahim, Aberdeen (GB); Marcel Jaspars, Aberdeen (GB); Ying Ge, St. Andrews (GB)

(73) Assignees: THE UNIVERSITY COURT OF THE UNIVERSITY OF ABERDEEN, Aberdeen (GB); THE UNIVERSITY COURT OF THE UNIVERSITY OF ST. ANDREWS, St. Andrews, Fife (GB)

(*) Notice: Subject to any disclaimer, the term of this patent is extended or adjusted under 35 U.S.C. 154(b) by 218 days.

(21) Appl. No.: 15/524,219

(22) PCT Filed: Nov. 4, 2015

(86) PCT No.: PCT/EP2015/075757
§ 371 (c)(1),
(2) Date: May 3, 2017

(87) PCT Pub. No.: WO2016/071422
PCT Pub. Date: May 12, 2016

(65) Prior Publication Data
US 2018/0245061 A1 Aug. 30, 2018

(30) Foreign Application Priority Data
Nov. 4, 2014 (GB) .................................. 1419650.5

(51) Int. Cl.
| | |
|---|---|
| C12N 9/90 | (2006.01) |
| C07K 1/107 | (2006.01) |
| C12P 21/02 | (2006.01) |
| C12N 9/00 | (2006.01) |

(52) U.S. Cl.
CPC ............... *C12N 9/90* (2013.01); *C07K 1/107* (2013.01); *C12P 21/02* (2013.01); *C12Y 504/99027* (2013.01); *C12N 9/00* (2013.01)

(58) Field of Classification Search
None
See application file for complete search history.

(56) References Cited

FOREIGN PATENT DOCUMENTS

| WO | 2014/136971 | 9/2014 |
| WO | 2014136971 | 9/2014 |

OTHER PUBLICATIONS

Koehnke, Jesko, et al., (2015) "Structural analysis of leader peptide binding enables leader-free cyanobactin processing", Nature Chemical Biology., 11(8):558-563.
Oman, Trent, J., et al., (2012) "An Engineered Lantibiotic Synthetase That Does Not Require a Leader Peptide on Its Substrate", Journal of the American Chemical Society, 134(16):6952-6955.
Koehnke, Jesko, et al., (2013) "The Cyanobactin Heterocyclase Enzyme: A Processive Adenylase That Operates with a Defined Order of Reaction", Angewandte Chemie Internati0nal Edition, 52(52):13991-13996.
Sivonen, Kaarina, et al., (2010) "Cyanobactins-ribosomal cyclic peptides produced by cyanobacteria", Applied Microbiology and Biotechnology, 86(5):1213-1225.
Martins, Joanna and Vasconcelos, Vitor, (2015) "Cyanobactins from Cyanobacteria: Current Genetic and Chemical State of Knowledge", Marine Drugs, 13(11):6910-6946.
Koehnke et al. (2013) "The Cyanobactin Heterocyclase Enzyme: A Processive Adenylase That Operates with a Defined Order of Reaction",Angewandte Chemie Internati0nal Edition, 52: 13991-13996.
Koehnke et al. (2015) "Structural Analysis of Leader Peptide Binding Enables Leader-Free Cyanobactin Processing", Nature Chemical Bio, 11: 558-563.
Martins et al. (2015) "Cyanobactins From Cyanobacteria: Current Genetic and Chemical State of Knowledge", Marine Drugs, 13: 6910-6946.
Oman et al. (2012) "An Engineered Lantibiotic Synthetase That Does Not Require a Leader Peptide on Its Substrate", Journal 0f The American Chemical Society, 134: 6952-6955.
Sivonen et al. (2010) "Cyanobactins-Ribosomal Cyclic PeptidesProduced By Cyanobacteria",Applied Microbiology and Bio, 86: 1213-1225.

*Primary Examiner* — Suzanne M Noakes
(74) *Attorney, Agent, or Firm* — Rudy J. Ng; Carol L. Francis; Bozicevic, Field & Francis LLP

(57) ABSTRACT

This invention relates to an engineered leader-independent heterocyclase (also known as a cyclodehydratase) comprising a defined cyanobactin leader sequence which drives the efficient conversion of heterocyclisable amino acids, such as Ser, Thr and Cys, within a peptide substrate lacking a leader sequence into heterocycles produce a homogenous heterocycle-containing product. This may be useful in biotechnology and chemical synthesis.

17 Claims, 13 Drawing Sheets

Specification includes a Sequence Listing.

Table 1

| | LynD/ATP/PatE'C51A | LynD/AMP/PatE' | LynD/β,γ-imido-ATP/PatE'C51A |
|---|---|---|---|
| Data collection | | | |
| Space group | $P2_12_12_1$ | $P2_12_12_1$ | $P2_12_12_1$ |
| Cell dimensions | | | |
|   $a, b, c$ (Å) | 81.8, 116.2, 183.5 | 65.8, 152.8, 182.8 | 65.9, 152.9, 182.5 |
|   $\alpha, \beta, \gamma$ (°) | 90.00, 90.00, 90.00 | 90.00, 90.00, 90.00 | 90.00, 90.00, 90.00 |
| Resolution (Å) | 2.14 (2.20-2.14)* | 2.86 (2.93-2.86) | 3.01 (3.09-3.01) |
| $R_{sym}$ or $R_{merge}$ | 4.4 (56.9) | 12.4 (89.7) | 12.1 (83.0) |
| $I / \sigma I$ | 19.5 (2.2) | 11.1 (2.0) | 11.4 (2.1) |
| Completeness (%) | 98.8 (98.3) | 97.5 (98.5) | 99.8 (100.0) |
| Redundancy | 3.7 (3.7) | 4.0 (4.0) | 5.4 (5.8) |
| | | | |
| Refinement | | | |
| Resolution (Å) | 47.35-2.14 | 76.41-2.86 | 76.44-3.01 |
| No. reflections | 95,581 | 42,149 | 37,339 |
| $R_{work} / R_{free}$ | 0.198 / 0.244 | 0.201 / 0.251 | 0.211 / 0.266 |
| No. atoms | 12,653 | 11,955 | 12,008 |
|   Protein | 12,008 | 11,930 | 11,940 |
|   Ligand/ion | 72 | 6 | 68 |
|   Water | 573 | 19 | 0 |
| B-factors | 58.80 | 75.20 | 95.50 |
|   Protein | 58.80 | 75.20 | 95.50 |
|   Ligand/ion | 52.80 | 92.40 | 85.90 |
|   Water | 53.10 | 57.00 | |
| R.m.s. deviations | | | |
|   Bond lengths (Å) | 0.007 | 0.005 | 0.005 |
|   Bond angles (°) | 1.071 | 0.913 | 0.971 |

*Number of xtals for each structure should be noted in footnote. *Values in parentheses are for highest-resolution shell.

Figure 11

Table 2

| Enzyme | Nucleotide K$_D$ (µM) | | No. of heterocycles (PatE') |
|---|---|---|---|
| | ATP | AMP | |
| LynD | 50.25 | 14.41 | 2 |
| LynD K409E | no binding | no binding | 2 |
| LynD K409A | no binding | no binding | 1 |
| LynD E423R | no binding | 5.65 | 0 |
| LynD R427E | no binding | 23.04 | 1 and 2 |
| LynD R636E | no binding | no binding | 0, 1 and 2 |
| LynD R636A | N/A | no binding | 0, 1 and 2 |

Figure 12

Table 3

| Enzyme | Peptide | $K_D$ (µM) | No. of heterocycles |
|---|---|---|---|
| LynD | PatE' | 1.49 | 2 |
| LynD | PatE' L26R | no binding | 2 |
| LynD | PatE' L29R | no binding | 1 and 2 |
| LynD | PatE' E31R | no binding | 1 and 2 |
| LynD | PatE' E32R | 18.35 | 2 |
| LynD Y67D | PatE' | 12.92 | 2 |
| LynD Y67D | PatE' L26R | 15.22 | 2 |
| LynD R74E | PatE' | no binding | 2 |
| LynD R74E | PatE' E31R | no binding | 1 and 2 |
| LynD R399E | PatE' | 10.74 | 2 |
| LynD R399E | PatE' E32R | 8.55 | 2 |

Figure 13

Table 4

| LynD | PatE' | | MS (No. of heterocycles) |
|---|---|---|---|
| W.T | PatE' | [1-16]-[LAELSEEAL]-[GLEAS] K [ITA●ITF●] [AYDG] | 2 |
| W.T | PatE'-L26R | [1-16]-[RAELSEEAL]-[GLEAS] K [ITA●ITF●] [AYDG] | 2 |
| W.T | PatE'-L28R | [1-16]-[LAELSEEAL]-[GLEAS] K [ITA○ITF●] [AYDG] | 1 and 2 |
| W.T | PatE'-E31R | [1-16]-[LAELSEEAL]-[GLEAS] K [ITA○ITF●] [AYDG] | 1 and 2 |
| W.T | PatE'-E32R | [1-16]-[LAELSEEAL]-[GLEAS] K [ITA●ITF●] [AYDG] | 2 |
| Y67D | PatE' | [1-16]-[LAELSEEAL]-[GLEAS] K [ITA●ITF●] [AYDG] | 2 |
| Y67D | PatE'-L28R | [1-16]-[LAELSEEAL]-[GLEAS] K [ITA●ITF●] [AYDG] | 2 |
| R74E | PatE' | [1-16]-[LAELSEEAL]-[GLEAS] K [ITA●ITF●] [AYDG] | 2 |
| R74E | PatE'-E31R | [1-16]-[LAELSEEAL]-[GLEAS] K [ITA○ITF●] [AYDG] | 1 and 2 |
| R398E | PatE' | [1-16]-[LAELSEEAL]-[GLEAS] K [ITA●ITF●] [AYDG] | 2 |
| R398E | PatE'-E32R | [1-16]-[LAELSEEAL]-[GLEAS] K [ITA●ITF●] [AYDG] | 2 |
| K409A | PatE' | [1-16]-[LAELSEEAL]-[GLEAS] K [ITA●ITF●] [AYDG] | 2 |
| K409E | PatE' | [1-16]-[LAELSEEAL]-[GLEAS] K [ITA C ITF●] [AYDG] | 1 |
| E423R | PatE' | [1-16]-[LAELSEEAL]-[GLEAS] K [ITAC ITFC] [AYDG] | 0 |
| R427E | PatE' | [1-16]-[LAELSEEAL]-[GLEAS] K [ITA◐ITF●] [AYDG] | 1 and 2 |
| K636A | PatE' | [1-16]-[LAELSEEAL]-[GLEAS] K [ITA C ITF C] [AYDG] | 0, 1 and 2 |
| K636E | PatE' | [1-16]-[LAELSEEAL]-[GLEAS] K [ITA C ITF C] [AYDG] | 0, 1 and 2 |
| I644V | PatE' | [1-16]-[LAELSEEAL]-[GLEAS] K [ITA●ITF●] [AYDG] | 2 |
| F748D | PatE' | [1-16]-[LAELSEEAL]-[GLEAS] K [ITA●ITF●] [AYDG] | 2 |

SEQUENCE LISTING

<160> NUMBER OF SEQ ID NOS: 61

<210> SEQ ID NO 1
<211> LENGTH: 775
<212> TYPE: PRT
<213> ORGANISM: Lyngbya sp. PCC 8106

<400> SEQUENCE: 1

```
Met Gln Ser Thr Pro Leu Leu Gln Ile Gln Pro His Phe His Val Glu
1               5                   10                  15

Val Ile Glu Pro Lys Gln Val Tyr Leu Leu Gly Glu Gln Ala Asn His
            20                  25                  30

Ala Leu Thr Gly Gln Leu Tyr Cys Gln Ile Leu Pro Leu Leu Asn Gly
        35                  40                  45

Gln Tyr Thr Leu Glu Gln Ile Val Glu Lys Leu Asp Gly Glu Val Pro
    50                  55                  60

Pro Glu Tyr Ile Asp Tyr Val Leu Glu Arg Leu Ala Glu Lys Gly Tyr
65                  70                  75                  80

Leu Thr Glu Ala Ala Pro Glu Leu Ser Ser Glu Val Ala Ala Phe Trp
                85                  90                  95

Ser Glu Leu Gly Ile Ala Pro Pro Val Ala Ala Glu Ala Leu Arg Gln
            100                 105                 110

Pro Val Thr Leu Thr Pro Val Gly Asn Ile Ser Glu Val Thr Val Ala
        115                 120                 125

Ala Leu Thr Thr Ala Leu Arg Asp Ile Gly Ile Ser Val Gln Thr Pro
    130                 135                 140

Thr Glu Ala Gly Ser Pro Thr Ala Leu Asn Val Val Leu Thr Asp Asp
145                 150                 155                 160

Tyr Leu Gln Pro Glu Leu Ala Lys Ile Asn Lys Gln Ala Leu Glu Ser
                165                 170                 175

Gln Gln Thr Trp Leu Leu Val Lys Pro Val Gly Ser Val Leu Trp Leu
            180                 185                 190

Gly Pro Val Phe Val Pro Gly Lys Thr Gly Cys Trp Asp Cys Leu Ala
        195                 200                 205

His Arg Leu Arg Gly Asn Arg Glu Val Glu Ala Ser Val Leu Arg Gln
    210                 215                 220

Lys Gln Ala Gln Gln Arg Asn Gly Gln Ser Gly Ser Val Ile Gly
225                 230                 235                 240

Cys Leu Pro Thr Ala Arg Ala Thr Leu Pro Ser Thr Leu Gln Thr Gly
                245                 250                 255

Leu Gln Phe Ala Ala Thr Glu Ile Ala Lys Trp Ile Val Lys Tyr His
            260                 265                 270

Val Asn Ala Thr Ala Pro Gly Thr Val Phe Phe Pro Thr Leu Asp Gly
        275                 280                 285

Lys Ile Ile Thr Leu Asn His Ser Ile Leu Asp Leu Lys Ser His Ile
    290                 295                 300

Leu Ile Lys Arg Ser Gln Cys Pro Thr Cys Gly Asp Pro Lys Ile Leu
305                 310                 315                 320
```

```
Gln His Arg Gly Phe Glu Pro Leu Lys Leu Glu Ser Arg Pro Lys Gln
                    325                 330                 335

Phe Thr Ser Asp Gly Gly His Arg Gly Thr Thr Pro Glu Gln Thr Val
            340                 345                 350

Gln Lys Tyr Gln His Leu Ile Ser Pro Val Thr Gly Val Val Thr Glu
        355                 360                 365

Leu Val Arg Ile Thr Asp Pro Ala Asn Pro Leu Val His Thr Tyr Arg
    370                 375                 380

Ala Gly His Ser Phe Gly Ser Ala Thr Ser Leu Arg Gly Leu Arg Asn
385                 390                 395                 400

Thr Leu Lys His Lys Ser Ser Gly Lys Gly Lys Thr Asp Ser Gln Ser
                405                 410                 415

Lys Ala Ser Gly Leu Cys Glu Ala Val Glu Arg Tyr Ser Gly Ile Phe
            420                 425                 430

Gln Gly Asp Glu Pro Arg Lys Arg Ala Thr Leu Ala Glu Leu Gly Asp
        435                 440                 445

Leu Ala Ile His Pro Glu Gln Cys Leu Cys Phe Ser Asp Gly Gln Tyr
    450                 455                 460

Ala Asn Arg Glu Thr Leu Asn Glu Gln Ala Thr Val Ala His Asp Trp
465                 470                 475                 480

Ile Pro Gln Arg Phe Asp Ala Ser Gln Ala Ile Glu Trp Thr Pro Val
                485                 490                 495

Trp Ser Leu Thr Glu Gln Thr His Lys Tyr Leu Pro Thr Ala Leu Cys
            500                 505                 510

Tyr Tyr His Tyr Pro Leu Pro Pro Glu His Arg Phe Ala Arg Gly Asp
        515                 520                 525

Ser Asn Gly Asn Ala Ala Gly Asn Thr Leu Glu Glu Ala Ile Leu Gln
    530                 535                 540

Gly Phe Met Glu Leu Val Glu Arg Asp Gly Val Ala Leu Trp Trp Tyr
545                 550                 555                 560

Asn Arg Leu Arg Arg Pro Ala Val Asp Leu Gly Ser Phe Asn Glu Pro
                565                 570                 575

Tyr Phe Val Gln Leu Gln Gln Phe Tyr Arg Glu Asn Asp Arg Asp Leu
            580                 585                 590

Trp Val Leu Asp Leu Thr Ala Asp Leu Gly Ile Pro Ala Phe Ala Gly
        595                 600                 605

Val Ser Asn Arg Lys Thr Gly Ser Ser Glu Arg Leu Ile Leu Gly Phe
    610                 615                 620

Gly Ala His Leu Asp Pro Thr Ile Ala Ile Leu Arg Ala Val Thr Glu
625                 630                 635                 640

Val Asn Gln Ile Gly Leu Glu Leu Asp Lys Val Pro Asp Glu Asn Leu
                645                 650                 655

Lys Ser Asp Ala Thr Asp Trp Leu Ile Thr Glu Lys Leu Ala Asp His
            660                 665                 670

Pro Tyr Leu Leu Pro Asp Thr Thr Gln Pro Leu Lys Thr Ala Gln Asp
        675                 680                 685

Tyr Pro Lys Arg Trp Ser Asp Asp Ile Tyr Thr Asp Val Met Thr Cys
    690                 695                 700

Val Asn Ile Ala Gln Ala Gly Leu Glu Thr Leu Val Ile Asp Gln
705                 710                 715                 720

Thr Arg Pro Asp Ile Gly Leu Asn Val Val Lys Val Thr Val Pro Gly
                725                 730                 735

Met Arg His Phe Trp Ser Arg Phe Gly Glu Gly Arg Leu Tyr Asp Val
```

```
                    740                 745                 750
Pro Val Lys Leu Gly Trp Leu Asp Glu Pro Leu Thr Glu Ala Gln Met
            755                 760                 765

Asn Pro Thr Pro Met Pro Phe
    770                 775

<210> SEQ ID NO 2
<211> LENGTH: 784
<212> TYPE: PRT
<213> ORGANISM: Prochloron didemni

<400> SEQUENCE: 2

Met Gln Pro Thr Ala Leu Gln Ile Lys Pro His Phe His Val Glu Ile
1               5                   10                  15

Ile Glu Pro Lys Gln Val Tyr Leu Leu Gly Glu Gln Gly Asn His Ala
            20                  25                  30

Leu Thr Gly Gln Leu Tyr Cys Gln Ile Leu Pro Phe Leu Asn Gly Glu
        35                  40                  45

Tyr Thr Arg Glu Gln Ile Val Glu Lys Leu Asp Gly Gln Val Pro Glu
    50                  55                  60

Glu Tyr Ile Asp Phe Val Leu Ser Arg Leu Val Glu Lys Gly Tyr Leu
65                  70                  75                  80

Thr Glu Val Ala Pro Glu Leu Ser Leu Glu Val Ala Ala Phe Trp Ser
                85                  90                  95

Glu Leu Gly Ile Ala Pro Ser Val Val Ala Glu Gly Leu Lys Gln Pro
            100                 105                 110

Val Thr Val Thr Thr Ala Gly Lys Gly Ile Arg Glu Gly Ile Val Ala
        115                 120                 125

Asn Leu Ala Ala Ala Leu Glu Glu Ala Gly Ile Gln Val Ser Asp Pro
    130                 135                 140

Lys Ala Pro Lys Ala Pro Lys Ala Gly Asp Ser Thr Ala Gln Leu Gln
145                 150                 155                 160

Val Val Leu Thr Asp Asp Tyr Leu Gln Pro Glu Leu Ala Ala Ile Asn
                165                 170                 175

Lys Glu Ala Leu Glu Arg Gln Gln Pro Trp Leu Leu Val Lys Pro Val
            180                 185                 190

Gly Ser Ile Leu Trp Leu Gly Pro Leu Phe Val Pro Gly Glu Thr Gly
        195                 200                 205

Cys Trp His Cys Leu Ala Gln Arg Leu Arg Gly Asn Arg Glu Val Glu
    210                 215                 220

Ala Ser Val Leu Gln Gln Lys Arg Ala Leu Gln Glu Arg Asn Gly Gln
225                 230                 235                 240

Asn Lys Asn Gly Ala Val Ser Cys Leu Pro Thr Ala Arg Ala Thr Leu
                245                 250                 255

Pro Ser Thr Leu Gln Thr Gly Leu Gln Trp Ala Ala Thr Glu Ile Ala
            260                 265                 270

Lys Trp Met Val Lys Arg His Leu Asn Ala Ile Ala Pro Gly Thr Ala
        275                 280                 285

Arg Phe Pro Thr Leu Ala Gly Lys Ile Phe Thr Phe Asn Gln Thr Thr
    290                 295                 300

Leu Glu Leu Lys Ala His Pro Leu Ser Arg Arg Pro Gln Cys Pro Thr
305                 310                 315                 320

Cys Gly Asp Gln Glu Ile Leu Gln Arg Arg Gly Phe Glu Pro Leu Lys
                325                 330                 335
```

```
-continued

Leu Glu Ser Arg Pro Lys His Phe Thr Ser Asp Gly His Arg Ala
                340                 345                 350

Thr Thr Pro Glu Gln Thr Val Gln Lys Tyr Gln His Leu Ile Gly Pro
        355                 360                 365

Ile Thr Gly Val Val Thr Glu Leu Val Arg Ile Ser Asp Pro Ala Asn
    370                 375                 380

Pro Leu Val His Thr Tyr Arg Ala Gly His Ser Phe Gly Ser Ser Ala
385                 390                 395                 400

Gly Ser Leu Arg Gly Leu Arg Asn Thr Leu Arg Tyr Lys Ser Ser Gly
                405                 410                 415

Lys Gly Lys Thr Asp Ser Gln Ser Arg Ala Ser Gly Leu Cys Glu Ala
                420                 425                 430

Ile Glu Arg Tyr Ser Gly Ile Phe Leu Gly Asp Glu Pro Arg Lys Arg
                435                 440                 445

Ala Thr Leu Ala Glu Leu Gly Asp Leu Ala Ile His Pro Glu Gln Cys
        450                 455                 460

Leu His Phe Ser Asp Arg Gln Tyr Asp Asn Arg Asp Ala Leu Asn Ala
465                 470                 475                 480

Glu Gly Ser Ala Ala Ala Tyr Arg Trp Ile Pro His Arg Phe Ala Ala
                485                 490                 495

Ser Gln Ala Ile Asp Trp Thr Pro Leu Trp Ser Leu Thr Glu Gln Lys
                500                 505                 510

His Lys Tyr Val Pro Thr Ala Ile Cys Tyr Tyr Asn Tyr Leu Leu Pro
                515                 520                 525

Pro Ala Asp Arg Phe Cys Lys Ala Asp Ser Asn Gly Asn Ala Ala Gly
        530                 535                 540

Asn Ser Leu Glu Glu Ala Ile Leu Gln Gly Phe Met Glu Leu Val Glu
545                 550                 555                 560

Arg Asp Ser Val Ala Leu Trp Trp Tyr Asn Arg Leu Arg Arg Pro Glu
                565                 570                 575

Val Glu Leu Ser Ser Phe Glu Glu Pro Tyr Phe Leu Gln Leu Gln Gln
                580                 585                 590

Phe Tyr Arg Ser Gln Asn Arg Glu Leu Trp Val Leu Asp Leu Thr Ala
            595                 600                 605

Asp Leu Gly Ile Pro Ala Phe Ala Gly Leu Ser Arg Arg Thr Val Gly
        610                 615                 620

Ser Ser Glu Arg Val Ser Ile Gly Phe Gly Ala His Leu Asp Pro Lys
625                 630                 635                 640

Ile Ala Ile Leu Arg Ala Leu Thr Glu Val Ser Gln Val Gly Leu Glu
                645                 650                 655

Leu Asp Lys Val Pro Asp Glu Lys Leu Asp Gly Glu Ser Lys Asp Trp
                660                 665                 670

Met Leu Glu Val Thr Leu Glu Thr His Pro Cys Leu Ala Pro Asp Pro
        675                 680                 685

Ser Gln Pro Arg Lys Thr Ala Asn Asp Tyr Pro Lys Arg Trp Ser Asp
        690                 695                 700

Asp Ile Tyr Thr Asp Val Met Ala Cys Val Glu Met Ala Lys Val Ala
705                 710                 715                 720

Gly Leu Glu Thr Leu Val Leu Asp Gln Thr Arg Pro Asp Ile Gly Leu
                725                 730                 735

Asn Val Val Lys Val Met Ile Pro Gly Met Arg Thr Phe Trp Ser Arg
                740                 745                 750

Tyr Gly Pro Gly Arg Leu Tyr Asp Val Pro Val Gln Leu Gly Trp Leu
```

```
            755                 760                 765
Lys Glu Pro Leu Ala Glu Ala Glu Met Asn Pro Thr Asn Ile Pro Phe
    770                 775                 780

<210> SEQ ID NO 3
<211> LENGTH: 781
<212> TYPE: PRT
<213> ORGANISM: Prochloron sp. 06037A

<400> SEQUENCE: 3

Met Gln Pro Thr Ala Leu Gln Ile Lys Pro His Phe His Val Glu Ile
1               5                   10                  15

Ile Glu Pro Lys Gln Val Tyr Leu Gly Glu Gln Gly Asn His Ala
            20                  25                  30

Leu Thr Gly Gln Leu Tyr Cys Gln Ile Leu Pro Phe Leu Asn Gly Glu
        35                  40                  45

Tyr Thr Arg Glu Gln Ile Val Glu Lys Leu Asp Gly Gln Val Pro Glu
    50                  55                  60

Glu Tyr Ile Asp Phe Val Leu Ser Arg Leu Val Glu Lys Gly Tyr Leu
65                  70                  75                  80

Thr Glu Val Ala Pro Glu Leu Ser Leu Glu Val Ala Ala Phe Trp Ser
                85                  90                  95

Glu Leu Gly Ile Ala Pro Ser Val Val Ala Glu Gly Leu Lys Gln Pro
            100                 105                 110

Val Thr Val Thr Thr Ala Gly Lys Gly Ile Arg Glu Gly Ile Val Ala
        115                 120                 125

Asn Leu Ala Ala Ala Leu Glu Ala Gly Ile Gln Val Ser Asp Pro
    130                 135                 140

Arg Asp Pro Lys Ala Pro Lys Ala Gly Asp Ser Thr Ala Gln Leu Gln
145                 150                 155                 160

Val Val Leu Thr Asp Asp Tyr Leu Gln Pro Glu Leu Ala Ala Ile Asn
                165                 170                 175

Lys Glu Ala Leu Glu Arg Gln Gln Pro Trp Leu Leu Val Lys Pro Val
            180                 185                 190

Gly Ser Ile Leu Trp Leu Gly Pro Leu Phe Val Pro Gly Glu Thr Gly
        195                 200                 205

Cys Trp His Cys Leu Ala Gln Arg Leu Gln Gly Asn Arg Glu Val Glu
    210                 215                 220

Ala Ser Val Leu Gln Gln Lys Arg Ala Leu Gln Glu Arg Asn Gly Gln
225                 230                 235                 240

Asn Lys Asn Gly Ala Val Ser Cys Leu Pro Thr Ala Arg Ala Thr Leu
                245                 250                 255

Pro Ser Thr Leu Gln Thr Gly Leu Gln Trp Ala Ala Thr Glu Ile Ala
            260                 265                 270

Lys Trp Met Val Lys Arg His Leu Asn Ala Ile Ala Pro Gly Thr Ala
        275                 280                 285

Arg Phe Pro Thr Leu Ala Gly Lys Ile Phe Thr Asn Gln Thr Thr
    290                 295                 300

Leu Glu Leu Lys Ala His Pro Leu Ser Arg Arg Pro Gln Cys Pro Thr
305                 310                 315                 320

Cys Gly Asp Arg Glu Thr Leu Gln Arg Gly Phe Glu Pro Leu Lys
                325                 330                 335

Leu Glu Ser Arg Pro Lys His Phe Thr Ser Asp Gly Gly His Arg Ala
            340                 345                 350
```

```
Met Thr Pro Glu Gln Thr Val Gln Lys Tyr Gln His Leu Ile Gly Pro
            355                 360                 365

Ile Thr Gly Val Val Thr Glu Leu Val Arg Ile Ser Asp Pro Ala Asn
370                 375                 380

Pro Leu Val His Thr Tyr Arg Ala Gly His Ser Phe Gly Ser Ala Thr
385                 390                 395                 400

Ser Leu Arg Gly Leu Arg Asn Val Leu Arg His Lys Ser Ser Gly Lys
                405                 410                 415

Gly Lys Thr Asp Ser Gln Ser Arg Ala Ser Gly Leu Cys Glu Ala Ile
            420                 425                 430

Glu Arg Tyr Ser Gly Ile Phe Gln Gly Asp Glu Pro Arg Lys Arg Ala
        435                 440                 445

Thr Leu Ala Glu Leu Gly Asp Leu Ala Ile His Pro Glu Gln Cys Leu
450                 455                 460

His Phe Ser Asp Arg Gln Tyr Asp Asn Arg Glu Ser Ser Asn Glu Arg
465                 470                 475                 480

Ala Thr Val Thr His Asp Trp Ile Pro Gln Arg Phe Asp Ala Ser Lys
                485                 490                 495

Ala His Asp Trp Thr Pro Val Trp Ser Leu Thr Glu Gln Thr His Lys
            500                 505                 510

Tyr Leu Pro Thr Ala Leu Cys Tyr Arg Tyr Pro Phe Pro Pro Glu
        515                 520                 525

His Arg Phe Cys Arg Ser Ser Asn Gly Asn Ala Ala Gly Asn Thr
    530                 535                 540

Leu Glu Glu Ala Ile Leu Gln Gly Phe Met Glu Leu Val Glu Arg Asp
545                 550                 555                 560

Ser Val Cys Leu Trp Trp Tyr Asn Arg Val Ser Arg Pro Ala Val Asp
                565                 570                 575

Leu Ser Ser Phe Asp Glu Pro Tyr Phe Leu Gln Leu Gln Gln Phe Tyr
            580                 585                 590

Gln Thr Gln Asn Arg Asp Leu Trp Val Leu Asp Leu Thr Ala Asp Leu
        595                 600                 605

Gly Ile Pro Ala Phe Val Gly Val Ser Asn Arg Lys Ala Gly Ser Ser
610                 615                 620

Glu Arg Ile Ile Leu Gly Phe Gly Ala His Leu Asp Pro Thr Val Ala
625                 630                 635                 640

Ile Leu Arg Ala Leu Thr Glu Val Asn Gln Ile Gly Leu Glu Leu Asp
                645                 650                 655

Lys Val Ser Asp Glu Ser Leu Lys Asn Asp Ala Thr Asp Trp Leu Val
            660                 665                 670

Asn Ala Thr Leu Ala Ala Ser Pro Tyr Leu Val Ala Asp Ala Ser Gln
        675                 680                 685

Pro Leu Lys Thr Ala Lys Asp Tyr Pro Arg Arg Trp Ser Asp Asp Ile
690                 695                 700

Tyr Thr Asp Val Met Thr Cys Val Glu Ile Ala Lys Gln Ala Gly Leu
705                 710                 715                 720

Glu Thr Leu Val Leu Asp Gln Thr Arg Pro Asp Ile Gly Leu Asn Val
                725                 730                 735

Val Lys Val Ile Val Pro Gly Met Arg Phe Trp Ser Arg Phe Gly Ser
            740                 745                 750

Gly Arg Leu Tyr Asp Val Pro Val Lys Leu Gly Trp Arg Glu Gln Pro
        755                 760                 765

Leu Ala Glu Ala Gln Met Asn Pro Thr Pro Met Pro Phe
```

```
                    770              775              780
```

<210> SEQ ID NO 4
<211> LENGTH: 776
<212> TYPE: PRT
<213> ORGANISM: Microcystis aeruginosa

<400> SEQUENCE: 4

```
Met Gln Ser Thr Pro Leu Leu Gln Ile Gln Pro His Phe His Val Glu
1               5                   10                  15

Val Ile Glu Pro Lys Gln Val Tyr Leu Leu Gly Glu Gln Ala Asn Tyr
            20                  25                  30

Ala Leu Thr Gly Gln Leu Tyr Cys Gln Ile Leu Pro Leu Leu Asn Gly
        35                  40                  45

Gln His Ser Arg Glu Gln Ile Val Glu Lys Leu Asp Gly Glu Val Pro
    50                  55                  60

Ser Glu Tyr Ile Asp Tyr Val Leu Asp Arg Leu Ala Glu Lys Gly Tyr
65                  70                  75                  80

Leu Thr Glu Ala Ala Pro Glu Leu Ser Ser Glu Val Ala Ala Phe Trp
                85                  90                  95

Ser Glu Leu Gly Ile Ala Pro Val Ala Ala Glu Ala Leu Arg Gln
            100                 105                 110

Pro Val Thr Leu Thr Pro Val Gly Asn Ile Ser Glu Val Thr Val Ala
        115                 120                 125

Ala Leu Thr Thr Ala Leu Arg Asp Ile Gly Ile Ser Val Gln Thr Ser
    130                 135                 140

Thr Glu Ala Val Ser Pro Thr Ala Leu Asn Val Val Leu Thr Asp Asp
145                 150                 155                 160

Tyr Leu Gln Pro Glu Leu Ala Lys Ile Asn Lys Gln Ala Leu Glu Ser
                165                 170                 175

Gln Gln Thr Trp Leu Leu Val Lys Pro Val Gly Ser Val Leu Trp Leu
            180                 185                 190

Gly Pro Val Phe Val Pro Gly Lys Thr Gly Cys Trp Asp Cys Leu Ala
        195                 200                 205

His Arg Leu Arg Gly Asn Arg Glu Val Glu Ala Ser Val Leu Gln Gln
    210                 215                 220

Lys Gln Ala Gln Gln Arg Asn Gly Gln Ser Gly Ser Val Ile Gly
225                 230                 235                 240

Cys Leu Pro Thr Ala Arg Ala Thr Leu Pro Ser Thr Leu Gln Thr Gly
                245                 250                 255

Leu Gln Phe Ala Ala Thr Glu Ile Ala Lys Cys Ile Val Lys His His
            260                 265                 270

Val Asn Ala Thr Ala Pro Gly Thr Val Phe Phe Pro Thr Leu Asp Gly
        275                 280                 285

Lys Ile Ile Thr Leu Asn His Ser Ile Leu Asp Leu Lys Ser His Ile
    290                 295                 300

Leu Ile Lys Arg Ser Gln Cys Ser Thr Cys Gly Asp Arg Gln Ile Leu
305                 310                 315                 320

His Arg Gln Gly Phe Glu Pro Val Lys Leu Val Ser Arg Arg Lys His
                325                 330                 335

Phe Thr His Asp Gly Gly His Arg Ala Phe Thr Pro Glu Gln Thr Val
            340                 345                 350

Gln Lys Tyr Gln His Leu Val Ser Pro Ile Thr Gly Val Val Thr Glu
        355                 360                 365
```

```
Leu Val Arg Leu Thr Asp Pro Ala Asn Pro Leu Val His Thr Tyr Lys
    370                 375                 380

Ala Gly His Ala Phe Gly Ser Ala Thr Thr Leu Arg Gly Leu Arg Asn
385                 390                 395                 400

Thr Leu Lys Tyr Lys Ser Ser Gly Lys Gly Lys Thr Asp Ile Gln Ser
            405                 410                 415

Arg Ala Ser Gly Leu Cys Glu Ala Ile Glu Arg Tyr Ser Gly Ile Phe
                420                 425                 430

Gln Gly Asp Glu Pro Arg Lys Arg Ala Thr Leu Ala Glu Leu Gly Asp
            435                 440                 445

Leu Ala Leu His Pro Glu Ser Leu Leu Tyr Phe Ser Asp Thr Gln Tyr
    450                 455                 460

Ala Asn Arg Glu Glu Leu Asn Ala Gln Gly Ser Ala Ala Tyr Arg
465                 470                 475                 480

Trp Ile Pro Asn Arg Phe Asp Val Ser Gln Ala Ile Asp Trp Thr Pro
                485                 490                 495

Val Trp Ser Leu Thr Glu Gln Lys His Lys Tyr Val Pro Thr Ala Phe
            500                 505                 510

Cys Tyr Tyr Gly Tyr Pro Leu Pro Glu Glu Gln Arg Phe Cys Lys Ala
    515                 520                 525

Asp Ser Asn Gly Asn Ala Ala Gly Asn Thr Leu Glu Ala Ile Leu
530                 535                 540

Gln Gly Phe Leu Glu Leu Val Glu Arg Asp Ser Ile Ala Met Trp Trp
545                 550                 555                 560

Tyr Asn Arg Ile Arg Arg Pro Ala Val Asp Leu Ser Thr Phe Asp Glu
                565                 570                 575

Pro Tyr Phe Val Asp Leu Gln Gln Phe Tyr Gln Gln Asn Arg Glu
            580                 585                 590

Leu Trp Val Leu Asp Val Thr Ala Asp Leu Gly Ile Pro Ala Phe Ala
    595                 600                 605

Gly Phe Ser Arg Arg Thr Val Gly Thr Ser Glu Arg Ile Ser Ile Gly
610                 615                 620

Phe Gly Ala His Leu Asp Pro Thr Ile Ala Ile Leu Arg Ala Leu Thr
625                 630                 635                 640

Glu Val Ser Gln Val Gly Leu Glu Leu Asp Lys Ile Pro Asp Asp Lys
            645                 650                 655

Leu Asp Gly Glu Ser Lys Asp Trp Met Leu Asn Val Thr Val Glu Asn
                660                 665                 670

His Pro Trp Leu Ala Pro Asp Pro Ser Val Pro Met Lys Thr Ala Ser
            675                 680                 685

Asp Tyr Pro Lys Arg Trp Ser Asp Ile His Thr Asp Val Met Asn
690                 695                 700

Cys Val Lys Thr Ala Gln Thr Ala Gly Leu Glu Val Met Val Leu Asp
705                 710                 715                 720

Gln Thr Arg Pro Asp Ile Gly Leu Asn Val Val Lys Val Ile Pro
            725                 730                 735

Gly Met Arg Thr Phe Trp Thr Arg Phe Gly Gln Gly Arg Leu Tyr Asp
                740                 745                 750

Ile Pro Val Lys Leu Gly Trp Leu Asp Ala Pro Leu Ala Glu Glu Glu
            755                 760                 765

Leu Asn Gln Thr Asn Ile Pro Phe
    770                 775
```

```
<210> SEQ ID NO 5
<211> LENGTH: 777
<212> TYPE: PRT
<213> ORGANISM: Nostoc spongiaeforme

<400> SEQUENCE: 5

Met Gln Ser Thr Thr Leu Leu Gln Ile Lys Pro His Phe His Ile Glu
 1               5                  10                  15

Val Ile Glu Pro Lys Gln Val Tyr Leu Leu Gly Glu Gln Gly Asn His
            20                  25                  30

Ala Leu Thr Gly Glu Leu Tyr Cys Gln Ile Val Pro Leu Leu Asp Gly
        35                  40                  45

Gln His Thr Ile Glu Gln Ile Ile Gln Lys Leu Asp Gly Gln Val Pro
    50                  55                  60

Ala Glu Tyr Ile Asp Tyr Val Leu Asn Arg Leu Ala Glu Lys Gly Tyr
65                  70                  75                  80

Leu Thr Glu Ala Thr Pro Asp Leu Ser Pro Glu Val Ala Ala Phe Trp
                85                  90                  95

Thr Glu Leu Gly Ile Ala Pro Thr Val Ala Ala Gln Gly Leu Lys Gln
            100                 105                 110

Pro Val Thr Leu Thr Thr Val Gly Glu Asn Ile Ser Glu Val Thr Val
        115                 120                 125

Ala Ala Leu Ala Thr Ala Leu Arg Asp Met Gly Ile Pro Val Gln Asn
    130                 135                 140

Ala Ser Asp Ile Gly Ser Ser Ala Ala Leu Asn Ile Val Leu Thr Asp
145                 150                 155                 160

Asp Tyr Leu Gln Pro Glu Leu Ala Ala Ile Asn Lys Gln Ala Leu Gln
                165                 170                 175

Ser Gln Gln Thr Trp Leu Leu Val Lys Pro Val Gly Ser Val Leu Trp
            180                 185                 190

Leu Gly Pro Val Phe Val Pro Gln Lys Thr Gly Cys Trp Ser Cys Leu
        195                 200                 205

Ala His Arg Leu Arg Gly Asn Arg Glu Val Glu Ser Ser Val Leu Arg
    210                 215                 220

Gln Lys Gln Ala Gln Glu Arg Asn Gly Gln Gln Gly Arg Val Val
225                 230                 235                 240

Ser Ser Leu Pro Thr Ala Arg Ala Thr Leu Pro Ser Thr Leu Gln Thr
                245                 250                 255

Ala Leu Gln Phe Ala Ala Thr Glu Ile Ala Lys Trp Ile Val Lys Gln
            260                 265                 270

Tyr Val Asn Ala Thr Ala Pro Gly Thr Ala Leu Phe Pro Thr Leu Asp
        275                 280                 285

Gly Lys Val Ile Thr Phe Asn Gln Thr Ile Leu Asp Leu Lys Ser His
    290                 295                 300

Leu Leu Ile Lys Arg Pro Gln Cys Pro Thr Cys Gly Asp Pro Glu Ile
305                 310                 315                 320

Met Gln Arg Arg Gly Phe Glu Pro Leu Lys Leu Glu Ser Arg Arg Lys
                325                 330                 335

Arg Phe Thr His Asp Gly Gly His Arg Ala Thr Thr Pro Glu Gln Thr
            340                 345                 350

Leu Gln Lys Tyr Gln His Leu Ile Gly Pro Val Thr Gly Val Val Thr
        355                 360                 365

Glu Leu Val Arg Ile Thr Asp Pro Ala Asn Pro Leu Val His Thr Tyr
    370                 375                 380
```

-continued

```
Arg Ala Gly His Ser Phe Gly Ser Ala Thr Ser Leu Arg Gly Leu Arg
385                 390                 395                 400

Asn Thr Leu Arg His Lys Ser Ser Gly Lys Gly Lys Thr Asp Ser Gln
            405                 410                 415

Ser Arg Ala Ser Gly Phe Cys Glu Ala Val Glu Arg Tyr Ser Gly Ile
        420                 425                 430

Phe Gln Gly Asp Glu Pro Arg Lys Arg Ala Thr Phe Ala Glu Leu Ala
    435                 440                 445

Asp Leu Ala Ile His Pro Ala Gln Cys Leu His Phe Ser Asp Glu Gln
450                 455                 460

Tyr Thr Asn Arg Glu Ala Leu Asn Ala Gln Gly Thr Glu Ala Ala Tyr
465                 470                 475                 480

Arg Trp Ile Pro His Arg Phe Asp Ala Ser Gln Ala Ile Asp Trp Thr
                485                 490                 495

Pro Val Trp Ser Leu Thr Glu Gln Arg His Lys Tyr Leu Pro Thr Gly
            500                 505                 510

Leu Cys Tyr Tyr His Tyr Pro Met Pro Glu Ala Asn Arg Phe Cys Lys
        515                 520                 525

Ala Asp Ser Asn Gly Asn Ala Ala Gly Asn Thr Leu Glu Glu Ala Ile
    530                 535                 540

Leu Gln Gly Phe Met Glu Leu Glu Arg Asp Ser Val Ala Leu Trp
545                 550                 555                 560

Trp Tyr Asn Arg Leu Ser Arg Pro Gly Val Asp Leu Thr Ser Phe Asn
                565                 570                 575

Glu Pro Tyr Phe Val Gln Leu Gln Gln Phe Tyr Arg Glu Gln Asn Arg
            580                 585                 590

Glu Leu Trp Val Leu Asp Leu Thr Ala Asp Phe Gly Ile Pro Ala Phe
        595                 600                 605

Val Gly Val Ser Tyr Arg Thr Val Gly Thr Ser Glu Arg Ile Ile Val
    610                 615                 620

Gly Phe Gly Ala His Leu Asp Pro Thr Ile Gly Ile Leu Arg Thr Leu
625                 630                 635                 640

Thr Glu Val Ser Gln Ile Gly Leu Glu Leu Asp Lys Ile Pro Asp Glu
                645                 650                 655

Gln Leu Lys Asp Glu Ser Lys Asp Trp Leu Leu Gly Val Thr Arg Glu
            660                 665                 670

Ser His Pro Cys Leu Val Pro Asp Pro Ser Gln Pro Leu Lys Thr Ala
        675                 680                 685

Asn Asp Tyr Pro Lys Arg Trp Ser Asp Ile Tyr Thr Asp Val Met
    690                 695                 700

Thr Cys Val Lys Ile Ala Gln Gly Ile Gly Leu Glu Thr Leu Val Leu
705                 710                 715                 720

Asp Gln Thr Arg Pro Asp Ile Gly Leu Asn Val Val Lys Val Ile Ile
                725                 730                 735

Pro Gly Thr Arg Gly Leu Trp Ser Arg Phe Gly Pro Gly Arg Leu Tyr
            740                 745                 750

Asp Val Pro Val Lys Leu Gly Trp Arg Thr Val Pro Leu Val Glu Ala
        755                 760                 765

Glu Met Asn Pro Met Asn Ile Pro Phe
    770                 775

<210> SEQ ID NO 6
<211> LENGTH: 320
<212> TYPE: PRT
```

<213> ORGANISM: Bacillus thuringiensis

<400> SEQUENCE: 6

Met Met Lys Asn Glu Val Leu Asn Tyr Lys Pro Ile Ile Asp Ser Tyr
1 5 10 15

Cys Phe Val Lys Glu Asp Asp Glu Gly Leu Thr Phe Phe Asn Arg Asp
20 25 30

Thr Tyr Ile Asn Phe His Gly Gly Ser Val Glu Asp Ile Phe Ala Leu
35 40 45

Ile Pro Leu Leu Thr Gly Lys Leu Ser Thr Glu Gln Leu Ala Glu Lys
50 55 60

Leu Glu Leu Pro Ile Glu Tyr Met Cys Asp Ile Ile Lys Leu Leu Asp
65 70 75 80

Glu Lys Asn Ile Ile Lys Asn Tyr Asp Leu Gln Glu Lys Tyr Lys Phe
85 90 95

Met Asp Lys Glu Leu Gln Arg Tyr Glu Arg Phe Ile Ser Asn Leu Thr
100 105 110

Gly Ser Leu Ser Ser Ala Phe Glu Gly Ile Glu Ala Ile Tyr Thr Lys
115 120 125

Lys Ile Val Leu Met Gly Asn Glu Glu Leu Gln Glu Ser Val Arg Lys
130 135 140

Ala Cys Gly Thr Lys Phe Ser Phe Leu Glu Met Ser Gln Ile Gln Asn
145 150 155 160

Ala Ser Leu Ile Ile Ala Val Asp Phe Cys Glu Asn Glu Asn Leu Phe
165 170 175

Ser Glu Ala Asn Glu Leu Ser Lys Cys Tyr Lys Val Pro Phe Leu Arg
180 185 190

Gly Val Val Gln Glu Gln Tyr Phe Ser Ile Gly Pro Ile Phe Ile Ser
195 200 205

Asn Glu Thr Gly Cys Tyr Asn Cys Phe Leu Ser Arg Lys Ile Thr Asn
210 215 220

Tyr Glu Asn Ser Tyr Leu Ser Tyr Lys Tyr Met Lys Lys Tyr Asn Ser
225 230 235 240

Glu Trp Asn Glu Thr His Val Gly Val Ile Pro Gly Thr Ile Glu Met
245 250 255

Leu Ser Phe Asn Ile Leu Ser Phe Ile Met Lys Tyr Phe Ser Asp Cys
260 265 270

Met Pro Cys Glu Ile Ile Gly Lys Glu Phe Thr Tyr Asn Val Phe Asn
275 280 285

Leu Ser Ser Asn Leu Asn Pro Val Leu Lys Val Pro Gly Cys Ser Ile
290 295 300

Cys Ala Gly Ala Asn Lys Asn Ile Met Lys Asp Phe Val Leu Asn Ser
305 310 315 320

<210> SEQ ID NO 7
<211> LENGTH: 319
<212> TYPE: PRT
<213> ORGANISM: Bacillus cereus

<400> SEQUENCE: 7

Met Lys Asn Glu Val Leu Asn Tyr Lys Pro Ile Ile Asp Ser Tyr Cys
1 5 10 15

Phe Val Lys Glu Asp Asp Glu Gly Leu Thr Phe Phe Asn Arg Asp Thr
20 25 30

Tyr Ile Asn Phe His Gly Gly Ser Val Glu Asp Ile Phe Ala Leu Ile

```
            35                  40                  45
Pro Leu Leu Thr Gly Lys Leu Ser Thr Glu Gln Leu Ala Glu Lys Leu
         50                  55                  60

Glu Leu Pro Ile Glu Tyr Met Cys Asp Ile Ile Lys Leu Leu Asp Glu
 65                  70                  75                  80

Lys Asn Ile Ile Lys Asn Tyr Asp Leu Gln Glu Lys Tyr Lys Phe Met
                 85                  90                  95

Asp Lys Glu Leu Gln Arg Tyr Glu Arg Phe Ile Ser Asn Leu Thr Gly
            100                 105                 110

Ser Leu Ser Ser Ala Phe Glu Gly Ile Glu Ala Ile Tyr Thr Lys Lys
        115                 120                 125

Ile Val Leu Met Gly Asn Glu Glu Leu Gln Glu Ser Val Arg Lys Ala
    130                 135                 140

Cys Gly Thr Lys Phe Ser Phe Leu Glu Met Ser Gln Ile Gln Asn Ala
145                 150                 155                 160

Ser Leu Ile Ile Ala Val Asp Phe Cys Glu Asn Glu Asn Leu Phe Ser
                165                 170                 175

Glu Ala Asn Glu Leu Ser Lys Cys Tyr Lys Val Pro Phe Leu Arg Gly
            180                 185                 190

Val Val Gln Glu Gln Tyr Phe Ser Ile Gly Pro Ile Phe Ile Ser Asn
        195                 200                 205

Glu Thr Gly Cys Tyr Asn Cys Phe Leu Ser Arg Lys Ile Thr Asn Tyr
    210                 215                 220

Glu Asn Ser Tyr Leu Ser Tyr Lys Tyr Met Lys Lys Tyr Asn Ser Glu
225                 230                 235                 240

Trp Asn Glu Thr His Val Gly Val Ile Pro Gly Thr Ile Glu Met Leu
                245                 250                 255

Ser Phe Asn Ile Leu Ser Phe Ile Met Lys Tyr Phe Ser Asp Cys Met
            260                 265                 270

Pro Cys Glu Ile Ile Gly Lys Glu Phe Thr Tyr Asn Val Phe Asn Leu
        275                 280                 285

Ser Ser Asn Leu Asn Pro Val Leu Lys Val Pro Gly Cys Ser Ile Cys
    290                 295                 300

Ala Gly Ala Asn Lys Asn Ile Met Lys Asp Phe Val Leu Asn Ser
305                 310                 315

<210> SEQ ID NO 8
<211> LENGTH: 429
<212> TYPE: PRT
<213> ORGANISM: Bacillus thuringiensis

<400> SEQUENCE: 8

Met Gly Ile Gln Asn Ala Leu Glu Tyr Ile Ile Asn Lys Asn Thr Gly
 1               5                  10                  15

Ile Ile His His Val Lys Asn Glu Met Asn Phe Lys Leu Leu Phe Pro
             20                  25                  30

Met His Ile Tyr Phe Thr Phe Arg Asn Glu Leu Val Asp Val Asn Glu
         35                  40                  45

Gly Ile Lys Ile Arg Gly Asn Tyr Ser Gly Leu Gly Tyr Ser Tyr Asp
     50                  55                  60

Ser Ala Glu Ser Ala Leu Ile Ser Ala Val Gly Glu Ile Leu Glu Arg
 65                  70                  75                  80

Tyr Cys Ser Cys Tyr Leu Asn Thr Glu Ala Leu Ile Lys Asn Ser Tyr
                 85                  90                  95
```

```
Asn Ser Leu Val Lys Ser Asn Val Tyr Ala Leu Asn Pro Leu Ser Ile
             100                 105                 110

Thr Gln Pro Leu Arg Glu Gln Tyr Gln Glu Thr Tyr Gly Ile Ser Lys
         115                 120                 125

Glu Ile Asp Gly Asp Thr Ile Phe Asn Trp Val Gln Ala Lys Asp Glu
     130                 135                 140

Ile Tyr Lys Lys Asn Val Leu Val Pro Ala Asn Thr Ile Tyr Phe Asp
145                 150                 155                 160

Val Asp Glu Glu Phe Leu Leu Pro His Ile Arg Asp Ser Ile Ser Thr
                 165                 170                 175

Gly Leu Ala Thr Gly Ser Thr Arg Leu Gln Ala Ile Glu Asn Ala Ala
             180                 185                 190

Leu Glu Cys Ile Glu Arg Asp Ala Ile Met Ile Thr Trp Leu Asn Glu
         195                 200                 205

Leu Ser Val Pro Leu Ile Asp Ser Gln Thr Ile Pro Asp Glu Thr Ile
     210                 215                 220

Gln Tyr Tyr Leu Lys Val Ala Asp Glu Lys Gly Phe Glu Val Phe Phe
225                 230                 235                 240

Phe Asp Ile Thr Thr Asp Ile Lys Val Pro Thr Tyr Phe Val Leu Val
                 245                 250                 255

Arg Asn Leu Tyr Asn Lys Tyr Pro His Ile Gln Ile Gly Ala Lys Ala
             260                 265                 270

His Tyr Asp Pro Leu Ile Ala Leu Lys Gly Ala Leu Met Glu Thr Leu
         275                 280                 285

Ala Ser Leu Asn Leu Leu Ala Asp Pro Asn Asn Lys Thr Thr Glu Ala
     290                 295                 300

Val Asp Ile Lys Asp Thr Ile Asn Ile Lys Ser Ile Lys Asp His Met
305                 310                 315                 320

His Tyr Tyr Ala Ser Gly Asn Thr Lys Glu Ala Phe Asp Phe Leu Ile
                 325                 330                 335

Ser Ser Ser Pro Arg Pro Phe Asn Asn Tyr Ser Glu Ile Asn Asn Phe
             340                 345                 350

Glu Glu Leu Lys Val Lys Leu Asn Thr Met Asn Leu Asn Leu Tyr Thr
         355                 360                 365

Tyr Asp Leu Thr Thr Glu Asp Ile Ser Ser Leu Gly Leu Tyr Val Tyr
     370                 375                 380

Arg Val Leu Met Pro Glu Leu Ala Phe Leu Glu Ile Thr Leu Pro Met
385                 390                 395                 400

Leu Ser Cys Asn Arg Leu Leu Asp Ala Pro Lys Asn Met Gly Tyr Ala
                 405                 410                 415

Pro Ala Lys Ala Phe Asn Lys Asn Pro His Pro Phe Pro
             420                 425

<210> SEQ ID NO 9
<211> LENGTH: 429
<212> TYPE: PRT
<213> ORGANISM: B

```
Gly Val Lys Ile Arg Gly Asp Tyr Gly Gly Leu Gly Tyr Ser Tyr Asp
 50                  55                  60

Ser Ala Glu Ser Ala Leu Ile Ser Ala Val Gly Glu Ile Leu Glu Arg
 65                  70                  75                  80

Tyr Cys Ser Cys Tyr Ile Asn Thr Glu Asn Leu Ile Asn Cys Ser Phe
                 85                  90                  95

Asn Ser Leu Val Lys Glu Asn Val His Ala Leu Asn Pro Leu Ser Ile
            100                 105                 110

Thr Gln Pro Leu Arg Glu Gln His Gln Glu Ile Tyr Gly Asn Ser Lys
        115                 120                 125

Gly Ile Asp Gly Asp Thr Thr Phe Asn Trp Ile Gln Ala Lys Asp Glu
130                 135                 140

Ile His Lys Lys Asn Ile Leu Val Pro Ala Asn Thr Ile Tyr Phe Asp
145                 150                 155                 160

Val Glu Glu Glu Phe Leu Leu Pro Gln Ile Arg Asp Ser Ile Ser Thr
                165                 170                 175

Gly Leu Ala Thr Gly Ser Ser Arg Leu Gln Ala Ile Glu Asn Ala Ala
            180                 185                 190

Leu Glu Cys Ile Glu Arg Asp Ala Ile Met Ile Thr Trp Leu Asn Gln
        195                 200                 205

Leu Ser Val Pro Leu Ile Asp Pro Glu Thr Val Pro Asp Glu Met Val
210                 215                 220

Gln Tyr Tyr Leu Lys Val Ala Gly Glu Lys Gly Phe Glu Val Leu Phe
225                 230                 235                 240

Phe Asp Ile Thr Thr Asp Ile Lys Ile Pro Thr Cys Phe Val Met Val
                245                 250                 255

Arg Asn Leu Tyr Asn Asn Tyr Pro Tyr Ile Gln Val Gly Ala Lys Ala
            260                 265                 270

His Tyr Asn Pro Leu Thr Ala Leu Lys Gly Ala Leu Met Glu Thr Leu
        275                 280                 285

Ala Ser Leu Asn Leu Leu Val Asn Pro Asn Asn Glu Ile Ala Glu Ala
290                 295                 300

Val Asp Ile Lys Asn Thr Gln Ser Ile Lys Ser Ile Lys Asp His Met
305                 310                 315                 320

Leu Tyr Tyr Ala Ser Gly Asn Asp Lys Asp Ala Phe Asp Phe Leu Thr
                325                 330                 335

Ser Ser Ser Pro Lys Pro Phe Ser Tyr Tyr Ser Glu Ile Asn Asn Phe
            340                 345                 350

Glu Glu Leu Lys Val Lys Leu Asn Ala Met Asp Leu Asn Leu Tyr Thr
        355                 360                 365

Tyr Asp Leu Thr Thr Glu Asp Ile Ser Ser Leu Gly Leu Tyr Val Tyr
370                 375                 380

Arg Val Leu Met Pro Glu Leu Ala Phe Leu Glu Ile Thr Leu Pro Met
385                 390                 395                 400

Leu Ser Cys Asn Arg Leu Leu Asp Ala Pro Lys Asn Met Gly Tyr Thr
                405                 410                 415

Pro Ala Lys Thr Phe Asn Lys Asn Pro His Pro Phe Pro
            420                 425

<210> SEQ ID NO 10
<211> LENGTH: 23
<212> TYPE: PRT
<213> ORGANISM: Artificial sequence
<220> FEATURE:
```

```
<223> OTHER INFORMATION: Preferred heterocyclase sequence for use in a
      modified heterocyclase
<220> FEATURE:
<221> NAME/KEY: VARIANT
<222> LOCATION: (4)..(4)
<223> OTHER INFORMATION: Xaa is  Asn or Thr
<220> FEATURE:
<221> NAME/KEY: VARIANT
<222> LOCATION: (5)..(5)
<223> OTHER INFORMATION: Xaa is Thr, Cys or Ser
<220> FEATURE:
<221> NAME/KEY: VARIANT
<222> LOCATION: (6)..(6)
<223> OTHER INFORMATION: Xaa is Leu or Ile
<220> FEATURE:
<221> NAME/KEY: VARIANT
<222> LOCATION: (6)..(6)
<223> OTHER INFORMATION: Xaa is Phe, Leu, Ile or Met
<220> FEATURE:
<221> NAME/KEY: VARIANT
<222> LOCATION: (8)..(8)
<223> OTHER INFORMATION: Xaa is Glu or Asp
<220> FEATURE:
<221> NAME/KEY: VARIANT
<222> LOCATION: (10)..(10)
<223> OTHER INFORMATION: Xaa is Ile or Val
<220> FEATURE:
<221> NAME/KEY: VARIANT
<222> LOCATION: (14)..(14)
<223> OTHER INFORMATION: Xaa is Phe or Leu
<220> FEATURE:
<221> NAME/KEY: VARIANT
<222> LOCATION: (15)..(15)
<223> OTHER INFORMATION: Xaa is Met, Leu or Phe
<220> FEATURE:
<221> NAME/KEY: VARIANT
<222> LOCATION: (17)..(17)
<223> OTHER INFORMATION: Xaa is Leu or Val
<220> FEATURE:
<221> NAME/KEY: VARIANT
<222> LOCATION: (18)..(18)
<223> OTHER INFORMATION: Xaa is Val or Ile
<220> FEATURE:
<221> NAME/KEY: VARIANT
<222> LOCATION: (22)..(22)
<223> OTHER INFORMATION: Xaa is Ser, Ala, or Cys
<220> FEATURE:
<221> NAME/KEY: VARIANT
<222> LOCATION: (23)..(23)
<223> OTHER INFORMATION: Xaa is Val or Ile

<400> SEQUENCE: 10

Ala Ala Gly Xaa Xaa Xaa Glu Xaa Ala Xaa Leu Gln Gly Xaa Xaa Glu
1               5                   10                  15

Xaa Xaa Glu Arg Asp Xaa Xaa
            20

<210> SEQ ID NO 11
<211> LENGTH: 23
<212> TYPE: PRT
<213> ORGANISM: Prochloron sp. 06037A

<400> SEQUENCE: 11

Ala Ala Gly Asn Thr Leu Glu Glu Ala Ile Leu Gln Gly Phe Met Glu
1               5                   10                  15

Leu Val Glu Arg Asp Ser Val
            20

<210> SEQ ID NO 12
<211> LENGTH: 19
<212> TYPE: PRT
<213> ORGANISM: Artificial sequence
<220> FEATURE:
```

```
<223> OTHER INFORMATION: Preferred heterocyclase sequence for use in a
      modified heterocyclase
<220> FEATURE:
<221> NAME/KEY: VARIANT
<222> LOCATION: (1)..(1)
<223> OTHER INFORMATION: Xaa is Ala, Val or Met
<220> FEATURE:
<221> NAME/KEY: VARIANT
<222> LOCATION: (3)..(3)
<223> OTHER INFORMATION: Xaa is Gly or Ala
<220> FEATURE:
<221> NAME/KEY: VARIANT
<222> LOCATION: (4)..(4)
<223> OTHER INFORMATION: Xaa is Leu or Ile
<220> FEATURE:
<221> NAME/KEY: VARIANT
<222> LOCATION: (4)..(4)
<223> OTHER INFORMATION: Xaa is Leu, Val or Phe
<220> FEATURE:
<221> NAME/KEY: VARIANT
<222> LOCATION: (5)..(5)
<223> OTHER INFORMATION: Xaa is Cys or Gly
<220> FEATURE:
<221> NAME/KEY: VARIANT
<222> LOCATION: (7)..(7)
<223> OTHER INFORMATION: Xaa is Ala or Ser
<220> FEATURE:
<221> NAME/KEY: VARIANT
<222> LOCATION: (8)..(8)
<223> OTHER INFORMATION: Xaa is Ile, Val or Leu
<220> FEATURE:
<221> NAME/KEY: VARIANT
<222> LOCATION: (12)..(12)
<223> OTHER INFORMATION: Xaa is Ser or Ala
<220> FEATURE:
<221> NAME/KEY: VARIANT
<222> LOCATION: (13)..(13)
<223> OTHER INFORMATION: Xaa is  Gly or Phe
<220> FEATURE:
<221> NAME/KEY: VARIANT
<222> LOCATION: (14)..(14)
<223> OTHER INFORMATION: Xaa is Ile, Leu, Thr or Val
<220> FEATURE:
<221> NAME/KEY: VARIANT
<222> LOCATION: (15)..(15)
<223> OTHER INFORMATION: Xaa is Phe or Tyr
<220> FEATURE:
<221> NAME/KEY: VARIANT
<222> LOCATION: (16)..(16)
<223> OTHER INFORMATION: Xaa is Gln, Glu,Thr or Leu
<220> FEATURE:
<221> NAME/KEY: VARIANT
<222> LOCATION: (18)..(18)
<223> OTHER INFORMATION: Xaa is Asp, Tyr, Glu or Asn

<400> SEQUENCE: 12

Xaa Ser Xaa Xaa Xaa Glu Xaa Xaa Glu Arg Tyr Xaa Xaa Xaa Xaa Xaa
1               5                   10                  15

Gly Xaa Glu

<210> SEQ ID NO 13
<211> LENGTH: 19
<212> TYPE: PRT
<213> ORGANISM: Prochloron sp. 06037A

<400> SEQUENCE: 13

Ala Ser Gly Leu Cys Glu Ala Ile Glu Arg Tyr Ser Gly Ile Phe Gln
1               5                   10                  15

Gly Asp Glu

<210> SEQ ID NO 14
<211> LENGTH: 9
<212> TYPE: PRT
```

```
<213> ORGANISM: Artificial sequence
<220> FEATURE:
<223> OTHER INFORMATION: Cyanobactin leader sequence
<220> FEATURE:
<221> NAME/KEY: VARIANT
<222> LOCATION: (5)..(5)
<223> OTHER INFORMATION: Xaa is Ser or Thr, preferably Ser
<220> FEATURE:
<221> NAME/KEY: VARIANT
<222> LOCATION: (8)..(8)
<223> OTHER INFORMATION: Xaa is Ala, Val, Thr or Asn
<220> FEATURE:
<221> NAME/KEY: VARIANT
<222> LOCATION: (9)..(9)
<223> OTHER INFORMATION: Xaa is Leu or Ile

<400> SEQUENCE: 14

Leu Ala Glu Leu Xaa Glu Glu Xaa Xaa
1               5

<210> SEQ ID NO 15
<211> LENGTH: 9
<212> TYPE: PRT
<213> ORGANISM: Prochloron sp. 06037A

<400> SEQUENCE: 15

Leu Ala Glu Leu Ser Glu Glu Ala Leu
1               5

<210> SEQ ID NO 16
<211> LENGTH: 9
<212> TYPE: PRT
<213> ORGANISM: Rivularia sp.

<400> SEQUENCE: 16

Leu Ala Glu Leu Ser Glu Glu Thr Leu
1               5

<210> SEQ ID NO 17
<211> LENGTH: 9
<212> TYPE: PRT
<213> ORGANISM: Arthrospira sp. PCC 8005

<400> SEQUENCE: 17

Leu Ala Glu Leu Ser Glu Glu Ala Ile
1               5

<210> SEQ ID NO 18
<211> LENGTH: 64
<212> TYPE: PRT
<213> ORGANISM: Prochloron sp.

<400> SEQUENCE: 18

Met Asp Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Lys Ile Thr Ala Cys Ile
        35                  40                  45

Thr Phe Cys Ala Tyr Asp Gly Glu Leu Glu His His His His His
    50                  55                  60

<210> SEQ ID NO 19
<211> LENGTH: 66
<212> TYPE: PRT
<213> ORGANISM: Prochloron sp. 06037A
```

<400> SEQUENCE: 19

Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Thr Leu Pro Val Pro Thr Leu Cys
        35                  40                  45

Ser Tyr Asp Gly Val Asp Ala Ser Thr Val Pro Thr Leu Cys Ser Tyr
    50                  55                  60

Asp Asp
65

<210> SEQ ID NO 20
<211> LENGTH: 67
<212> TYPE: PRT
<213> ORGANISM: Prochloron sp.

<400> SEQUENCE: 20

Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Thr Phe Pro Val Pro Thr Val Cys
        35                  40                  45

Ser Tyr Asp Gly Val Asp Ala Ser Thr Ser Ile Ala Pro Phe Cys Ser
    50                  55                  60

Tyr Asp Asp
65

<210> SEQ ID NO 21
<211> LENGTH: 81
<212> TYPE: PRT
<213> ORGANISM: Prochloron sp.

<400> SEQUENCE: 21

Met Asn Lys Lys Asn Ile Leu Pro Gln Leu Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Gly Val Asp Ala Ser Thr Ser Ile Ala Pro Phe Cys Ser
        35                  40                  45

Tyr Asp Gly Val Asp Ala Ser Thr Ser Ile Ala Pro Phe Cys Ser Tyr
    50                  55                  60

Asp Gly Val Asp Ala Ser Thr Ser Ile Ala Pro Phe Cys Ser Tyr Asp
65                  70                  75                  80

Asp

<210> SEQ ID NO 22
<211> LENGTH: 93
<212> TYPE: PRT
<213> ORGANISM: Nostoc spongiaeforme

<400> SEQUENCE: 22

Met Asp Lys Lys Asn Ile Leu Pro Gln Gln Gly Lys Pro Val Ile Arg
1               5                   10                  15

Ile Thr Thr Gly Gln Leu Pro Ser Phe Leu Ala Glu Leu Ser Glu Glu
            20                  25                  30

```
Ala Leu Gly Asp Ala Gly Val Gly Ala Ser Ala Thr Gly Cys Met Cys
            35                  40                  45

Ala Tyr Asp Gly Ala Gly Ala Ser Ala Thr Gly Cys Met Cys Ala Tyr
 50                  55                  60

Asp Gly Ala Gly Ala Ser Ala Thr Ala Cys Ala Cys Ala Tyr Asp Gly
 65                  70                  75                  80

Ala Gly Ala Ser Ala Thr Ala Cys Ala Cys Ala Tyr Glu
                85                  90

<210> SEQ ID NO 23
<211> LENGTH: 83
<212> TYPE: PRT
<213> ORGANISM: Microcystis aeruginosa

<400> SEQUENCE: 23

Met Asp Lys Lys Asn Ile Leu Pro Gln Gln Gly Lys Pro Val Phe Arg
 1               5                  10                  15

Thr Thr Thr Gly Lys Leu Pro Ser Tyr Leu Ala Glu Leu Ser Glu Glu
                20                  25                  30

Ala Leu Gly Gly Asn Gly Leu Glu Ala Ser His Cys Ala Thr Ile Cys
            35                  40                  45

Ala Phe Asp Gly Ala Glu Ala Ser His Cys Ala Thr Ile Cys Ala Phe
 50                  55                  60

Asp Gly Ala Glu Ala Ser His Cys Ala Thr Ile Cys Ala Phe Asp Gly
 65                  70                  75                  80

Asp Glu Ala

<210> SEQ ID NO 24
<211> LENGTH: 83
<212> TYPE: PRT
<213> ORGANISM: Microcystis aeruginosa

<400> SEQUENCE: 24

Met Asp Lys Lys Asn Leu Leu Pro Asn Gln Gly Ala Pro Val Ile Arg
 1               5                  10                  15

Gly Ile Ser Gly Lys Leu Pro Ser His Leu Ala Glu Leu Ser Glu Glu
                20                  25                  30

Ala Leu Gly Gly Asn Gly Leu Glu Ala Ser Tyr Thr Ser Ser Ile Cys
            35                  40                  45

Ala Phe Asp Gly Ala Glu Ala Ser Val Leu Ala Thr Phe Cys Ala Phe
 50                  55                  60

Asp Gly Ala Glu Ala Ser Val Thr Val Thr Ile Cys Ala Phe Asp Gly
 65                  70                  75                  80

Asp Glu Ala

<210> SEQ ID NO 25
<211> LENGTH: 60
<212> TYPE: PRT
<213> ORGANISM: Arthrospira sp. PCC 8005

<400> SEQUENCE: 25

Met Asn Lys Lys Asn Ile Ser Pro Asn Pro Gln Gln Pro Val Asp Arg
 1               5                  10                  15

Val Pro Thr Gly Gln Leu Pro Ser Ala Leu Ala Glu Leu Ser Glu Glu
                20                  25                  30

Ala Ile Gly Ser Leu Glu Ala Leu Pro Ser Gly Phe Met Gly Thr Gly
            35                  40                  45
```

```
Cys Phe Pro His Cys Ser Tyr Asp Gly Asp Asp Glu
    50                  55                  60

<210> SEQ ID NO 26
<211> LENGTH: 57
<212> TYPE: PRT
<213> ORGANISM: Arthrospira sp. PCC 8005

<400> SEQUENCE: 26

Met Asp Lys Lys Asn Ile Ser Pro Asn Pro Gln Gln Pro Val Asp Arg
1               5                   10                  15

Ile Pro Thr Gly Gln Leu Pro Ser Ala Leu Ala Glu Leu Ser Glu Glu
            20                  25                  30

Ala Ile Gly Ser Gln Ala Gln Ala Gly Arg Lys Cys Arg Ser Ala Glu
        35                  40                  45

Leu Cys Ser Tyr Glu Gly Asp Asp Glu
    50                  55

<210> SEQ ID NO 27
<211> LENGTH: 65
<212> TYPE: PRT
<213> ORGANISM: Rivularia sp. PCC 7116

<400> SEQUENCE: 27

Met Asp Lys Lys Asn Ile Ile Pro Gln Gln Ala Gln Pro Val Val Arg
1               5                   10                  15

Val Ser Gln Gly Thr Gln Ala Asp Leu Leu Ala Glu Leu Ser Glu Glu
            20                  25                  30

Thr Leu Ala Ser Thr Pro Gly Ala Gly Ala Ser Met Lys Thr Asn Asp
        35                  40                  45

Met Thr Leu Ala Cys Tyr Cys Val Cys Ser Tyr Asp Gly Asp Asp Ala
    50                  55                  60

Glu
65

<210> SEQ ID NO 28
<211> LENGTH: 40
<212> TYPE: PRT
<213> ORGANISM: Bacillus thuringiensis

<400> SEQUENCE: 28

Met Glu Asn Ala Arg Arg Gln Ser Ser Glu Gly Lys Glu Ala Ile Gln
1               5                   10                  15

Met Glu Gln Lys Lys Ile Leu Asp Ile Lys Leu Thr Glu Thr Gly Lys
            20                  25                  30

Ile Asn Tyr Ala His Lys Pro Asp
        35                  40

<210> SEQ ID NO 29
<211> LENGTH: 19
<212> TYPE: PRT
<213> ORGANISM: Artificial sequence
<220> FEATURE:
<223> OTHER INFORMATION: Preferred cyanobactin leader sequence
<220> FEATURE:
<221> NAME/KEY: VARIANT
<222> LOCATION: (1)..(1)
<223> OTHER INFORMATION: Xaa is Thr, Gln or Lys
<220> FEATURE:
<221> NAME/KEY: VARIANT
<222> LOCATION: (2)..(2)
<223> OTHER INFORMATION: Xaa is Gln, Leu or Lys

```
<220> FEATURE:
<221> NAME/KEY: VARIANT
<222> LOCATION: (3)..(3)
<223> OTHER INFORMATION: Xaa is Ala, Pro or Ser
<220> FEATURE:
<221> NAME/KEY: VARIANT
<222> LOCATION: (4)..(4)
<223> OTHER INFORMATION: Xaa is Ala, Asp or Ser
<220> FEATURE:
<221> NAME/KEY: VARIANT
<222> LOCATION: (5)..(5)
<223> OTHER INFORMATION: Xaa is Glu, Leu, Ala, His or Gln or Tyr
<220> FEATURE:
<221> NAME/KEY: VARIANT
<222> LOCATION: (10)..(10)
<223> OTHER INFORMATION: Xaa is Ser or Thr, preferably Ser
<220> FEATURE:
<221> NAME/KEY: VARIANT
<222> LOCATION: (13)..(13)
<223> OTHER INFORMATION: Xaa is Ala, Val, Thr or Asn
<220> FEATURE:
<221> NAME/KEY: VARIANT
<222> LOCATION: (14)..(14)
<223> OTHER INFORMATION: Xaa is Leu or Ile or optionally absent
<220> FEATURE:
<221> NAME/KEY: VARIANT
<222> LOCATION: (16)..(16)
<223> OTHER INFORMATION: Xaa is Gly or Ala, preferably Gly
<220> FEATURE:
<221> NAME/KEY: VARIANT
<222> LOCATION: (17)..(17)
<223> OTHER INFORMATION: Xaa is Ser, Asp, Gly, or absent
<220> FEATURE:
<221> NAME/KEY: VARIANT
<222> LOCATION: (18)..(18)
<223> OTHER INFORMATION: Xaa is Thr, Leu, Asn, Ala or Val or absent
<220> FEATURE:
<221> NAME/KEY: VARIANT
<222> LOCATION: (19)..(19)
<223> OTHER INFORMATION: Xaa is Thr, Pro, Ala, Glu, Gly, Asp or absent

<400> SEQUENCE: 29

Xaa Xaa Xaa Xaa Xaa Leu Ala Glu Leu Xaa Glu Glu Xaa Xaa Leu Xaa
1               5                   10                  15

Xaa Xaa Xaa

<210> SEQ ID NO 30
<211> LENGTH: 24
<212> TYPE: PRT
<213> ORGANISM: Artificial sequence
<220> FEATURE:
<223> OTHER INFORMATION: Preferred cyanobactin leader sequence
<220> FEATURE:
<221> NAME/KEY: VARIANT
<222> LOCATION: (1)..(1)
<223> OTHER INFORMATION: Xaa is Arg or absent
<220> FEATURE:
<221> NAME/KEY: VARIANT
<222> LOCATION: (2)..(2)
<223> OTHER INFORMATION: Xaa is Leu, Ile, Thr, Gly, or Val or absent
<220> FEATURE:
<221> NAME/KEY: VARIANT
<222> LOCATION: (3)..(3)
<223> OTHER INFORMATION: Xaa is Thr,Ile,Pro,Ser or absent
<220> FEATURE:
<221> NAME/KEY: VARIANT
<222> LOCATION: (4)..(4)
<223> OTHER INFORMATION: Xaa is Ala,Thr,Ser,Gln or absent
<220> FEATURE:
<221> NAME/KEY: VARIANT
<222> LOCATION: (5)..(5)
<223> OTHER INFORMATION: Xaa is Gly or absent
<220> FEATURE:
<221> NAME/KEY: VARIANT
<222> LOCATION: (6)..(6)
<223> OTHER INFORMATION: Xaa is Thr,Gln or Lys
```

```
<220> FEATURE:
<221> NAME/KEY: VARIANT
<222> LOCATION: (7)..(7)
<223> OTHER INFORMATION: Xaa is Gln,Leu or Lys
<220> FEATURE:
<221> NAME/KEY: VARIANT
<222> LOCATION: (8)..(8)
<223> OTHER INFORMATION: Xaa is Ala, Pro or Ser
<220> FEATURE:
<221> NAME/KEY: VARIANT
<222> LOCATION: (9)..(9)
<223> OTHER INFORMATION: Xaa is Ala, Asp or Ser
<220> FEATURE:
<221> NAME/KEY: VARIANT
<222> LOCATION: (10)..(10)
<223> OTHER INFORMATION: Xaa is Glu, Leu, Ala, His or Gln or Tyr
<220> FEATURE:
<221> NAME/KEY: VARIANT
<222> LOCATION: (15)..(15)
<223> OTHER INFORMATION: Xaa is Ser or Thr, preferably Ser
<220> FEATURE:
<221> NAME/KEY: VARIANT
<222> LOCATION: (18)..(18)
<223> OTHER INFORMATION: Xaa is Ala, Val, Thr or Asn
<220> FEATURE:
<221> NAME/KEY: VARIANT
<222> LOCATION: (19)..(19)
<223> OTHER INFORMATION: Xaa is Leu, Ile or absent
<220> FEATURE:
<221> NAME/KEY: VARIANT
<222> LOCATION: (21)..(21)
<223> OTHER INFORMATION: Xaa is Gly or Ala, preferably Gly
<220> FEATURE:
<221> NAME/KEY: VARIANT
<222> LOCATION: (22)..(22)
<223> OTHER INFORMATION: Xaa is Ser, Asp, Gly, or absent
<220> FEATURE:
<221> NAME/KEY: VARIANT
<222> LOCATION: (23)..(23)
<223> OTHER INFORMATION: Xaa is Thr, Leu, Asn, Ala or Val or absent
<220> FEATURE:
<221> NAME/KEY: VARIANT
<222> LOCATION: (24)..(24)
<223> OTHER INFORMATION: Xaa is Thr, Pro, Ala, Glu, Gly, Asp or absent

<400> SEQUENCE: 30

Xaa Xaa Xaa Xaa Xaa Xaa Xaa Xaa Xaa Xaa Leu Ala Glu Leu Xaa Glu
1               5                   10                  15

Glu Xaa Xaa Leu Xaa Xaa Xaa Xaa
            20

<210> SEQ ID NO 31
<211> LENGTH: 23
<212> TYPE: PRT
<213> ORGANISM: Prochloron sp.
<220> FEATURE:
<221> NAME/KEY: VARIANT
<222> LOCATION: (1)..(5)
<223> OTHER INFORMATION: X1, which may be absent. If present, up to 4
      amino acids may be present or absent, and  X1 is Gly, Ala Gly, Thr
      Ala Gly, Leu Thr Ala Gly or Arg Leu Thr Ala Gly.

<400> SEQUENCE: 31

Xaa Xaa Xaa Xaa Xaa Gln Leu Ser Ser Gln Leu Ala Glu Leu Ser Glu
1               5                   10                  15

Glu Ala Leu Gly Asp Ala Gly
            20

<210> SEQ ID NO 32
<211> LENGTH: 18
<212> TYPE: PRT
<213> ORGANISM: Prochloron sp.
```

-continued

```
<400> SEQUENCE: 32

Gln Leu Ser Ser Gln Leu Ala Glu Leu Ser Glu Glu Ala Leu Gly Asp
1               5                   10                  15

Ala Gly

<210> SEQ ID NO 33
<211> LENGTH: 19
<212> TYPE: PRT
<213> ORGANISM: Prochloron sp.

<400> SEQUENCE: 33

Gly Gln Leu Ser Ser Gln Leu Ala Glu Leu Ser Glu Glu Ala Leu Gly
1               5                   10                  15

Asp Ala Gly

<210> SEQ ID NO 34
<211> LENGTH: 20
<212> TYPE: PRT
<213> ORGANISM: Prochloron sp.

<400> SEQUENCE: 34

Ala Gly Gln Leu Ser Ser Gln Leu Ala Glu Leu Ser Glu Glu Ala Leu
1               5                   10                  15

Gly Asp Ala Gly
            20

<210> SEQ ID NO 35
<211> LENGTH: 21
<212> TYPE: PRT
<213> ORGANISM: Prochloron sp.

<400> SEQUENCE: 35

Thr Ala Gly Gln Leu Ser Ser Gln Leu Ala Glu Leu Ser Glu Glu Ala
1               5                   10                  15

Leu Gly Asp Ala Gly
            20

<210> SEQ ID NO 36
<211> LENGTH: 22
<212> TYPE: PRT
<213> ORGANISM: Prochloron sp.

<400> SEQUENCE: 36

Leu Thr Ala Gly Gln Leu Ser Ser Gln Leu Ala Glu Leu Ser Glu Glu
1               5                   10                  15

Ala Leu Gly Asp Ala Gly
            20

<210> SEQ ID NO 37
<211> LENGTH: 23
<212> TYPE: PRT
<213> ORGANISM: Prochloron sp.

<400> SEQUENCE: 37

Arg Leu Thr Ala Gly Gln Leu Ser Ser Gln Leu Ala Glu Leu Ser Glu
1               5                   10                  15

Glu Ala Leu Gly Asp Ala Gly
            20

<210> SEQ ID NO 38
<211> LENGTH: 11
```

```
<212> TYPE: PRT
<213> ORGANISM: Artificial sequence
<220> FEATURE:
<223> OTHER INFORMATION: Synthetic peptidyl linker

<400> SEQUENCE: 38

Ala Gly Ala Gly Ala Gly Ala Gly Ala Gly Ala
1               5                   10

<210> SEQ ID NO 39
<211> LENGTH: 823
<212> TYPE: PRT
<213> ORGANISM: Artificial sequence
<220> FEATURE:
<223> OTHER INFORMATION: Modified heterocyclase

<400> SEQUENCE: 39

Met Ser His His His His His His Asp Tyr Asp Glu Asn Leu Tyr Phe
1               5                   10                  15

Gln Gly Ser Gln Leu Ser Ser Gln Leu Ala Glu Leu Ser Glu Glu Ala
            20                  25                  30

Leu Gly Asp Ala Gly Ala Gly Ala Gly Ala Gly Ala Gly Ala Gly Ala
        35                  40                  45

Met Gln Ser Thr Pro Leu Leu Gln Ile Gln Pro His Phe His Val Glu
    50                  55                  60

Val Ile Glu Pro Lys Gln Val Tyr Leu Gly Glu Gln Ala Asn His
65                  70                  75                  80

Ala Leu Thr Gly Gln Leu Tyr Cys Gln Ile Leu Pro Leu Leu Asn Gly
                85                  90                  95

Gln Tyr Thr Leu Glu Gln Ile Val Glu Lys Leu Asp Gly Glu Val Pro
            100                 105                 110

Pro Glu Tyr Ile Asp Tyr Val Leu Glu Arg Leu Ala Glu Lys Gly Tyr
        115                 120                 125

Leu Thr Glu Ala Ala Pro Glu Leu Ser Ser Glu Val Ala Ala Phe Trp
130                 135                 140

Ser Glu Leu Gly Ile Ala Pro Pro Val Ala Glu Ala Leu Arg Gln
145                 150                 155                 160

Pro Val Thr Leu Thr Pro Val Gly Asn Ile Ser Glu Val Thr Val Ala
                165                 170                 175

Ala Leu Thr Thr Ala Leu Arg Asp Ile Gly Ile Ser Val Gln Thr Pro
            180                 185                 190

Thr Glu Ala Gly Ser Pro Thr Ala Leu Asn Val Val Leu Thr Asp Asp
        195                 200                 205

Tyr Leu Gln Pro Glu Leu Ala Lys Ile Asn Lys Gln Ala Leu Glu Ser
    210                 215                 220

Gln Gln Thr Trp Leu Leu Val Lys Pro Val Ser Val Leu Trp Leu
225                 230                 235                 240

Gly Pro Val Phe Val Pro Gly Lys Thr Gly Cys Trp Asp Cys Leu Ala
                245                 250                 255

His Arg Leu Arg Gly Asn Arg Glu Val Glu Ala Ser Val Leu Arg Gln
            260                 265                 270

Lys Gln Ala Gln Gln Arg Asn Gly Gln Ser Gly Ser Val Ile Gly
        275                 280                 285

Cys Leu Pro Thr Ala Arg Ala Thr Leu Pro Ser Thr Leu Gln Thr Gly
    290                 295                 300

Leu Gln Phe Ala Ala Thr Glu Ile Ala Lys Trp Ile Val Lys Tyr His
305                 310                 315                 320
```

```
Val Asn Ala Thr Ala Pro Gly Thr Val Phe Pro Thr Leu Asp Gly
                325                 330                 335

Lys Ile Ile Thr Leu Asn His Ser Ile Leu Asp Leu Lys Ser His Ile
            340                 345                 350

Leu Ile Lys Arg Ser Gln Cys Pro Thr Cys Gly Asp Pro Lys Ile Leu
                355                 360                 365

Gln His Arg Gly Phe Glu Pro Leu Lys Leu Glu Ser Arg Pro Lys Gln
        370                 375                 380

Phe Thr Ser Asp Gly Gly His Arg Gly Thr Thr Pro Glu Gln Thr Val
385                 390                 395                 400

Gln Lys Tyr Gln His Leu Ile Ser Pro Val Thr Gly Val Val Thr Glu
                405                 410                 415

Leu Val Arg Ile Thr Asp Pro Ala Asn Pro Leu Val His Thr Tyr Arg
                420                 425                 430

Ala Gly His Ser Phe Gly Ser Ala Thr Ser Leu Arg Gly Leu Arg Asn
        435                 440                 445

Thr Leu Lys His Lys Ser Ser Gly Lys Gly Lys Thr Asp Ser Gln Ser
        450                 455                 460

Lys Ala Ser Gly Leu Cys Glu Ala Val Glu Arg Tyr Ser Gly Ile Phe
465                 470                 475                 480

Gln Gly Asp Glu Pro Arg Lys Arg Ala Thr Leu Ala Glu Leu Gly Asp
                485                 490                 495

Leu Ala Ile His Pro Glu Gln Cys Leu Cys Phe Ser Asp Gly Gln Tyr
                500                 505                 510

Ala Asn Arg Glu Thr Leu Asn Glu Gln Ala Thr Val Ala His Asp Trp
            515                 520                 525

Ile Pro Gln Arg Phe Asp Ala Ser Gln Ala Ile Glu Trp Thr Pro Val
            530                 535                 540

Trp Ser Leu Thr Glu Gln Thr His Lys Tyr Leu Pro Thr Ala Leu Cys
545                 550                 555                 560

Tyr Tyr His Tyr Pro Leu Pro Pro Glu His Arg Phe Ala Arg Gly Asp
                565                 570                 575

Ser Asn Gly Asn Ala Ala Gly Asn Thr Leu Glu Glu Ala Ile Leu Gln
            580                 585                 590

Gly Phe Met Glu Leu Val Glu Arg Asp Gly Val Ala Leu Trp Trp Tyr
        595                 600                 605

Asn Arg Leu Arg Arg Pro Ala Val Asp Leu Gly Ser Phe Asn Glu Pro
610                 615                 620

Tyr Phe Val Gln Leu Gln Gln Phe Tyr Arg Glu Asn Asp Arg Asp Leu
625                 630                 635                 640

Trp Val Leu Asp Leu Thr Ala Asp Leu Gly Ile Pro Ala Phe Ala Gly
                645                 650                 655

Val Ser Asn Arg Lys Thr Gly Ser Ser Glu Arg Leu Ile Leu Gly Phe
                660                 665                 670

Gly Ala His Leu Asp Pro Thr Ile Ala Ile Leu Arg Ala Val Thr Glu
        675                 680                 685

Val Asn Gln Ile Gly Leu Glu Leu Asp Lys Val Pro Asp Glu Asn Leu
        690                 695                 700

Lys Ser Asp Ala Thr Asp Trp Leu Ile Thr Glu Lys Leu Ala Asp His
705                 710                 715                 720

Pro Tyr Leu Leu Pro Asp Thr Thr Gln Pro Leu Lys Thr Ala Gln Asp
                725                 730                 735
```

```
Tyr Pro Lys Arg Trp Ser Asp Asp Ile Tyr Thr Asp Val Met Thr Cys
            740                 745                 750

Val Asn Ile Ala Gln Gln Ala Gly Leu Glu Thr Leu Val Ile Asp Gln
        755                 760                 765

Thr Arg Pro Asp Ile Gly Leu Asn Val Val Lys Val Thr Val Pro Gly
    770                 775                 780

Met Arg His Phe Trp Ser Arg Phe Gly Glu Gly Arg Leu Tyr Asp Val
785                 790                 795                 800

Pro Val Lys Leu Gly Trp Leu Asp Glu Pro Leu Thr Glu Ala Gln Met
                805                 810                 815

Asn Pro Thr Pro Met Pro Phe
            820

<210> SEQ ID NO 40
<211> LENGTH: 824
<212> TYPE: PRT
<213> ORGANISM: Artificial sequence
<220> FEATURE:
<223> OTHER INFORMATION: Modified heterocyclase MicroD_Q21_5GA

<400> SEQUENCE: 40

Met Ser His His His His His His Asp Tyr Asp Glu Asn Leu Tyr Phe
1               5                   10                  15

Gln Gly Ser Gln Leu Ser Ser Gln Leu Ala Glu Leu Ser Glu Glu Ala
            20                  25                  30

Leu Gly Asp Ala Gly Ala Gly Ala Gly Ala Gly Ala Gly Ala Lys Leu
        35                  40                  45

Met Gln Ser Thr Pro Leu Leu Gln Ile Gln Pro His Phe His Val Glu
    50                  55                  60

Val Ile Glu Pro Lys Gln Val Tyr Leu Gly Glu Gln Ala Asn Tyr
65                  70                  75                  80

Ala Leu Thr Gly Gln Leu Tyr Cys Gln Ile Leu Pro Leu Leu Asp Gly
                85                  90                  95

Gln His Ser Arg Glu Gln Ile Val Glu Lys Leu Asp Gly Glu Val Pro
            100                 105                 110

Ser Glu Tyr Ile Asp Tyr Val Leu Asp Arg Leu Ala Glu Lys Gly Tyr
        115                 120                 125

Leu Thr Glu Ala Ala Pro Glu Leu Ser Ser Glu Val Ala Ala Phe Trp
    130                 135                 140

Ser Glu Leu Gly Ile Ala Pro Pro Val Ala Ala Glu Ala Leu Arg Gln
145                 150                 155                 160

Ser Val Thr Leu Thr Pro Val Gly Asn Ile Ser Glu Val Thr Val Ala
                165                 170                 175

Ala Leu Thr Thr Ala Leu Arg Asp Ile Gly Ile Ser Val Gln Thr Pro
            180                 185                 190

Thr Glu Ala Gly Ser Pro Thr Ala Leu Asn Val Val Leu Thr Asp Asp
        195                 200                 205

Tyr Leu Gln Pro Glu Leu Ala Lys Ile Asn Lys Gln Ala Leu Glu Ser
    210                 215                 220

Gln Gln Thr Trp Leu Leu Val Lys Pro Val Gly Ser Val Leu Trp Leu
225                 230                 235                 240

Gly Pro Val Phe Val Pro Gly Lys Thr Gly Cys Trp Asp Cys Leu Ala
                245                 250                 255

His Arg Leu Arg Gly Asn Arg Glu Val Glu Ala Ser Val Leu Gln Gln
            260                 265                 270
```

```
Lys Gln Ala Gln Gln Gln Arg Asn Gly Gln Ser Gly Ser Val Ile Gly
            275                 280                 285
Cys Leu Pro Thr Ala Arg Ala Thr Leu Pro Ser Thr Leu Gln Thr Gly
        290                 295                 300
Leu Gln Phe Ala Ala Thr Glu Ile Ala Lys Trp Ile Val Lys His His
305                 310                 315                 320
Val Lys Ala Thr Ala Pro Gly Thr Val Phe Phe Pro Thr Leu Asp Gly
                325                 330                 335
Lys Ile Ile Thr Phe Asn His Thr Val Ile Asp Leu Lys Ser His Val
                340                 345                 350
Leu Val Arg Arg Ser Gln Cys Pro Ser Cys Gly Asp Arg Gln Ile Leu
            355                 360                 365
His Arg Gln Gly Phe Glu Pro Val Lys Leu Val Ser Arg Arg Lys His
        370                 375                 380
Phe Thr His Asp Gly Gly His Arg Ala Phe Thr Pro Glu Gln Thr Val
385                 390                 395                 400
Gln Lys Tyr Gln His Leu Val Ser Pro Ile Thr Gly Val Val Thr Glu
                405                 410                 415
Leu Val Arg Leu Thr Asp Pro Ala Asn Pro Leu Val His Thr Tyr Lys
            420                 425                 430
Ala Gly His Ala Phe Gly Ser Ala Thr Thr Leu Arg Gly Leu Arg Asn
        435                 440                 445
Thr Leu Lys Tyr Lys Ser Ser Gly Lys Gly Lys Thr Asp Ile Gln Ser
        450                 455                 460
Arg Ala Ser Gly Leu Cys Glu Ala Ile Glu Arg Tyr Ser Gly Ile Phe
465                 470                 475                 480
Gln Gly Asp Glu Pro Arg Lys Arg Ala Thr Leu Ala Glu Leu Gly Asp
                485                 490                 495
Leu Ala Leu His Pro Glu Ser Leu Leu Tyr Phe Ser Asn Thr Gln Tyr
            500                 505                 510
Ala Asn Arg Glu Glu Leu Asn Ala Gln Gly Ser Ala Ala Ala Tyr Arg
            515                 520                 525
Trp Ile Pro Asn Arg Phe Asp Val Ser Gln Ala Ile Asp Trp Thr Pro
        530                 535                 540
Val Trp Ser Leu Thr Glu Gln Lys His Lys Tyr Val Pro Thr Ala Phe
545                 550                 555                 560
Cys Tyr Tyr Gly Tyr Pro Leu Pro Glu Glu Gln Arg Phe Cys Lys Ala
                565                 570                 575
Asp Ser Asn Gly Asn Ala Ala Gly Asn Thr Leu Glu Glu Ala Ile Leu
            580                 585                 590
Gln Gly Phe Leu Glu Leu Val Glu Arg Asp Ser Ile Ala Met Trp Trp
        595                 600                 605
Tyr Asn Arg Ile Arg Arg Pro Ala Val Asp Leu Ser Thr Phe Asp Glu
        610                 615                 620
Pro Tyr Phe Val Asp Leu Gln Gln Phe Tyr Gln Gln Asn Arg Glu
625                 630                 635                 640
Leu Trp Val Leu Asp Val Thr Ala Asp Leu Gly Ile Pro Ala Phe Ala
                645                 650                 655
Gly Phe Ser Arg Arg Thr Val Gly Thr Ser Glu Arg Ile Ser Ile Gly
            660                 665                 670
Phe Gly Ala His Leu Asp Pro Thr Ile Ala Ile Leu Arg Ala Leu Thr
        675                 680                 685
Glu Val Ser Gln Val Gly Leu Glu Leu Asp Lys Ile Pro Asp Asp Lys
```

```
                690             695             700
Leu Asp Gly Glu Ser Lys Asp Trp Met Leu Asn Val Thr Val Glu Asn
705             710             715             720

His Pro Trp Leu Ala Pro Asp Pro Ser Val Pro Met Lys Thr Ala Ser
            725             730             735

Asp Tyr Pro Lys Arg Trp Ser Asp Asp Ile His Thr Asp Val Met Asn
            740             745             750

Cys Val Lys Thr Ala Gln Thr Ala Gly Leu Glu Val Met Val Leu Asp
            755             760             765

Gln Thr Arg Pro Asp Ile Gly Leu Asn Val Val Lys Val Ile Ile Pro
770             775             780

Gly Met Arg Thr Phe Trp Thr Arg Phe Gly Gln Gly Arg Leu Tyr Asp
785             790             795             800

Ile Pro Val Lys Leu Gly Trp Leu Asp Ala Pro Leu Ala Glu Glu Glu
            805             810             815

Leu Asn Gln Thr Asn Ile Pro Phe
            820

<210> SEQ ID NO 41
<211> LENGTH: 832
<212> TYPE: PRT
<213> ORGANISM: Artificial sequence
<220> FEATURE:
<223> OTHER INFORMATION: Modified heterocyclase MicroD_Q21_9GA

<400> SEQUENCE: 41

Met Ser His His His His His His Asp Tyr Asp Glu Asn Leu Tyr Phe
1               5               10              15

Gln Gly Ser Gln Leu Ser Ser Gln Leu Ala Glu Leu Ser Glu Glu Ala
            20              25              30

Leu Gly Asp Ala Gly Ala Gly Ala Gly Ala Gly Ala Gly Ala Gly Ala
            35              40              45

Gly Ala Gly Ala Gly Ala Lys Leu Met Gln Ser Thr Pro Leu Leu Gln
50              55              60

Ile Gln Pro His Phe His Val Glu Val Ile Glu Pro Lys Gln Val Tyr
65              70              75              80

Leu Leu Gly Glu Gln Ala Asn Tyr Ala Leu Thr Gly Gln Leu Tyr Cys
            85              90              95

Gln Ile Leu Pro Leu Leu Asp Gly Gln His Ser Arg Glu Gln Ile Val
            100             105             110

Glu Lys Leu Asp Gly Glu Val Pro Ser Glu Tyr Ile Asp Tyr Val Leu
            115             120             125

Asp Arg Leu Ala Glu Lys Gly Tyr Leu Thr Glu Ala Ala Pro Glu Leu
130             135             140

Ser Ser Glu Val Ala Ala Phe Trp Ser Glu Leu Gly Ile Ala Pro Pro
145             150             155             160

Val Ala Ala Glu Ala Leu Arg Gln Ser Val Thr Leu Thr Pro Val Gly
            165             170             175

Asn Ile Ser Glu Val Thr Val Ala Ala Leu Thr Thr Ala Leu Arg Asp
            180             185             190

Ile Gly Ile Ser Val Gln Thr Pro Thr Glu Ala Gly Ser Pro Thr Ala
            195             200             205

Leu Asn Val Val Leu Thr Asp Asp Tyr Leu Gln Pro Glu Leu Ala Lys
210             215             220

Ile Asn Lys Gln Ala Leu Glu Ser Gln Gln Thr Trp Leu Leu Val Lys
```

```
            225                 230                 235                 240
    Pro Val Gly Ser Val Leu Trp Leu Gly Pro Val Phe Val Pro Gly Lys
                    245                 250                 255

Thr Gly Cys Trp Asp Cys Leu Ala His Arg Leu Arg Gly Asn Arg Glu
                    260                 265                 270

Val Glu Ala Ser Val Leu Gln Gln Lys Gln Ala Gln Gln Gln Arg Asn
                    275                 280                 285

Gly Gln Ser Gly Ser Val Ile Gly Cys Leu Pro Thr Ala Arg Ala Thr
                290                 295                 300

Leu Pro Ser Thr Leu Gln Thr Gly Leu Gln Phe Ala Ala Thr Glu Ile
    305                 310                 315                 320

Ala Lys Trp Ile Val Lys His Val Lys Ala Thr Ala Pro Gly Thr
                    325                 330                 335

Val Phe Phe Pro Thr Leu Asp Gly Lys Ile Ile Thr Phe Asn His Thr
                    340                 345                 350

Val Ile Asp Leu Lys Ser His Val Leu Val Arg Arg Ser Gln Cys Pro
                    355                 360                 365

Ser Cys Gly Asp Arg Gln Ile Leu His Arg Gln Gly Phe Glu Pro Val
                370                 375                 380

Lys Leu Val Ser Arg Arg Lys His Phe Thr His Asp Gly Gly His Arg
    385                 390                 395                 400

Ala Phe Thr Pro Glu Gln Thr Val Gln Lys Tyr Gln His Leu Val Ser
                    405                 410                 415

Pro Ile Thr Gly Val Val Thr Glu Leu Val Arg Leu Thr Asp Pro Ala
                    420                 425                 430

Asn Pro Leu Val His Thr Tyr Lys Ala Gly His Ala Phe Gly Ser Ala
                    435                 440                 445

Thr Thr Leu Arg Gly Leu Arg Asn Thr Leu Lys Tyr Lys Ser Ser Gly
                450                 455                 460

Lys Gly Lys Thr Asp Ile Gln Ser Arg Ala Ser Gly Leu Cys Glu Ala
    465                 470                 475                 480

Ile Glu Arg Tyr Ser Gly Ile Phe Gln Gly Asp Glu Pro Arg Lys Arg
                    485                 490                 495

Ala Thr Leu Ala Glu Leu Gly Asp Leu Ala Leu His Pro Glu Ser Leu
                    500                 505                 510

Leu Tyr Phe Ser Asn Thr Gln Tyr Ala Asn Arg Glu Glu Leu Asn Ala
                    515                 520                 525

Gln Gly Ser Ala Ala Ala Tyr Arg Trp Ile Pro Asn Arg Phe Asp Val
                530                 535                 540

Ser Gln Ala Ile Asp Trp Thr Pro Val Trp Ser Leu Thr Glu Gln Lys
    545                 550                 555                 560

His Lys Tyr Val Pro Thr Ala Phe Cys Tyr Tyr Gly Tyr Pro Leu Pro
                    565                 570                 575

Glu Glu Gln Arg Phe Cys Lys Ala Asp Ser Asn Gly Asn Ala Ala Gly
                    580                 585                 590

Asn Thr Leu Glu Glu Ala Ile Leu Gln Gly Phe Leu Glu Leu Val Glu
                    595                 600                 605

Arg Asp Ser Ile Ala Met Trp Trp Tyr Asn Arg Ile Arg Arg Pro Ala
                    610                 615                 620

Val Asp Leu Ser Thr Phe Asp Glu Pro Tyr Phe Val Asp Leu Gln Gln
    625                 630                 635                 640

Phe Tyr Gln Gln Gln Asn Arg Glu Leu Trp Val Leu Asp Val Thr Ala
                    645                 650                 655
```

```
Asp Leu Gly Ile Pro Ala Phe Ala Gly Phe Ser Arg Arg Thr Val Gly
            660                 665                 670

Thr Ser Glu Arg Ile Ser Ile Gly Phe Gly Ala His Leu Asp Pro Thr
        675                 680                 685

Ile Ala Ile Leu Arg Ala Leu Thr Glu Val Ser Gln Val Gly Leu Glu
    690                 695                 700

Leu Asp Lys Ile Pro Asp Asp Lys Leu Asp Gly Glu Ser Lys Asp Trp
705                 710                 715                 720

Met Leu Asn Val Thr Val Glu Asn His Pro Trp Leu Ala Pro Asp Pro
                725                 730                 735

Ser Val Pro Met Lys Thr Ala Ser Asp Tyr Pro Lys Arg Trp Ser Asp
            740                 745                 750

Asp Ile His Thr Asp Val Met Asn Cys Val Lys Thr Ala Gln Thr Ala
        755                 760                 765

Gly Leu Glu Val Met Val Leu Asp Gln Thr Arg Pro Asp Ile Gly Leu
    770                 775                 780

Asn Val Val Lys Val Ile Ile Pro Gly Met Arg Thr Phe Trp Thr Arg
785                 790                 795                 800

Phe Gly Gln Gly Arg Leu Tyr Asp Ile Pro Val Lys Leu Gly Trp Leu
                805                 810                 815

Asp Ala Pro Leu Ala Glu Glu Leu Asn Gln Thr Asn Ile Pro Phe
            820                 825                 830

<210> SEQ ID NO 42
<211> LENGTH: 829
<212> TYPE: PRT
<213> ORGANISM: Artificial sequence
<220> FEATURE:
<223> OTHER INFORMATION: Modified heterocyclase MicroD_R16_5GA

<400> SEQUENCE: 42

Met Ser His His His His His His Asp Tyr Asp Glu Asn Leu Tyr Phe
1               5                   10                  15

Gln Gly Ser Arg Leu Thr Ala Gly Gln Leu Ser Ser Gln Leu Ala Glu
            20                  25                  30

Leu Ser Glu Glu Ala Leu Gly Asp Ala Gly Ala Gly Ala Gly Ala Gly
        35                  40                  45

Ala Gly Ala Lys Leu Met Gln Ser Thr Pro Leu Leu Gln Ile Gln Pro
    50                  55                  60

His Phe His Val Glu Val Ile Glu Pro Lys Gln Val Tyr Leu Leu Gly
65                  70                  75                  80

Glu Gln Ala Asn Tyr Ala Leu Thr Gly Gln Leu Tyr Cys Gln Ile Leu
                85                  90                  95

Pro Leu Leu Asp Gly Gln His Ser Arg Glu Gln Ile Val Glu Lys Leu
            100                 105                 110

Asp Gly Glu Val Pro Ser Glu Tyr Ile Asp Tyr Val Leu Asp Arg Leu
        115                 120                 125

Ala Glu Lys Gly Tyr Leu Thr Glu Ala Ala Pro Glu Leu Ser Ser Glu
    130                 135                 140

Val Ala Ala Phe Trp Ser Glu Leu Gly Ile Ala Pro Pro Val Ala Ala
145                 150                 155                 160

Glu Ala Leu Arg Gln Ser Val Thr Leu Thr Pro Val Gly Asn Ile Ser
                165                 170                 175

Glu Val Thr Val Ala Ala Leu Thr Thr Ala Leu Arg Asp Ile Gly Ile
            180                 185                 190
```

-continued

Ser Val Gln Thr Pro Thr Glu Ala Gly Ser Pro Thr Ala Leu Asn Val
    195                 200                 205

Val Leu Thr Asp Asp Tyr Leu Gln Pro Glu Leu Ala Lys Ile Asn Lys
210                 215                 220

Gln Ala Leu Glu Ser Gln Gln Thr Trp Leu Leu Val Lys Pro Val Gly
225                 230                 235                 240

Ser Val Leu Trp Leu Gly Pro Val Phe Val Pro Gly Lys Thr Gly Cys
            245                 250                 255

Trp Asp Cys Leu Ala His Arg Leu Arg Gly Asn Arg Glu Val Glu Ala
        260                 265                 270

Ser Val Leu Gln Gln Lys Gln Ala Gln Gln Arg Asn Gly Gln Ser
    275                 280                 285

Gly Ser Val Ile Gly Cys Leu Pro Thr Ala Arg Ala Thr Leu Pro Ser
    290                 295                 300

Thr Leu Gln Thr Gly Leu Gln Phe Ala Ala Thr Glu Ile Ala Lys Trp
305                 310                 315                 320

Ile Val Lys His His Val Lys Ala Thr Ala Pro Gly Thr Val Phe Phe
            325                 330                 335

Pro Thr Leu Asp Gly Lys Ile Ile Thr Phe Asn His Thr Val Ile Asp
        340                 345                 350

Leu Lys Ser His Val Leu Val Arg Arg Ser Gln Cys Pro Ser Cys Gly
    355                 360                 365

Asp Arg Gln Ile Leu His Arg Gln Gly Phe Glu Pro Val Lys Leu Val
    370                 375                 380

Ser Arg Arg Lys His Phe Thr His Asp Gly Gly His Arg Ala Phe Thr
385                 390                 395                 400

Pro Glu Gln Thr Val Gln Lys Tyr Gln His Leu Val Ser Pro Ile Thr
            405                 410                 415

Gly Val Val Thr Glu Leu Val Arg Leu Thr Asp Pro Ala Asn Pro Leu
        420                 425                 430

Val His Thr Tyr Lys Ala Gly His Ala Phe Gly Ser Ala Thr Thr Leu
    435                 440                 445

Arg Gly Leu Arg Asn Thr Leu Lys Tyr Lys Ser Ser Gly Lys Gly Lys
    450                 455                 460

Thr Asp Ile Gln Ser Arg Ala Ser Gly Leu Cys Glu Ala Ile Glu Arg
465                 470                 475                 480

Tyr Ser Gly Ile Phe Gln Gly Asp Glu Pro Arg Lys Arg Ala Thr Leu
            485                 490                 495

Ala Glu Leu Gly Asp Leu Ala Leu His Pro Glu Ser Leu Leu Tyr Phe
        500                 505                 510

Ser Asn Thr Gln Tyr Ala Asn Arg Glu Glu Leu Asn Ala Gln Gly Ser
    515                 520                 525

Ala Ala Ala Tyr Arg Trp Ile Pro Asn Arg Phe Asp Val Ser Gln Ala
    530                 535                 540

Ile Asp Trp Thr Pro Val Trp Ser Leu Thr Glu Gln Lys His Lys Tyr
545                 550                 555                 560

Val Pro Thr Ala Phe Cys Tyr Tyr Gly Tyr Pro Leu Pro Glu Glu Gln
            565                 570                 575

Arg Phe Cys Lys Ala Asp Ser Asn Gly Asn Ala Ala Gly Asn Thr Leu
        580                 585                 590

Glu Glu Ala Ile Leu Gln Gly Phe Leu Glu Leu Val Glu Arg Asp Ser
    595                 600                 605

Ile Ala Met Trp Trp Tyr Asn Arg Ile Arg Arg Pro Ala Val Asp Leu
610                 615                 620

Ser Thr Phe Asp Glu Pro Tyr Phe Val Asp Leu Gln Gln Phe Tyr Gln
625                 630                 635                 640

Gln Gln Asn Arg Glu Leu Trp Val Leu Asp Val Thr Ala Asp Leu Gly
            645                 650                 655

Ile Pro Ala Phe Ala Gly Phe Ser Arg Arg Thr Val Gly Thr Ser Glu
        660                 665                 670

Arg Ile Ser Ile Gly Phe Gly Ala His Leu Asp Pro Thr Ile Ala Ile
    675                 680                 685

Leu Arg Ala Leu Thr Glu Val Ser Gln Val Gly Leu Glu Leu Asp Lys
690                 695                 700

Ile Pro Asp Asp Lys Leu Asp Gly Glu Ser Lys Asp Trp Met Leu Asn
705                 710                 715                 720

Val Thr Val Glu Asn His Pro Trp Leu Ala Pro Asp Pro Ser Val Pro
            725                 730                 735

Met Lys Thr Ala Ser Asp Tyr Pro Lys Arg Trp Ser Asp Ile His
        740                 745                 750

Thr Asp Val Met Asn Cys Val Lys Thr Ala Gln Thr Ala Gly Leu Glu
    755                 760                 765

Val Met Val Leu Asp Gln Thr Arg Pro Asp Ile Gly Leu Asn Val Val
770                 775                 780

Lys Val Ile Ile Pro Gly Met Arg Thr Phe Trp Thr Arg Phe Gly Gln
785                 790                 795                 800

Gly Arg Leu Tyr Asp Ile Pro Val Lys Leu Gly Trp Leu Asp Ala Pro
            805                 810                 815

Leu Ala Glu Glu Glu Leu Asn Gln Thr Asn Ile Pro Phe
        820                 825

<210> SEQ ID NO 43
<211> LENGTH: 834
<212> TYPE: PRT
<213> ORGANISM: Artificial sequence
<220> FEATURE:
<223> OTHER INFORMATION: Modified heterocyclase MicroD_R16_GLEAS_5GA

<400> SEQUENCE: 43

Met Ser His His His His His His Asp Tyr Asp Glu Asn Leu Tyr Phe
1               5                   10                  15

Gln Gly Ser Arg Leu Thr Ala Gly Gln Leu Ser Ser Gln Leu Ala Glu
            20                  25                  30

Leu Ser Glu Glu Ala Leu Gly Asp Ala Gly Leu Glu Ala Ser Gly Ala
        35                  40                  45

Gly Ala Gly Ala Gly Ala Gly Ala Lys Leu Met Gln Ser Thr Pro Leu
    50                  55                  60

Leu Gln Ile Gln Pro His Phe His Val Glu Val Ile Glu Pro Lys Gln
65                  70                  75                  80

Val Tyr Leu Leu Gly Glu Gln Ala Asn Tyr Ala Leu Thr Gly Gln Leu
                85                  90                  95

Tyr Cys Gln Ile Leu Pro Leu Leu Asp Gly Gln His Ser Arg Glu Gln
            100                 105                 110

Ile Val Glu Lys Leu Asp Gly Glu Val Pro Ser Glu Tyr Ile Asp Tyr
        115                 120                 125

Val Leu Asp Arg Leu Ala Glu Lys Gly Tyr Leu Thr Glu Ala Ala Pro
    130                 135                 140

```
Glu Leu Ser Ser Glu Val Ala Ala Phe Trp Ser Glu Leu Gly Ile Ala
145                 150                 155                 160

Pro Pro Val Ala Ala Glu Ala Leu Arg Gln Ser Val Thr Leu Thr Pro
                165                 170                 175

Val Gly Asn Ile Ser Glu Val Thr Val Ala Ala Leu Thr Thr Ala Leu
                180                 185                 190

Arg Asp Ile Gly Ile Ser Val Gln Thr Pro Thr Glu Ala Gly Ser Pro
                195                 200                 205

Thr Ala Leu Asn Val Val Leu Thr Asp Asp Tyr Leu Gln Pro Glu Leu
        210                 215                 220

Ala Lys Ile Asn Lys Gln Ala Leu Glu Ser Gln Gln Thr Trp Leu Leu
225                 230                 235                 240

Val Lys Pro Val Gly Ser Val Leu Trp Leu Gly Pro Val Phe Val Pro
                245                 250                 255

Gly Lys Thr Gly Cys Trp Asp Cys Leu Ala His Arg Leu Arg Gly Asn
                260                 265                 270

Arg Glu Val Glu Ala Ser Val Leu Gln Gln Lys Gln Ala Gln Gln Gln
                275                 280                 285

Arg Asn Gly Gln Ser Gly Ser Val Ile Gly Cys Leu Pro Thr Ala Arg
        290                 295                 300

Ala Thr Leu Pro Ser Thr Leu Gln Thr Gly Leu Gln Phe Ala Ala Thr
305                 310                 315                 320

Glu Ile Ala Lys Trp Ile Val Lys His His Val Lys Ala Thr Ala Pro
                325                 330                 335

Gly Thr Val Phe Phe Pro Thr Leu Asp Gly Lys Ile Ile Thr Phe Asn
                340                 345                 350

His Thr Val Ile Asp Leu Lys Ser His Val Leu Val Arg Arg Ser Gln
        355                 360                 365

Cys Pro Ser Cys Gly Asp Arg Gln Ile Leu His Arg Gln Gly Phe Glu
        370                 375                 380

Pro Val Lys Leu Val Ser Arg Arg Lys His Phe Thr His Asp Gly Gly
385                 390                 395                 400

His Arg Ala Phe Thr Pro Glu Gln Thr Val Gln Lys Tyr Gln His Leu
                405                 410                 415

Val Ser Pro Ile Thr Gly Val Val Thr Glu Leu Val Arg Leu Thr Asp
                420                 425                 430

Pro Ala Asn Pro Leu Val His Thr Tyr Lys Ala Gly His Ala Phe Gly
            435                 440                 445

Ser Ala Thr Thr Leu Arg Gly Leu Arg Asn Thr Leu Lys Tyr Lys Ser
450                 455                 460

Ser Gly Lys Gly Lys Thr Asp Ile Gln Ser Arg Ala Ser Gly Leu Cys
465                 470                 475                 480

Glu Ala Ile Glu Arg Tyr Ser Gly Ile Phe Gln Gly Asp Glu Pro Arg
                485                 490                 495

Lys Arg Ala Thr Leu Ala Glu Leu Gly Asp Leu Ala Leu His Pro Glu
            500                 505                 510

Ser Leu Leu Tyr Phe Ser Asn Thr Gln Tyr Ala Asn Arg Glu Glu Leu
            515                 520                 525

Asn Ala Gln Gly Ser Ala Ala Tyr Arg Trp Ile Pro Asn Arg Phe
        530                 535                 540

Asp Val Ser Gln Ala Ile Asp Trp Thr Pro Val Trp Ser Leu Thr Glu
545                 550                 555                 560

Gln Lys His Lys Tyr Val Pro Thr Ala Phe Cys Tyr Tyr Gly Tyr Pro
```

565                 570                 575

Leu Pro Glu Glu Gln Arg Phe Cys Lys Ala Asp Ser Asn Gly Asn Ala
            580                 585                 590

Ala Gly Asn Thr Leu Glu Glu Ala Ile Leu Gln Gly Phe Leu Glu Leu
        595                 600                 605

Val Glu Arg Asp Ser Ile Ala Met Trp Trp Tyr Asn Arg Ile Arg Arg
610                 615                 620

Pro Ala Val Asp Leu Ser Thr Phe Asp Glu Pro Tyr Phe Val Asp Leu
625                 630                 635                 640

Gln Gln Phe Tyr Gln Gln Asn Arg Glu Leu Trp Val Leu Asp Val
                645                 650                 655

Thr Ala Asp Leu Gly Ile Pro Ala Phe Ala Gly Phe Ser Arg Arg Thr
            660                 665                 670

Val Gly Thr Ser Glu Arg Ile Ser Ile Gly Phe Gly Ala His Leu Asp
        675                 680                 685

Pro Thr Ile Ala Ile Leu Arg Ala Leu Thr Glu Val Ser Gln Val Gly
    690                 695                 700

Leu Glu Leu Asp Lys Ile Pro Asp Lys Leu Asp Gly Glu Ser Lys
705                 710                 715                 720

Asp Trp Met Leu Asn Val Thr Val Glu Asn His Pro Trp Leu Ala Pro
                725                 730                 735

Asp Pro Ser Val Pro Met Lys Thr Ala Ser Asp Tyr Pro Lys Arg Trp
            740                 745                 750

Ser Asp Asp Ile His Thr Asp Val Met Asn Cys Val Lys Thr Ala Gln
        755                 760                 765

Thr Ala Gly Leu Glu Val Met Val Leu Asp Gln Thr Arg Pro Asp Ile
    770                 775                 780

Gly Leu Asn Val Val Lys Val Ile Pro Gly Met Arg Thr Phe Trp
785                 790                 795                 800

Thr Arg Phe Gly Gln Gly Arg Leu Tyr Asp Ile Pro Val Lys Leu Gly
                805                 810                 815

Trp Leu Asp Ala Pro Leu Ala Glu Glu Glu Leu Asn Gln Thr Asn Ile
            820                 825                 830

Pro Phe

<210> SEQ ID NO 44
<211> LENGTH: 832
<212> TYPE: PRT
<213> ORGANISM: Artificial sequence
<220> FEATURE:
<223> OTHER INFORMATION: Modified heterocyclase PatD_Q21_5GA

<400> SEQUENCE: 44

Met Ser His His His His His His Asp Tyr Asp Glu Asn Leu Tyr Phe
1               5                   10                  15

Gln Gly Ser Gln Leu Ser Ser Gln Leu Ala Glu Leu Ser Glu Glu Ala
            20                  25                  30

Leu Gly Asp Ala Gly Ala Gly Ala Gly Ala Gly Ala Lys Leu
        35                  40                  45

Met Gln Pro Thr Ala Leu Gln Ile Lys Pro His Phe His Val Glu Ile
    50                  55                  60

Ile Glu Pro Lys Gln Val Tyr Leu Leu Gly Glu Gln Gly Asn His Ala
65                  70                  75                  80

Leu Thr Gly Gln Leu Tyr Cys Gln Ile Leu Pro Phe Leu Asn Gly Glu
                85                  90                  95

-continued

```
Tyr Thr Arg Glu Gln Ile Val Glu Lys Leu Asp Gly Gln Val Pro Glu
            100                 105                 110

Glu Tyr Ile Asp Phe Val Leu Ser Arg Leu Val Glu Lys Gly Tyr Leu
        115                 120                 125

Thr Glu Val Ala Pro Glu Leu Ser Leu Glu Val Ala Ala Phe Trp Ser
    130                 135                 140

Glu Leu Gly Ile Ala Pro Ser Val Val Ala Glu Gly Leu Lys Gln Pro
145                 150                 155                 160

Val Thr Val Thr Thr Ala Gly Lys Gly Ile Arg Glu Gly Ile Val Ala
                165                 170                 175

Asn Leu Ala Ala Ala Leu Glu Glu Ala Gly Ile Gln Val Ser Asp Pro
            180                 185                 190

Lys Ala Pro Lys Ala Pro Lys Ala Gly Asp Ser Thr Ala Gln Leu Gln
        195                 200                 205

Val Val Leu Thr Asp Asp Tyr Leu Gln Pro Glu Leu Ala Ala Ile Asn
    210                 215                 220

Lys Glu Ala Leu Glu Arg Gln Gln Pro Trp Leu Val Lys Pro Val
225                 230                 235                 240

Gly Ser Ile Leu Trp Leu Gly Pro Leu Phe Val Pro Gly Glu Thr Gly
                245                 250                 255

Cys Trp His Cys Leu Ala Gln Arg Leu Arg Gly Asn Arg Glu Val Glu
            260                 265                 270

Ala Ser Val Leu Gln Gln Lys Arg Ala Leu Gln Glu Arg Asn Gly Gln
        275                 280                 285

Asn Lys Asn Gly Ala Val Ser Cys Leu Pro Thr Ala Arg Ala Thr Leu
290                 295                 300

Pro Ser Thr Leu Gln Thr Gly Leu Gln Trp Ala Ala Thr Glu Ile Ala
305                 310                 315                 320

Lys Trp Met Val Lys Arg His Leu Asn Ala Ile Ala Pro Gly Thr Ala
                325                 330                 335

Arg Phe Pro Thr Leu Ala Gly Lys Ile Phe Thr Phe Asn Gln Thr Thr
            340                 345                 350

Leu Glu Leu Lys Ala His Pro Leu Ser Arg Arg Pro Gln Cys Pro Thr
        355                 360                 365

Cys Gly Asp Gln Glu Ile Leu Gln Arg Arg Gly Phe Glu Pro Leu Lys
    370                 375                 380

Leu Glu Ser Arg Pro Lys His Phe Thr Ser Asp Gly Gly His Arg Ala
385                 390                 395                 400

Thr Thr Pro Glu Gln Thr Val Gln Lys Tyr Gln His Leu Ile Gly Pro
                405                 410                 415

Ile Thr Gly Val Val Thr Glu Leu Val Arg Ile Ser Asp Pro Ala Asn
            420                 425                 430

Pro Leu Val His Thr Tyr Arg Ala Gly His Ser Phe Gly Ser Ser Ala
        435                 440                 445

Gly Ser Leu Arg Gly Leu Arg Asn Thr Leu Arg Tyr Lys Ser Ser Gly
    450                 455                 460

Lys Gly Lys Thr Asp Ser Gln Ser Arg Ala Ser Gly Leu Cys Glu Ala
465                 470                 475                 480

Ile Glu Arg Tyr Ser Gly Ile Phe Leu Gly Asp Glu Pro Arg Lys Arg
                485                 490                 495

Ala Thr Leu Ala Glu Leu Gly Asp Leu Ala Ile His Pro Glu Gln Cys
            500                 505                 510
```

Leu His Phe Ser Asp Arg Gln Tyr Asp Asn Arg Asp Ala Leu Asn Ala
            515                 520                 525

Glu Gly Ser Ala Ala Tyr Arg Trp Ile Pro His Arg Phe Ala Ala
530                 535                 540

Ser Gln Ala Ile Asp Trp Thr Pro Leu Trp Ser Leu Thr Glu Gln Lys
545                 550                 555                 560

His Lys Tyr Val Pro Thr Ala Ile Cys Tyr Tyr Asn Tyr Leu Leu Pro
                565                 570                 575

Pro Ala Asp Arg Phe Cys Lys Ala Asp Ser Asn Gly Asn Ala Ala Gly
            580                 585                 590

Asn Ser Leu Glu Glu Ala Ile Leu Gln Gly Phe Met Glu Leu Val Glu
        595                 600                 605

Arg Asp Ser Val Ala Leu Trp Trp Tyr Asn Arg Leu Arg Arg Pro Glu
    610                 615                 620

Val Glu Leu Ser Ser Phe Glu Glu Pro Tyr Phe Leu Gln Leu Gln Gln
625                 630                 635                 640

Phe Tyr Arg Ser Gln Asn Arg Glu Leu Trp Val Leu Asp Leu Thr Ala
                645                 650                 655

Asp Leu Gly Ile Pro Ala Phe Ala Gly Leu Ser Arg Arg Thr Val Gly
            660                 665                 670

Ser Ser Glu Arg Val Ser Ile Gly Phe Gly Ala His Leu Asp Pro Lys
        675                 680                 685

Ile Ala Ile Leu Arg Ala Leu Thr Glu Val Ser Gln Val Gly Leu Glu
    690                 695                 700

Leu Asp Lys Val Pro Asp Glu Lys Leu Asp Gly Glu Ser Lys Asp Trp
705                 710                 715                 720

Met Leu Glu Val Thr Leu Glu Thr His Pro Cys Leu Ala Pro Asp Pro
                725                 730                 735

Ser Gln Pro Arg Lys Thr Ala Asn Asp Tyr Pro Lys Arg Trp Ser Asp
            740                 745                 750

Asp Ile Tyr Thr Asp Val Met Ala Cys Val Glu Met Ala Lys Val Ala
        755                 760                 765

Gly Leu Glu Thr Leu Val Leu Asp Gln Thr Arg Pro Asp Ile Gly Leu
    770                 775                 780

Asn Val Val Lys Val Met Ile Pro Gly Met Arg Thr Phe Trp Ser Arg
785                 790                 795                 800

Tyr Gly Pro Gly Arg Leu Tyr Asp Val Pro Val Gln Leu Gly Trp Leu
                805                 810                 815

Lys Glu Pro Leu Ala Glu Ala Glu Met Asn Pro Thr Asn Ile Pro Phe
            820                 825                 830

<210> SEQ ID NO 45
<211> LENGTH: 836
<212> TYPE: PRT
<213> ORGANISM: Artificial sequence
<220> FEATURE:
<223> OTHER INFORMATION: Modified heterocyclase PatD_Q21_7GA

<400> SEQUENCE: 45

Met Ser His His His His His His Asp Tyr Asp Glu Asn Leu Tyr Phe
1               5                   10                  15

Gln Gly Ser Gln Leu Ser Ser Gln Leu Ala Glu Leu Ser Glu Glu Ala
            20                  25                  30

Leu Gly Asp Ala Gly Ala Gly Ala Gly Ala Gly Ala Gly Ala Gly Ala
        35                  40                  45

```
Gly Ala Lys Leu Met Gln Pro Thr Ala Leu Gln Ile Lys Pro His Phe
 50                  55                  60

His Val Glu Ile Ile Glu Pro Lys Gln Val Tyr Leu Leu Gly Glu Gln
 65                  70                  75                  80

Gly Asn His Ala Leu Thr Gly Gln Leu Tyr Cys Gln Ile Leu Pro Phe
                 85                  90                  95

Leu Asn Gly Glu Tyr Thr Arg Glu Gln Ile Val Glu Lys Leu Asp Gly
            100                 105                 110

Gln Val Pro Glu Glu Tyr Ile Asp Phe Val Leu Ser Arg Leu Val Glu
        115                 120                 125

Lys Gly Tyr Leu Thr Glu Val Ala Pro Glu Leu Ser Leu Glu Val Ala
    130                 135                 140

Ala Phe Trp Ser Glu Leu Gly Ile Ala Pro Ser Val Val Ala Glu Gly
145                 150                 155                 160

Leu Lys Gln Pro Val Thr Val Thr Thr Ala Gly Lys Gly Ile Arg Glu
                165                 170                 175

Gly Ile Val Ala Asn Leu Ala Ala Leu Glu Glu Ala Gly Ile Gln
            180                 185                 190

Val Ser Asp Pro Lys Ala Pro Lys Ala Pro Lys Ala Gly Asp Ser Thr
        195                 200                 205

Ala Gln Leu Gln Val Val Leu Thr Asp Asp Tyr Leu Gln Pro Glu Leu
    210                 215                 220

Ala Ala Ile Asn Lys Glu Ala Leu Glu Arg Gln Gln Pro Trp Leu Leu
225                 230                 235                 240

Val Lys Pro Val Gly Ser Ile Leu Trp Leu Gly Pro Leu Phe Val Pro
                245                 250                 255

Gly Glu Thr Gly Cys Trp His Cys Leu Ala Gln Arg Leu Arg Gly Asn
            260                 265                 270

Arg Glu Val Glu Ala Ser Val Leu Gln Gln Lys Arg Ala Leu Gln Glu
        275                 280                 285

Arg Asn Gly Gln Asn Lys Asn Gly Ala Val Ser Cys Leu Pro Thr Ala
    290                 295                 300

Arg Ala Thr Leu Pro Ser Thr Leu Gln Thr Gly Leu Gln Trp Ala Ala
305                 310                 315                 320

Thr Glu Ile Ala Lys Trp Met Val Lys Arg His Leu Asn Ala Ile Ala
                325                 330                 335

Pro Gly Thr Ala Arg Phe Pro Thr Leu Ala Gly Lys Ile Phe Thr Phe
            340                 345                 350

Asn Gln Thr Thr Leu Glu Leu Lys Ala His Pro Leu Ser Arg Arg Pro
        355                 360                 365

Gln Cys Pro Thr Cys Gly Asp Gln Glu Ile Leu Gln Arg Arg Gly Phe
    370                 375                 380

Glu Pro Leu Lys Leu Glu Ser Arg Pro Lys His Phe Thr Ser Asp Gly
385                 390                 395                 400

Gly His Arg Ala Thr Thr Pro Glu Gln Thr Val Gln Lys Tyr Gln His
                405                 410                 415

Leu Ile Gly Pro Ile Thr Gly Val Val Thr Glu Leu Val Arg Ile Ser
            420                 425                 430

Asp Pro Ala Asn Pro Leu Val His Thr Tyr Arg Ala Gly His Ser Phe
        435                 440                 445

Gly Ser Ser Ala Gly Ser Leu Arg Gly Leu Arg Asn Thr Leu Arg Tyr
    450                 455                 460

Lys Ser Ser Gly Lys Gly Lys Thr Asp Ser Gln Ser Arg Ala Ser Gly
```

```
            465                 470                 475                 480
Leu Cys Glu Ala Ile Glu Arg Tyr Ser Gly Ile Phe Leu Gly Asp Glu
                    485                 490                 495
Pro Arg Lys Arg Ala Thr Leu Ala Glu Leu Gly Asp Leu Ala Ile His
                500                 505                 510
Pro Glu Gln Cys Leu His Phe Ser Asp Arg Gln Tyr Asp Asn Arg Asp
            515                 520                 525
Ala Leu Asn Ala Glu Gly Ser Ala Ala Tyr Arg Trp Ile Pro His
        530                 535                 540
Arg Phe Ala Ala Ser Gln Ala Ile Asp Trp Thr Pro Leu Trp Ser Leu
545                 550                 555                 560
Thr Glu Gln Lys His Lys Tyr Val Pro Thr Ala Ile Cys Tyr Tyr Asn
                565                 570                 575
Tyr Leu Leu Pro Pro Ala Asp Arg Phe Cys Lys Ala Asp Ser Asn Gly
            580                 585                 590
Asn Ala Ala Gly Asn Ser Leu Glu Glu Ala Ile Leu Gln Gly Phe Met
        595                 600                 605
Glu Leu Val Glu Arg Asp Ser Val Ala Leu Trp Trp Tyr Asn Arg Leu
    610                 615                 620
Arg Arg Pro Glu Val Glu Leu Ser Ser Phe Glu Glu Pro Tyr Phe Leu
625                 630                 635                 640
Gln Leu Gln Gln Phe Tyr Arg Ser Gln Asn Arg Glu Leu Trp Val Leu
                645                 650                 655
Asp Leu Thr Ala Asp Leu Gly Ile Pro Ala Phe Ala Gly Leu Ser Arg
            660                 665                 670
Arg Thr Val Gly Ser Ser Glu Arg Val Ser Ile Gly Phe Gly Ala His
        675                 680                 685
Leu Asp Pro Lys Ile Ala Ile Leu Arg Ala Leu Thr Glu Val Ser Gln
    690                 695                 700
Val Gly Leu Glu Leu Asp Lys Val Pro Asp Glu Lys Leu Asp Gly Glu
705                 710                 715                 720
Ser Lys Asp Trp Met Leu Glu Val Thr Leu Glu Thr His Pro Cys Leu
                725                 730                 735
Ala Pro Asp Pro Ser Gln Pro Arg Lys Thr Ala Asn Asp Tyr Pro Lys
            740                 745                 750
Arg Trp Ser Asp Ile Tyr Thr Asp Val Met Ala Cys Val Glu Met
        755                 760                 765
Ala Lys Val Ala Gly Leu Glu Thr Leu Val Leu Asp Gln Thr Arg Pro
    770                 775                 780
Asp Ile Gly Leu Asn Val Val Lys Val Met Ile Pro Gly Met Arg Thr
785                 790                 795                 800
Phe Trp Ser Arg Tyr Gly Pro Gly Arg Leu Tyr Asp Val Pro Val Gln
                805                 810                 815
Leu Gly Trp Leu Lys Glu Pro Leu Ala Glu Ala Glu Met Asn Pro Thr
            820                 825                 830
Asn Ile Pro Phe
        835

<210> SEQ ID NO 46
<211> LENGTH: 12
<212> TYPE: PRT
<213> ORGANISM: Prochloron sp.

<400> SEQUENCE: 46
```

```
Ile Thr Ala Cys Ile Thr Phe Cys Ala Tyr Asp Gly
1               5                   10
```

<210> SEQ ID NO 47
<211> LENGTH: 13
<212> TYPE: PRT
<213> ORGANISM: Artificial sequence
<220> FEATURE:
<223> OTHER INFORMATION: Synthetic substrate peptide

<400> SEQUENCE: 47

```
Ile Thr Ala Cys Ile Thr Ala Cys Ala Tyr Asp Gly Glu
1               5                   10
```

<210> SEQ ID NO 48
<211> LENGTH: 10
<212> TYPE: PRT
<213> ORGANISM: Artificial sequence
<220> FEATURE:
<223> OTHER INFORMATION: Synthetic sequence: Tag sequence

<400> SEQUENCE: 48

```
Met Arg Gly Ser His His His His His His
1               5                   10
```

<210> SEQ ID NO 49
<211> LENGTH: 8
<212> TYPE: PRT
<213> ORGANISM: Artificial sequence
<220> FEATURE:
<223> OTHER INFORMATION: Synthetic sequence: FLAG tag sequence

<400> SEQUENCE: 49

```
Asp Tyr Lys Asp Asp Asp Asp Lys
1               5
```

<210> SEQ ID NO 50
<211> LENGTH: 15
<212> TYPE: PRT
<213> ORGANISM: Artificial sequence
<220> FEATURE:
<223> OTHER INFORMATION: Synthetic sequence: Tag sequence

<400> SEQUENCE: 50

```
Lys Glu Thr Ala Ala Ala Lys Phe Glu Arg Gln His Met Asp Ser
1               5                   10                  15
```

<210> SEQ ID NO 51
<211> LENGTH: 8
<212> TYPE: PRT
<213> ORGANISM: Artificial sequence
<220> FEATURE:
<223> OTHER INFORMATION: Synthetic sequence: Strept-tag II sequence

<400> SEQUENCE: 51

```
Trp Ser His Pro Gln Phe Glu Lys
1               5
```

<210> SEQ ID NO 52
<211> LENGTH: 10
<212> TYPE: PRT
<213> ORGANISM: Artificial sequence
<220> FEATURE:
<223> OTHER INFORMATION: Synthetic sequence: c-myc tag sequence

<400> SEQUENCE: 52

Glu Gln Lys Leu Ile Ser Glu Glu Asp Leu

```
1               5                   10
```

<210> SEQ ID NO 53
<211> LENGTH: 12
<212> TYPE: PRT
<213> ORGANISM: Artificial sequence
<220> FEATURE:
<223> OTHER INFORMATION: Synthetic sequence: Cruz tag 09 sequence

<400> SEQUENCE: 53

```
Met Lys Ala Glu Phe Arg Arg Gln Glu Ser Asp Arg
1               5                   10
```

<210> SEQ ID NO 54
<211> LENGTH: 12
<212> TYPE: PRT
<213> ORGANISM: Artificial sequence
<220> FEATURE:
<223> OTHER INFORMATION: Synthetic sequence: Cruz tag 22 sequence

<400> SEQUENCE: 54

```
Met Arg Asp Ala Leu Asp Arg Leu Asp Arg Leu Ala
1               5                   10
```

<210> SEQ ID NO 55
<211> LENGTH: 7
<212> TYPE: PRT
<213> ORGANISM: Artificial sequence
<220> FEATURE:
<223> OTHER INFORMATION: Synthetic site-specific protease cleavage site

<400> SEQUENCE: 55

```
Glu Asn Leu Tyr Phe Gln Gly
1               5
```

<210> SEQ ID NO 56
<211> LENGTH: 7
<212> TYPE: PRT
<213> ORGANISM: Artificial sequence
<220> FEATURE:
<223> OTHER INFORMATION: Synthetic site-specific protease cleavage site

<400> SEQUENCE: 56

```
Glu Asn Leu Tyr Phe Gln Ser
1               5
```

<210> SEQ ID NO 57
<211> LENGTH: 6
<212> TYPE: PRT
<213> ORGANISM: Artificial sequence
<220> FEATURE:
<223> OTHER INFORMATION: Synthetic site-specific protease cleavage site

<400> SEQUENCE: 57

```
Glu Asn Leu Tyr Phe Gln
1               5
```

<210> SEQ ID NO 58
<211> LENGTH: 6
<212> TYPE: PRT
<213> ORGANISM: Artificial sequence
<220> FEATURE:
<223> OTHER INFORMATION: Synthetic site-specific protease cleavage site

<400> SEQUENCE: 58

```
Leu Val Pro Arg Gly Ser
1               5
```

```
<210> SEQ ID NO 59
<211> LENGTH: 4
<212> TYPE: PRT
<213> ORGANISM: Artificial sequence
<220> FEATURE:
<223> OTHER INFORMATION: Synthetic site-specific protease cleavage site

<400> SEQUENCE: 59

Ile Glu Gly Arg
1

<210> SEQ ID NO 60
<211> LENGTH: 4
<212> TYPE: PRT
<213> ORGANISM: Artificial sequence
<220> FEATURE:
<223> OTHER INFORMATION: Synthetic site-specific protease cleavage site

<400> SEQUENCE: 60

Ile Asp Gly Arg
1

<210> SEQ ID NO 61
<211> LENGTH: 8
<212> TYPE: PRT
<213> ORGANISM: Artificial Sequence
<220> FEATURE:
<223> OTHER INFORMATION: PatE  substrate (core sequence)

<400> SEQUENCE: 61

Ile Thr Val Cys Ile Ser Val Cys
1               5
```

MODIFIED HETEROCYCLASE

FIELD

This invention relates to heterocyclase enzymes, in particular heterocyclase enzymes engineered to alter their substrate specificity, and the use of such enzymes in the in vitro and in vivo synthesis of modified peptides.

BACKGROUND

There has been a surge in interest in the ocean as a source of new therapeutics {Blunt et al., 2012, Nat Prod Rep, 29, 144-222}. This has in part been stimulated by high profile successes and by belief that the less well-explored marine environment contains many more unexploited resources {Driggers et al., 2008, Nat Rev Drug Discov, 7, 608-24; Mayer et al., 2013, Mar Drugs, 11, 2510-73}. Ribosomally synthesized and post-translationally modified peptides (RiPPs) produced by marine organisms have been shown to possess anti-tumour, anti-fungal, antibacterial and antiviral properties {Sivonen et al., 2010, Appl Microbiol Biotechnol, 86, 1213-25}. Cyanobactins, peptide derived natural products from cyanobacteria, are RiPPs in which one or more core peptides (it is the core peptide which becomes a natural product) are embedded into a larger precursor peptide. The most well-known example of this class are the patellamides, whose biosynthetic pathway was one of the first cyanobactin pathways to be described and cloned {Schmidt et al., 2005, Proc Natl Acad Sci USA, 102, 7315-20; Donia et al., 2006, Nat Chem Biol, 2, 729-35; Long et al., 2005, Chembiochem, 6, 1760-5}. The precursor peptide has an N-terminal leader, typically around 40 residues, which is disposed of during maturation {Arnison et al., 2013, Nat Prod Rep, 30, 108-60}. Characterized modifications of the core peptide are extensive and include heterocyclization of Ser/Thr and Cys residues to oxazolines and thiazolines, oxidation of these heterocycles to oxazoles and thiazoles, epimerization of amino acids to give D-stereocenters, Ser/Thr/Tyr prenylation and macrocycle formation {Milne et al., 2006, Org Biomol Chem, 4, 631-8; Schmidt et al., 2005, Proc Natl Acad Sci USA, 102, 7315-20; Schmidt and Donia, 2009, Methods Enzymol, 458, 575-96}. The permissiveness of the modifying enzymes to sequence changes in the core peptide has been demonstrated by the creation of large libraries of novel macrocycles made in vivo by genetic engineering {Donia et al., 2006, Nat Chem Biol, 2, 729-35; Donia and Schmidt, 2011, Chem Biol, 18, 508-19}. Of the enzymes, which have been structurally and biochemically characterized, three, the protease (which cleaves off the leader), the heterocyclase and macrocyclase, recognize regions outside the core peptide to accomplish their transformations {Houssen et al., 2012, Chembiochem, 13, 2683-9; Koehnke et al., 2012, Nat Struct Mol Biol, 19, 767-72; Koehnke et al., 2013, Chembiochem, 14, 564-7; Koehnke et al., 2013, Angew Chem Int Ed Engl, 52, 13991-6; Agarwal et al., 2012, Chem Biol, 19, 1411-22}. The recognition beyond the functional group that governs the prenylase {Bent et al., 2013, Acta Crystallogr Sect F Struct Biol Cryst Commun, 69, 618-23; Majmudar and Gibbs, 2011, Chembiochem, 12, 2723-6}, oxidase {Melby et al., 2014, Biochemistry, 53, 413-22} and hypothetical epimerase remain unknown.

The first chemical transformation in the biosynthesis of the patellamides is the heterocyclization of core peptide Cys (and sometimes Ser/Thr) residues to thiazolines (and oxazolines) {McIntosh and Schmidt, 2010, Chembiochem, 11, 1413-21}. The site-selective introduction of heterocycles into peptide backbones alters both conformation and reactivity of peptides; this tailoring of peptides is highly desirable in modifying their biological properties {Nielsen et al., 2014, Angew Chem Int Ed Engl}. This step is carried out by a conserved class of ATP and $Mg^{2+}$-dependent YcaO-domain containing heterocyclases, exemplified by the enzymes PatD and TruD from the patellamide and trunkamide pathways, respectively {McIntosh and Schmidt, 2010, Chembiochem, 11, 1413-21; McIntosh et al., 2010, J Am Chem Soc, 132, 4089-91}.

The recognition elements that control the substrate processing was not known although the N-terminal leader of substrate peptides is required for processing by TruD/PatD {McIntosh and Schmidt, 2010, Chembiochem, 11, 1413-21; McIntosh et al., 2010, J Am Chem Soc, 132, 4089-91} but no molecular insight has been forthcoming. The apo structure of the cyanobactin heterocyclase TruD was reported and showed this enzyme to be a three-domain protein {Koehnke et al., 2013, Angew Chem Int Ed Engl, 52, 13991-6}. The first two domains share structural but limited sequence homology with MccB (an adenylating enzyme from the microcin pathway) {Regni et al., 2009, EMBO J, 28, 1953-64} and the third domain (the 'YcaO' domain) had, at that time, no homology to known structures {Koehnke et al., 2013, Angew Chem Int Ed Engl, 52, 13991-6}.

Analysis of both the BalhD and TruD heterocyclases has shown they operate with a preferred order, starting at the C-terminus {Melby et al., 2012, J Am Chem Soc, 134, 5309-16; Koehnke et al., 2013, Angew Chem Int Ed Engl, 52, 13991-6}. By a series of deletions and site directed mutants of and within the PatE leader peptide the substrate recognition motif was narrowed (denoted 'minimal leader') {Koehnke et al., 2013, Angew Chem Int Ed Engl, 52, 13991-6}. It was also shown that TruD was able to process the C-terminal cysteine of test peptides which lacked the leader, albeit more slowly, but TruD was not, within the timescale of the experiment, able to process a second 'internal' cysteine {Koehnke et al., 2013, Angew Chem Int Ed Engl, 52, 13991-6}. A recent study has reported that trans activation of the PatD enzyme by exogenous leader peptide restored processing activity for internal cysteines {Goto et al., 2014, Chem Biol, 21, 766-74}.

WO2014136971 reports the production of compounds containing heterocyclic rings using heterocyclases linked to leader sequences. However, the reaction is inefficient and generates multiple products containing different numbers of heterocyclic residues.

SUMMARY

The present inventors have engineered a leader-independent heterocyclase (also known as a cyclodehydratase) which produces a homogeneous heterocyclic product by efficiently introducing multiple heterocyclic groups into a target molecule that lacks a peptidyl leader sequence. This avoids the need for laborious purification of individual heterocyclic species and has significant potential in both biotechnology and chemical synthesis.

An aspect of the invention provides a modified heterocyclase which comprises a cyanobactin leader sequence and a heterocyclase sequence.

The cyanobactin leader sequence may consist of the amino acid sequence of SEQ ID NO: 29 or SEQ ID NO: 30, more preferably the amino acid sequence of SEQ ID NO: 31, for example the amino acid sequence of SEQ ID NO: 32.

The modified heterocyclase introduces heterocyclic groups into a target molecule which completely lacks a cyanobactin leader sequence. For example, the modified heterocyclase may convert heterocyclisable groups in the target molecule into heterocyclic residues. The target molecule is efficiently heterocyclised to produce a homogenous product in which all of the heterocyclisable groups are replaced by heterocyclic residues (i.e. a single fully heterocyclised species).

The heterocyclase sequence may be a leader-dependent heterocyclase sequence.

The heterocyclase sequence may comprise the substrate binding and catalytic domains of a leader-dependent heterocyclase or the substrate binding domain of a bipartite leader-dependent heterocyclase.

Another aspect of the invention provides a method of introducing heterocyclic residues into a target molecule comprising;
 treating a target peptide comprising one or more heterocyclisable residues with a modified heterocyclase as described herein.

Another aspect of the invention provides the use of a modified heterocyclase as described herein in a method of introducing heterocyclic residues into a target molecule.

Another aspect of the invention provides a kit comprising a modified heterocyclase as described herein.

The kit may further comprise a target molecule comprising one or more residues that are heterocyclisable by the modified heterocyclase.

BRIEF DESCRIPTION OF FIGURES

FIG. 11 shows Table 1, in which statistics of data collection and refinement are summarized.

FIG. 12 shows Table 2, in which data (nucleotide $K_d$ (μM) and number of heterocycles (PatE')) for various enzymes are summarized.

FIG. 13 and FIG. 14 show Table 3 and Table 4, respectively, in which data of LynD / PatE'interaction affinities for a number of mutants of LynD are summarized.

DETAILED DESCRIPTION

Figure 1:
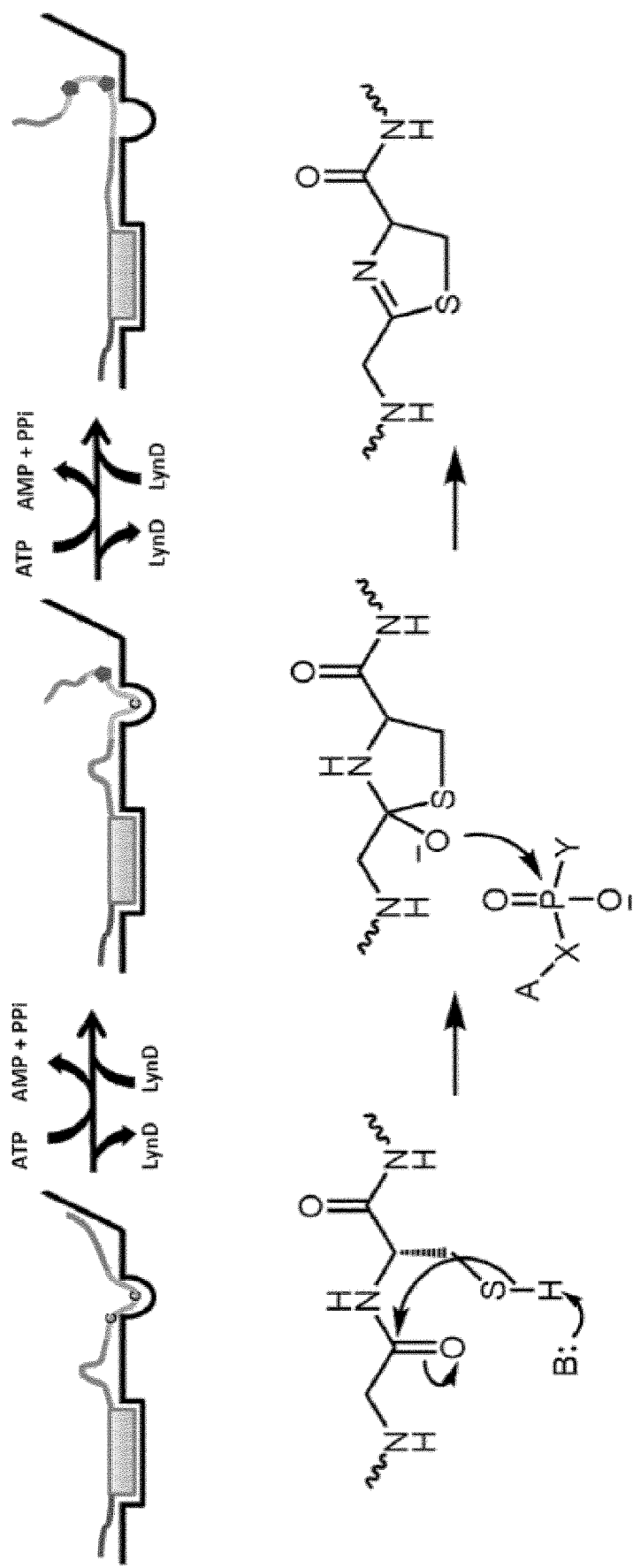
FIG. 1 shows a cartoon schematic summarizing the processing of PatE precursor peptide by the ATP-dependent heterocyclase enzyme LynD, highlighting the defined order of heterocyclization

The present inventors have performed structural analysis of the binding of the leader sequence of a peptide substrate to leader-dependent heterocyclases and have recognised that the fusion of a minimal leader sequence to a leader-dependent heterocyclase provides a modified heterocyclase that is not only permanently locked in an active conformation, but also operates on substrates which lack a leader peptide to produce efficient heterocyclization of the heterocyclisable residues in the substrate. This yields reaction product in which all or substantially all of the substrate is fully heterocyclized (i.e. all of the residues in the substrate that are capable of being heterocyclised by the heterocyclase are heterocyclized). The ability to generate a homogeneous synthetic substrate comprising heterocyclic residues offers significant advantages in biotechnology and chemical synthesis applications.

Modified heterocyclases described herein may be useful in installing heterocycles into molecules, such as peptides and other biomolecules without the need for leader peptides.

Preferably, the modified heterocyclase displays the same or greater activity on a minimal target molecule as the wild-type heterocyclase on wild-type substrate peptide.

Modified heterocyclases described herein may be useful in the production of a broad range of molecules containing heterocycles, including linear and cyclic peptides and peptide analogues.

A modified heterocyclase as described herein introduces heterocyclic groups into heterocyclisable residues in a target molecule that lacks a leader peptide. The modified heterocyclase may heterocyclise all of the heterocyclisable residues in the target molecule.

For example, the modified heterocyclase may heterocyclise one, two, three, four, five or six or more heterocyclisable residues in the target molecule. Preferably, at least two residues are heterocyclised in the target molecule.

Heterocyclisable residues may include naturally occurring and non-naturally occurring amino acids such as cysteine, homocysteine, selenocysteine, tellurocysteine, threonine, serine, homoserine, 2, 3-diaminopropanoic acid, 2,4-diaminobutanoic acid, and synthetic derivatives thereof with additional R groups at the alpha, beta and/or gamma positions. Heterocyclisable amino acids may be converted into residues comprising 5 membered heterocyclic rings (for example rings containing C=N and S, O, N and/or Se) by the modified heterocyclase. In some embodiments, amino acids with elongated beta-side chains, such as homocysteine and homoserine, may be converted into residues comprising 6 membered heterocyclic rings. Preferred heterocyclisable residues include cysteine, threonine and serine.

For example, cysteine residues may be converted into thiazoline residues, selenocysteines may be converted into selenazoline residues, serine residues may be converted into oxazoline residues, threonine residues may be converted into oxazoline residues, and/or 2,3 diaminopropanoic acid residues may be converted into imadazoline residues by a modified heterocyclase described herein. Homocysteine, homoserine, 2, 4-diaminobutanoic acid and alpha/beta/gamma substituted analogues thereof may be converted into 5,6-dihydro-4H-1,3-thiazine, 5,6-dihydro-4H-1,3-oxazine and 5,6-dihydro-4H-1λ2-pyrimidine respectively by a modified heterocyclase described herein.

Different cyanobacterial heterocyclases introduce heterocycles in different amino acids, so the amino acids in the target molecule that are heterocyclisable by a heterocyclase depend on which heterocyclase is employed. A heterocyclisable residue is a residue in the target molecule that the heterocyclase sequence in the modified heterocyclase is capable of converting into a heterocyclic residue. For example, modified heterocyclases comprising PatD or MicD may be used to heterocyclise Se-Cys, Cys, Thr and Ser residues in the target molecule and modified heterocyclases comprising LynD or TruD may be used to heterocyclise Cys or Se-Cys residues in the target molecule but not Thr or Ser residues. Different patterns of heterocyclic residues may therefore be produced in the same target molecule through the use of different heterocyclase sequences.

The residues that are heterocyclised by the modified heterocyclase may be located at any position in the target molecule other than the C terminal. The C terminal residue of target molecule, which contains a free carboxyl group, is not heterocyclisable. The C terminal of the target molecule may comprise the sequence $HtX_n$, where Ht is a heterocyclisable residue, X is any amino acid and n is 1-10. For example, residues that are heterocyclised may be adjacent to a cyclisation signal, if present, and/or located at other positions within the target peptide (i.e. internal residues). Preferably, the modified heterocyclase heterocyclises all of the residues in the target molecule that are potentially targetted by that heterocyclase.

The modified heterocyclase comprises a heterocyclase sequence linked to a cyanobactin leader sequence.

Preferably, the cyanobactin leader sequence is fused or covalently linked to the N terminal of the heterocyclase sequence.

The heterocyclase sequence may be a leader-sequence dependent heterocyclase sequence i.e. a heterocyclase sequence that comprises a leader-binding domain and heterocyclises residues in a substrate peptide that comprises an N-terminal leader sequence. Suitable leader dependent heterocyclase sequences are well-known in the art and include bacterial, for example cyanobacterial, heterocyclase sequences.

The heterocyclase sequence may comprise the leader binding domain of a bacterial, more preferably, a cyanobacterial heterocyclase sequence. For example, the heterocyclase sequence may comprise the leader binding domain (domain 1) of LynD (residues 1 to 109 of SEQ ID NO: 1), PatD (residues 1 to 108 of SEQ ID NO: 2), TruD (residues 1 to 108 of SEQ ID NO: 3), MicD (residues 1 to 109 of SEQ ID NO: 4) or TenD (residues 1 to 109 of SEQ ID NO: 5 or the leader binding domain of an amino acid sequence shown in Table 5 or a variant of any one of these sequences. The leader binding domain may be identified in a bacterial heterocyclase using standard sequence analysis techniques.

In some embodiments, the heterocyclase sequence may comprise the leader binding domain of a bipartite heterocyclase in which the leader binding domain and catalytic domain are separate polypeptides. The modified heterocyclase may form an active heterocyclase in the presence of the catalytic domain of the bipartite heterocyclase. Bipartite heterocyclases include BalhC/D. For example, the heterocyclase sequence may comprise the amino acid sequence of SEQ ID NO: 6 (*B. thuringiensis*), SEQ ID NO: 7 (*B cereus*) or a variant of any one of these sequences. The catalytic domain of the bipartite heterocyclase may comprise the amino acid sequence of SEQ ID NO: 8 (*B. thuringiensis*), SEQ ID NO: 9 (*B cereus*) or a variant of any one of these sequences.

In other embodiments, the heterocyclase sequence may comprise the substrate binding and catalytic domains of a heterocyclase.

A preferred heterocyclase sequence for use in a modified heterocyclase may comprise the sequence AAG $X_1$ $X_2$ $X_3$E $X_4$A $X_5$LQG $X_6$$X_7$E $X_8$ $X_9$ ERD $X_{10}$ $X_{11}$, (SEQ ID NO: 10) where $X_1$ is N or T; $X_2$ is T, C or S; $X_3$ is L or I; $X_3$ is F, L, I or M; $X_4$ is E or D; $X_5$ is I or V; $X_6$ is F or L; $X_7$ is M, L or F; $X_8$ is L or V; $X_9$ is V or I; $X_{10}$ is S, A, or C; and $X_{11}$ is V or I. For example, a suitable heterocyclase sequence may comprise the sequence AAGNTLEEAILQGFMEL-VERDSV (SEQ ID NO: 11) or a variant thereof.

A preferred heterocyclase sequence for use in a modified heterocyclase may further comprise the sequence $X_1$S$X_2$$X_3$$X_4$E$X_5$$X_6$ERY$X_7$$X_8$$X_9$$X_{10}$$X_{11}$G$X_{12}$E (SEQ ID NO: 12); where $X_1$ is A, V or M; $X_2$ is G or A; $X_3$ is L or I; $X_3$ is L, V or F; $X_4$ is C or G; $X_5$ is A or S; $X_6$ is I, V or L; $X_7$ is S or A, $X_8$ is G or F; $X_9$ is I, L, T or V; $X_{10}$ is F or Y and $X_{11}$ is Q, E, T or L; $X_{12}$ is D, Y, E or N. For example, a heterocyclase sequence may comprise the sequence ASGLCEAIERYSGIFQGDE (SEQ ID NO: 13) or a variant thereof.

In some embodiments, the heterocyclase sequence may comprise the amino acid sequence of LynD (SEQ ID NO: 1), PatD (SEQ ID NO: 2), TruD (SEQ ID NO: 3), MicD (SEQ ID NO: 4) or TenD (SEQ ID NO: 5), an amino acid sequence shown in Table 5 or a variant of one of these sequences.

Other suitable heterocyclases may be identified using standard sequence analysis techniques.

The cyanobactin leader sequence may be a fragment of a cyanobactin precursor peptide leader sequence or a variant thereof. The cyanobactin precursor peptide leader sequence is the amino acid sequence that is located at the N terminal end of the core cyanobactin peptide sequence. Examples of cyanobactin precursor peptide leader sequences are highlighted in SEQ ID NOS: 18-27. Other cyanobactin precursor peptide leader sequences are well known in the art.

A heterocyclase comprising a cyanobactin leader sequence which consists of a defined sequence from a cyanobactin precursor peptide leader sequence may be devoid of additional residues that are contiguous with the defined sequence in the cyanobactin precursor peptide leader sequence.

Preferably, the N terminal residue of the cyanobactin leader sequence corresponds to any one of residues 16 to 21 of the cyanobactin precursor peptide leader sequence. For example, the N terminal residue of the cyanobactin leader sequence may be any one of R16, L17, T18, A19, G20 or Q21 of any one of SEQ ID NOs: 18 to 21; or the corresponding residue in a different cyanobactin precursor peptide leader sequence.

The cyanobactin leader sequence may consist of 8 to 40 amino acids, preferably 18 to 23 amino acid residues or 15 to 20 amino acid residues.

The cyanobactin leader sequence may be from the same source (e.g. the same bacteria species) as the heterocyclase sequence or may be from a different source. For example, the cyanobactin leader sequence may be a fragment of the pre-pro-peptide that forms the natural substrate for the heterocyclase.

A cyanobactin leader sequence for use as described herein may comprise the sequence LAEL $X_1EEX_2X_3$ (SEQ ID NO: 14) where $X_1$ is S or T, preferably S, $X_2$ is A, V, T or N and $X_3$ is L or I. Suitable leader sequences may comprise LAELSEEAL, LAELSEETL or LAELSEEAI (SEQ ID NOs 15 to 17) or a variant of any one of these sequences. For example, a cyanobactin leader sequence may comprise residues 26 to 34 of any one of SEQ ID NOs: 18-27.

Preferred cyanobactin leader sequences for use in a modified heterocyclase may consist of the sequence $X_4X_5X_6X_7X_8$ LAEL $X_1EEX_2X_3LX_9X_{10}X_{11}X_{12}$ (SEQ ID NO: 29) where $X_1$ is S or T, preferably S; $X_2$ is A, V, T or N; $X_3$ is L or I or optionally absent; $X_4$ is T, Q or K; $X_5$ is Q, L or K; $X_6$ is A, P or S; $X_7$ is A, D or S; $X_8$ is E, L, A, H or Q or Y; $X_9$ is G or A, preferably G; $X_{10}$ is S, D, G, or absent; $X_{11}$ is T, L, N, A or V or absent; and $X_{12}$ is T, P, A, E, G, D or absent.

Other preferred cyanobactin leader sequences for use in a modified heterocyclase may consist of the sequence $X_{17}X_{16}X_{15}X_{14}X_{13}X_4X_5X_6X_7X_8LAELX_1EEX_2X_3LX_9X_{10}X_{11}X_{12}$ (SEQ ID NO: 30), where $X_1$ is S or T, preferably S; $X_2$ is A, V, T or N; $X_3$ is L, I or absent; $X_4$ is T, Q or K; $X_5$ is Q, L or K; $X_6$ is A, P or S; $X_7$ is A, D or S; $X_8$ is E, L, A, H or Q or Y; $X_9$ is G or A, preferably G; $X_{10}$ is S, D, G, or absent; $X_{11}$ is T, L, N, A or V or absent; $X_{12}$ is T, P, A, E, G, D or absent; $X_{13}$ is G or absent; $X_{14}$ is A, T, S, Q or absent; $X_{15}$ is T, I, P, S or absent; $X_{16}$ is L, I, T, G, or V or absent; and $X_7$ is R or absent.

For example, a cyanobactin leader sequence may consist of residues 21 to 36 of SEQ ID NOs: 18-23, residues 21 to 38 of SEQ ID NO: 24, residues 21-35 of SEQ ID NO: 25, or residues 21 to 36 of SEQ ID NOs: 26 or 27 or a variant of one of these sequences.

Preferably, the cyanobactin leader sequence consists of the amino acid sequence of SEQ ID NO: 31. Examples of suitable cyanobactin leader sequences include SEQ ID NOs: 32 to 37. In some preferred embodiments, the cyanobactin leader sequence consists of the sequence QLSSQLAEL-SEEALGDAG (SEQ ID NO: 32) or a variant thereof.

In other embodiments, for example in which the heterocyclase sequence is the substrate binding domain of a bipartite sequence such as SEQ ID NO: 6 or SEQ ID NO: 7, the cyanobactin leader sequence may consist of the amino acid sequence of SEQ ID NO: 32.

The cyanobactin leader sequence may be directly linked to the heterocyclase sequence or more preferably may be linked via a linker.

Suitable linkers are well-known in the art and include chemical and peptidyl linkers.

A peptidyl linker may comprise a sequence of amino acid residues, for example, 5 to 15 amino acid residues, preferably 9 to 12 amino acid residues, more preferably about 11 amino acid residues. Any linker sequence may be employed. Preferably the linker sequence is a heterologous sequence. Suitable linker amino acid sequences are well known in the art and may, for example, comprise GA repeats, such as the amino acid sequence AGAGAGAGAGA (SEQ ID NO: 38) or a variant thereof.

In some embodiments, one or more additional heterologous residues may be present between the cyanobactin leader sequence and the heterocyclase sequence. Additional heterologous residues may be introduced by the insertion of a restriction endonuclease cleavage site into the nucleic acid encoding the modified heterocyclase. For example, the amino acid sequence KL may be introduced between the linker and the heterocyclase sequence by the insertion of a Hind III site into the encoding nucleic acid An example of a modified heterocyclase as described herein may comprise the amino acid sequence of residues 19 to 823 of SEQ ID NO: 39, residues 19 to 824 of SEQ ID NO: 40, residues 19 to 832 of SEQ ID NO: 41, residues 19 to 829 of SEQ ID NO: 42, residues 19 to 834 of SEQ ID NO: 43, residues 19 to 832 of SEQ ID NO: 44, residues 19 to 836 of SEQ ID NO: 45 or a variant of any one of these sequences.

A heterocyclase, linker or modified heterocyclase sequence as described herein may comprise an amino acid sequence which is a variant or fragment of a reference amino acid sequence set out herein (e.g. a heterocyclase of SEQ ID NOs: 1 to 7 or shown in Table 5; a cyanobactin leader sequence of SEQ ID NOs: 14 to 38; or a modified heterocyclase of residues 19 to 823 of SEQ ID NO: 39, residues 19 to 824 of SEQ ID NO: 40, residues 19 to 832 of SEQ ID NO: 41, residues 19 to 829 of SEQ ID NO: 42, residues 19 to 834 of SEQ ID NO: 43, residues 19 to 832 of SEQ ID NO: 44 or residues 19 to 836 of SEQ ID NO: 45). Suitable variants include homologues and orthologues from other bacterial species.

A variant of a reference amino acid sequence may have an amino acid sequence having at least 20%, at least 25%, at least 30%, at least 40%, at least 50%, at least 60%, at least 65%, at least 70%, at least 75%, at least 80%, at least 85%, at least 90%, at least 95% or at least 98% sequence identity to the reference amino acid sequence.

Amino acid sequence identity is generally defined with reference to the algorithm GAP (GCG Wisconsin Package™, Accelrys, San Diego Calif.). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, psiBLAST or TBLASTN (which use the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), generally employing default parameters.

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, up to 15, up to 20, up to 30 or up to 40 residues may be inserted, deleted or substituted.

A fragment is a truncated sequence which contains less than the full-length amino acid sequence but which retains the activity of the full-length amino acid sequence. For example, a fragment of a heterocyclase sequence may comprise at least 100 amino acids, at least 200 amino acids or at least 300 contiguous amino acids from the full-length heterocyclase sequence. A cyanobactin leader sequence may comprise at least 18 amino acids from the full-length cyanobactin precursor peptide leader sequence.

A heterologous element is an element which is not associated or linked to the subject feature in its natural environment i.e. association with a heterologous element is artificial and the element is only associated or linked to the subject feature through human intervention.

One or more heterologous amino acids, for example a heterologous peptide or heterologous polypeptide sequence, may be joined, linked or fused to a modified heterocyclase set out herein. The one or more heterologous amino acids may include amino acid sequences from a non-cyanobacterial source.

For example, the modified heterocyclase may be expressed as a fusion protein with a purification tag. Following expression of the fusion protein comprising the modified heterocyclase, the fusion protein may be isolated using the purification tag, for example, by affinity chromatography using an immobilised agent which binds to the purification tag.

The purification tag is a heterologous amino acid sequence which forms one member of a specific binding pair. Polypeptides containing the purification tag may be detected, isolated and/or purified through the binding of the other member of the specific binding pair to the polypeptide. In some preferred embodiments, the tag sequence may form an epitope which is bound by an antibody molecule.

Various suitable purification tags are known in the art, including, for example, MRGS(H)$_6$, DYKDDDDK (FLAG™, SEQ ID NO:49), T7-, S-(KETAAAKFERQHMDS, SEQ ID NO:50), poly-Arg (R$_{5-6}$), poly-His (H$_{2-10}$), e.g. (H)$_6$, poly-Cys (C$_4$) poly-Phe(F$_{11}$) poly-Asp(D$_{5-16}$), Strept-tag II (WSHPQFEK, SEQ ID NO:51), c-myc (EQKLISEEDL, SEQ ID NO:52), Influenza-HA tag (Murray, P. J. et al (1995) *Anal Biochem* 229, 170-9), Glu-Giu-Phe tag (Stammers, D. K. et al (1991) *FEBS Lett* 283, 298-302), SUMO (Marblestone et al Protein Sci. 2006 January; 15(1): 182-189), Tag.100 (Qiagen; 12 aa tag derived from mammalian MAP kinase 2), Cruz tag 09™ (MKAEFRRQESDR (SEQ ID NO:53), Santa Cruz Biotechnology Inc.) and Cruz tag 22™ (MRDALDRLDRLA (SEQ ID NO:54), Santa Cruz Biotechnology Inc.), glutathione-S-transferase, Small Ubiquitin-like Modifier (SUMO) tag or His$_6$-SUMO. Known tag sequences are reviewed in Terpe (2003) Appl. Microbiol. Biotechnol. 60 523-533.

A site-specific protease cleavage site may be located between the modified heterocyclase sequence and the purification tag. Suitable site-specific protease cleavage sites are well known in the art and include ENLYFQ(G/S) or ENLYFQ for cleavage by Tobacco Etch Virus (TEV) protease; K or R residue for cleavage by trypsin; Y for cleavage by chymotrypsin; LVPRGS for cleavage by thrombin; and I(E/D)GR for cleavage by factor Xa. Other suitable site specific proteases are well-known in the art and any site specific endoprotease with a residue preference may be used.

Suitable site-specific proteases, such as TEV protease, trypsin, chymotrypsin and thrombin are well known in the art and are available from commercial sources.

After isolation, the fusion protein may then be proteolytically cleaved at the site-specific protease cleavage site to remove the purification tag and produce the isolated modified heterocyclase.

In some embodiments, modified heterocyclases described herein may form homodimers or heterodimers (e.g. bipartite heterocyclases) in solution or remain in monomeric form.

Other aspects of the invention provide an isolated nucleic acid encoding a modified heterocyclase as described above and a construct comprising a nucleic acid encoding a modified heterocyclase operably linked to a heterologous regulatory sequence.

Nucleic acids and constructs as described above may be comprised within an expression vector for the production of recombinant modified heterocyclase. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Suitable regulatory sequences to drive the expression of heterologous nucleic acid coding sequences in expression systems are well-known in the art and include constitutive promoters, for example viral promoters such as CMV or SV40, and inducible promoters, such as Tet-on controlled promoters. A vector may also comprise sequences, such as origins of replication and selectable markers, which allow for its selection and replication and expression in bacterial hosts such as *E. coli* and/or in eukaryotic cells.

Other aspects of the invention provide a vector comprising a nucleic acid that encodes a modified heterocyclase as described above and a cell comprising such a vector.

Vectors for use in expressing modified heterocyclase may be plasmids, viral e.g. 'phage, or phagemid, as appropriate. The precise choice of vector will depend on the particular expression system which is employed. Modified heterocyclase may be expressed in any convenient expression system, and numerous suitable systems are available in the art, including bacterial, yeast, insect or mammalian cell expression systems. For further details see, for example, *Molecular Cloning: a Laboratory Manual:* 3rd edition, Russell et al., 2001, Cold Spring Harbor Laboratory Press.

A method of producing a modified heterocyclase as described above may comprise expressing a nucleic acid encoding the modified heterocyclase in a host cell and isolating the modified heterocyclase following said expression.

Many known techniques and protocols for expression of recombinant polypeptides in cell culture and their subsequent isolation and purification are known in the art (see for example *Protocols in Molecular Biology*, Second Edition, Ausubel et al. eds. John Wiley & Sons, 1992; *Recombinant Gene Expression Protocols* Ed RS Tuan (March 1997) Humana Press Inc).

The modified heterocyclase may be expressed as a single fusion protein. In other embodiments, the cyanobactin leader sequence and heterocyclase sequence may be produced separately and then linked with a peptide or chemical linker.

In some embodiments, a modified heterocyclase may be immobilised on a solid support.

A solid support is an insoluble, non-gelatinous body which presents a surface on which the peptides or proteins can be immobilised. Examples of suitable supports include glass slides, microwells, membranes, or beads. The support may be in particulate or solid form, including for example a plate, a test tube, bead, a ball, filter, fabric, polymer or a membrane. A peptide or protein may, for example, be fixed to an inert polymer, a 96-well plate, other device, apparatus or material.

The immobilisation of peptides and proteins to the surface of solid supports is well-known in the art.

A target molecule suitable for treatment with a modified heterocyclase described above may comprise one or more heterocyclisable groups or residues.

As described above, heterocyclisable residues may include cysteine, homocysteine, selenocysteine, tellurocysteine, threonine, serine, homoserine, 2, 3-diaminopropanoic acid, 2,4-diaminobutanoic acid, and synthetic derivatives or analogues thereof with additional R groups at the alpha, beta and/or gamma positions.

The residues that are heterocyclised in a particular reaction will depend on the heterocyclase being employed as different heterocyclases heterocylise different residues.

The target molecule may comprise 1, 2, 3, 4, 5, 6, 7, 8 or more heterocyclisable residues for heterocyclization (Shinya, K. et al J. Am. Chem. Soc. 2001, 123, 1262-1263). A modified heterocyclase as described herein heterocyclizes all or substantially all of the heterocyclisable residues in the target molecule.

Suitable target molecules may include heterocyclisable amino acids, peptides, peptide analogues, fatty acids, sugars, nucleic acids and other biomolecules comprising heterocyclisable amino acids or amino acid analogues.

A target peptide may have at least 4, 5, 6, 7 or 8 amino acid residues and up to 11, 12, 13, 14, 15, 16, 17, 18, 19, 20, 21, 22, 23 or more residues. For example, a suitable target peptide may have from 4 to 23 residues, preferably 6 to 23, 6 to 20 or 6 to 15 residues.

The target peptide may include modified amino acids, unmodified amino acids, heterocyclic amino acids, non-heterocyclic amino acids, naturally occurring amino acids and/or non-naturally occurring amino acids and amino acid analogues.

The target peptide may comprise peptidyl and non-peptidyl linkages.

The target peptide sequence may be a naturally occurring peptide sequence, for example a natural cyanobactin or cyclotide sequence; or a synthetic or non-naturally occurring peptide sequence. Examples of suitable target peptide sequences, are well-known in the art and are described in for example in Houssen et al Angewandte (2014) 53 DOI: 10.1002/anie. 201408082; Houssen, W. E. & Jaspars, M. *Chembiochem* 11, 1803-1815 (2010); and Sivonen, K., et al (2010) *Applied Microbiology*, (86) 1213-1225).

The target peptide lacks a leader sequence i.e. the target protein may be devoid of the amino acid sequence that is naturally located N terminal of the core cyanobactin sequence in the cyanobactin pre-pro-peptide. For example, the target peptide may lack residues 26 to 34 of PatE more preferably residues 21 to 38 of PatE, or the corresponding residues of other cyanobactin pre-pro-peptides.

In preferred embodiments, the target protein is devoid of all additional N terminal sequences.

If a cyclic peptide comprising heterocyclic groups is to be produced, a cyclisation signal may be located at the C terminal of the target peptide. The cyclisation signal may be heterologous i.e. not naturally associated with the target peptide sequence. A cyclisation signal is the recognition site for the cyanobacterial macrocyclase and may be useful in macrocyclizing a target peptide after the introduction of heterocycles to produce a cyclic peptide. The sequence of the cyclisation signal in the target peptide may depend on the cyanobacterial macrocyclase being used. Typically, a cyclisation signal will comprise the sequence; small residue-bulky residue-acidic residue. Suitable cyclisation signals include AYD, AYE, SYD, AFD and FAG. For example, the cyclisation signal may be AYD, which allows the macrocyclization of the target peptide using a PatG macrocyclase. In some preferred embodiments, target peptide may comprise a cyclisation signal recognised by an engineered macrocyclase. For example, a target peptide may comprise the cyclisation signal AYR which is recognised by an engineered PatG with a K598D mutation, as described in WO2014/001822.

For the production of linear peptides comprising heterocyclic groups, the target peptide may lack a cyclisation signal.

The target peptide may comprise a purification tag at its C terminal. Suitable purification tags are described above.

The target peptide as described herein may be generated wholly or partly by chemical synthesis. For example, peptides and polypeptides may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof. Chemical synthesis of peptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A User's Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997).

Non-natural residues and non-peptidyl linkages may introduced into the target molecule using standard chemical synthesis techniques.

Alternatively, a target molecule described herein may be generated wholly or partly by recombinant techniques. For example, a nucleic acid encoding the target peptide as described herein may be expressed in a host cell and the expressed polypeptide isolated and/or purified from the cell culture.

Another aspect of the invention provides a method of introducing heterocyclic groups into a target molecule comprising;
treating a target molecule comprising one or more heterocyclisable residues with a modified heterocyclase.

Suitable target molecules and modified heterocyclases are described above.

Treatment of the target molecules with the modified heterocyclase introduces heterocyclic groups into the target molecule, thereby producing a target molecule containing one or more heterocyclic residues. Preferably, all of the heterocyclisable residues in the target molecule are converted into heterocyclic groups.

Suitable conditions for heterocyclization of residues in a target molecule are well-known in the art and described herein. For example, a target peptide may be treated with the modified heterocyclase in the presence of ATP and $Mg^{2+}$.

In some embodiments, a bipartite heterocyclase may be employed in which the substrate binding domain and a catalytic domain are separate polypeptides. A method of introducing heterocyclic groups into a target molecule may comprising;
treating a target molecule comprising one or more heterocyclisable residues with;
(i) a modified heterocyclase comprising a cyanobactin leader sequence and the substrate binding domain of a bipartite cyanobacterial heterocyclase, and
(ii) the catalytic domain of the bipartite cyanobacterial heterocyclase.

Bipartite heterocyclases may include BahlC/BahlD (see Koehnke et al Angew Chem Int Ed Engl. Dec. 23, 2013; 52(52): 13991-13996). For example, bipartite heterocyclase substrate binding domains may comprise SEQ ID NOs; 6 and 7 or variants thereof and bipartite heterocyclase substrate binding domains may comprise SEQ ID NOs; 6a and 7a or variants thereof.

In some embodiments, the target molecule may be immobilised, for example on a solid support, and the modified heterocyclase may be free in solution. This may be useful, for example in facilitating purification of the target molecule.

In other embodiments, the target molecule may be free in solution and the modified heterocyclase may be immobilised for example on a solid support, such as a bead. This may be useful, for example in facilitating re-cycling of the modified heterocyclase.

The target molecule undergoes efficient heterocyclization by the modified heterocyclase, such that all the heterocyclisable residues in the target molecule are converted into heterocyclic residues (i.e. fully heterocyclized).

Following heterocyclization by the modified heterocyclase, the fully heterocyclized target molecule is the predominant species of target molecule in the reaction products. For example, at least 80%, at least 90%, at least 95% or at least 98% of the target molecules following heterocyclization as described herein are fully heterocyclized. For example, a target molecule comprising two heterocyclic residues may be the predominant species of target molecule following the heterocyclization of a target molecule with two heterocyclisable residues; a target molecule comprising three heterocyclic residues may be the predominant species of target molecule following the heterocyclization of a target molecule with three heterocyclisable residues; a target molecule comprising four heterocyclic residues may be the predominant species of target molecule following the heterocyclization of a target molecule with four heterocyclisable residues; and a target molecule comprising five heterocyclic residues may be the predominant species of target molecule following the heterocyclization of a target molecule with five heterocyclisable residues.

A method of introducing heterocyclic groups into a target molecule may comprise treating a population of identical target molecules (i.e. a homogeneous or non-diverse population) comprising one or more heterocyclisable residues with a modified heterocyclase, such that all the heterocyclisable residues are converted into heterocyclic groups in at least 80%, at least 90%, at least 95% or at least 98% of the target molecules in the population.

In some embodiments, the amount of other species of target molecule in the reaction products (i.e. species that comprise one or more heterocyclisable residues that have not been heterocyclized) may be undetectable, for example by HPLC analysis.

In other embodiments, the reaction products may comprise residual amounts of other species of target molecule. For example, the reaction products may comprise residual amounts of a target molecule species with one heterocyclisable residue that has not been heterocyclized. Target molecule species with two or more heterocyclisable residues that have not been heterocyclized may be absent or undetectable in the reaction products.

In some embodiments, the homogenous product may be purified and/or isolated after heterocyclization. In other embodiments, no purification or isolation of the reaction product may be required after heterocyclization.

Following the introduction of heterocycles using a modified heterocyclase, the target molecule may be further modified as required. For example, one or more of the modifications may be introduced into the target molecule.

The target molecule may be chemically modified or modified using one or more enzymes, for example cyanobacterial enzymes.

The target molecule may be oxidised to oxidise the heterocyclic amino acids introduced into the target molecule. For example, the target molecule may be treated with a bacterial or cyanobacterial oxidase or a chemical oxidizing agent to oxidise thiazoline residues into thiazoles. Suitable cyanobacterial oxidases include PatG oxidase from *Prochloron* spp. Suitable bacterial oxidases are well known in the art and include BcerB oxidase from the thiazole/oxazole modified microcin cluster (Melby et al J. Am. Chem. Soc, 2012, 134, 5309). Suitable chemical oxidizing agents are well known in the art and include $MnO_2$.

The target molecule may be treated with an epimerase, such that one or more amino acids in the target molecule comprise D-stereocenters. Suitable epimerases include PoyD (Morinaka et al Angew Chem Int Ed Engl. (2014) August 4; 53(32):8503-7; AFS60640.1 GI: 406822305).

One or more serine, threonine or tyrosine residues in the target molecule may be prenylated and/or geranylated. For example, the target molecule may be treated with a cyanobacterial prenylase. Suitable cyanobacterial prenylases include PatF prenylase (GI: 62910842 AAY21155.1), TruF2 prenylase (GI: 167859100 ACA04493.1), and TruF1 (GI: 167859099 ACA04492.1).

The target molecule may subjected to further chemical modification, for example to incorporate additional chemical groups, for example by alkylation, azide-alkyne cycloaddition or other standard methods of chemical coupling.

The target molecule may be labelled with a detectable label. The detectable label may be any molecule, atom, ion or group which is detectable by a molecular imaging modality or other means. Suitable detectable labels may include metals, radioactive isotopes and radio-opaque agents (e.g. gallium, technetium, indium, strontium, iodine, barium, bromine and phosphorus-containing compounds), radiolucent agents, contrast agents and fluorescent dyes.

The target molecule may be treated to introduce disulphide bonds, for example by oxidation of sulfhydryl groups.

The target molecule may be macrocyclised to produce a cyclic molecule. For example, the target molecule may be treated with a cyanobacterial macrocyclase. In some embodiments, a target peptide may be macrocyclised to produce a cyclic peptide. Suitable macrocyclases include PatG macrocyclase (AAY21156.1 GI: 62910843) and TruG (GI: 167859101 ACA04494.1) from Prochloron. Other suitable cyanobacterial macrocyclases are available in the art (Lee, S. W. et al (2008) PNAS 105(15), 5879-5884). In some preferred embodiments, the macrocyclase may be a modified PatG macrocyclase described in WO2014/001822.

Suitable target peptides for macrocyclisation comprise a cyclisation signal at their C terminal, as described above.

The target molecule may be conjugated to an antibody or other specific binding molecule or a ligand for binding to a receptor.

The target molecule may be attached to a solid support, such as a bead.

The methods of the invention are suitable for the production of usable amounts of fully heterocyclized target molecules. Following production as described above, the heterocyclized target molecule may be isolated and/or purified and used as required. Alternatively, the heterocyclized target molecule may be used without further isolation or purification. Target molecules produced as described herein, such as peptides or other biomolecules, may be useful in therapeutics, nanotechnology applications and in optical/electronic or contractile materials.

Another aspect of the invention provides a kit for the introduction of heterocyclic groups into a target peptide comprising;
 a modified heterocyclase as described above, or
 a nucleic acid encoding a modified heterocyclase.

The kit may further comprise a target molecule.

Modified heterocyclases and target peptides are described above.

A kit may further comprise a cyanobacterial oxidase or a chemical oxidising agent.

A kit may further comprise a cyanobacterial macrocyclase, such as PatG, TruG or a homologue or variant thereof.

The kit may include instructions for use in a method of introducing heterocyclic groups into a target peptide as described above.

A kit may include one or more other reagents required for the method, such as buffer solutions, solid supports, and purification reagents.

A kit may include one or more articles for performance of the method, such as means for providing the test sample itself, including sample handling containers (such components generally being sterile).

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

Experiments Three crystal structures of the cyanobactin heterocyclase LynD (homologous to PatD and TruD) from the aestuaramide pathway (*Lyngbya* sp.) were produced in a series of co-complexes (LynD/AMP/PatE, LynD/ADP $PO_4^{3-}$/PatEC51A, LynD/β,γ-imido-ATP/PatEC51A). The structures confirm that LynD uses the same nucleotide-binding site in the third (YcaO) domain of LynD described in the *E. coli* YcaO structure {Dunbar et al., 2014, Nat Chem Biol, 10, 823-9}. New biochemical data point to a very unusual but unifying mechanism. The molecular basis of leader recognition by the enzyme has been elucidated, rationalizing cis/trans activation of the heterocyclase and the sequence of the 'minimal leader'. Based upon these insights, a novel LynD has been engineered. This enzyme no longer requires leader peptide for full activity and can process multiple cysteines in a test peptide that lacks the leader peptide. This new enzyme has significant potential in both biotechnology and chemical synthesis.

1. Materials and Methods 1.1 Protein Cloning, Expression and Purification

Codon optimized full-length LynD (*Lyngbya* sp. PCC 8106) with an N-terminal TEV protease-cleavable His$_6$-tag was purchased from DNA2.0 in the pJexpress411 plasmid. The protein was expressed in *Escherichia coli* BL21 (DE3) grown on auto-induction medium {Studier, 2005, Protein expression and purification, 41, 207-234} for 48 h at 20° C. Cells were harvested by centrifugation at 4,000×g, 4° C. for 15 min and re-suspended in lysis buffer (500 mM NaCl, 20 mM Tris pH 8.0, 20 mM imidazole and 3 mM R-mercaptoethanol (BME)) with the addition of complete EDTA-free protease inhibitor tablets (Roche) and 0.4 mg DNase g$^{-1}$ wet cells (Sigma). Cells were lysed by passage through a cell disruptor at 30 kPSI (Constant Systems Ltd) and the lysate was cleared by centrifugation at 40,000×g, 4° C. for 20 min. The cleared lysate was applied to a Nickel Sepharose 6 Fast Flow (GE Healthcare) column pre-washed with lysis buffer and protein eluted with 250 mM imidazole. The protein was then passed over a desalting column (Desalt 16/10, GE Healthcare) in 100 mM NaCl, 20 mM Tris pH 8.0, 20 mM imidazole, 3 mM BME. Tobacco etch virus (TEV) protease was added to the protein at a mass-to-mass ratio of 1:10 and the protein digested for 2 h at 20° C. to remove the His$_6$-tag. However, removal of the His$_6$-tag was not essential for activity and so less vigorous methods for purification may also be used. Digested protein was passed over a second Ni-column and the flow-through loaded onto a monoQ column (GE Healthcare) equilibrated in 100 mM NaCl, 20 mM Tris pH 8.0, 3 mM BME. Protein was eluted from the monoQ column through a linear NaCl gradient, eluting at 250 mM NaCl. Finally, the protein was subjected to size-exclusion chromatography (Superdex™ 200, GE Healthcare) in 150 mM NaCl, 10 mM HEPES pH 7.4, 1 mM TCEP, and concentrated to 8 mg mL$^{-1}$. Integrity and identity were confirmed by mass spectrometry.

PatE' was synthetically produced in the pBMS vector (a gift from H. Liu) with a C-terminal His$_6$-tag and expressed in *Escherichia coli* BL21 (DE3) cells grown in auto induction medium {Studier, 2005, Protein expression and purification, 41, 207-234} for 24 h at 30° C. where the protein was driven to inclusion bodies.

Cells were harvested by centrifugation at 4,000×g for 15 min at 4° C. Cells were re-suspended in urea lysis buffer (8 M urea, 150 mM NaCl, 20 mM Tris pH 8.0, 20 mM Imidazole and 3 mM β-mercaptoethanol (BME) and lysed by sonication at 15 microns (SoniPrep 150, MSE). The lysate was cleared by centrifugation at 40,000×g, 20° C. for 20 min followed by passage through a 0.45 μm filter. The cleared lysate was applied to a Ni-sepharose FF column (GE Healthcare) pre-washed with urea lysis buffer and protein eluted with 250 mM imidazole. The protein was then supplemented with 10 mM DTT and incubated at room temperature for 2 h before size-exclusion chromatography (Superdex™ 75, GE Healthcare) in 150 mM NaCl, 10 mM HEPES pH 7.4, 1 mM TCEP. Peak fractions were pooled and concentrated to 1 mM.

To generate full length leader peptide for trans activation studies the PatE' sequence was mutated at 4 positions: D2Y, K3E, K4E and R16E. This quadruple mutant (PatE'4) was expressed and purified as described for PatE', and subjected to heterocyclization tests to ensure normal processing. The mutations K3E, K4E, and R16E enable full-length leader to be retained following digestion of PatE'4 with trypsin (D2Y permits quantification of the leader peptide). PatE'4 was digested with 1/100 trypsin at 37° C., 300 rpm for 3 h, and subsequently applied to a Ni-sepharose FF column (GE Healthcare) equilibrated in 150 mM NaCl, 10 mM HEPES pH 7.4, 1 mM TCEP. The flow-through was collected, which was confirmed to contain full-length PatE'4 leader peptide by mass spectrometry, and concentrated to 1 mM.

LynD and PatE point mutants were produced using the Phusion® site-directed mutagenesis kit (Finnzymes) following the manufacturer's protocol. All mutant proteins were expressed and purified as above. LynD fusion enzyme was produced by adding residues 21-38 of the PatE leader and an eleven residue long linker to the N-terminus of LynD via PCR. The protein was expressed and purified as described for native LynD above.

1.2 Heterocyclization Reactions

For all heterocyclization reactions, 100 M PatE' (and variants,) was incubated with 2 μM enzyme in 150 mM NaCl, 10 mM HEPES pH 7.4, 1 mM TCEP, 5 mM ATP and 5 mM MgCl$_2$ for 16 h at 37° C. Samples were analyzed by ESI or MALDI MS (LCT, Micromass or 4800 MALDI TOF/TOF Analyzer, ABSciex). For cis trans activation studies, 100 μM ITACITFCAYDG synthetic test peptide (Peptide Protein Research Ltd) was reacted with 5 μM heterocyclase enzyme in the presence and absence of 5.5 μM LAELSEEAL synthetic peptide, or 5.5 μM full-length PatE'4 leader peptide. The reaction was carried out in 150 mM NaCl, 10 mM HEPES pH 7.4, 1 mM TCEP, 5 mM ATP and 5 mM MgCl$_2$ for 16 h at 37° C. and analyzed as above. Synthetic peptides were purchased from Peptide Protein Research Ltd.

To assess the relative rates of heterocyclization under various conditions, heterocyclization reactions were monitored at regular intervals using MALDI TOF MS. In each case, reactions of PatE' or ITACITFCAYDG synthetic peptide were prepared as described and incubated at 37° C. prior to addition of LynD allowing a 0 time-point to be recorded. Time points for each reaction were recorded as follows: For PatE' with LynD (standard conditions), PatE' with LynD in the presence of α-β-methelene ATP, and ITACITFCAYDG with LynD fusion, the reaction was monitored after 1, 5, 10, 15, 20, 30, 45, 60, 90, 120 and 180 minutes; For ITACITFCAYDG with LynD in the absence, and presence of either minimal leader LAELSEEAL peptide, or full length PatE'4 leader peptide, the reaction was monitored after 15, 30, 60, 120, 240 and 1440 minutes. Reactions were set up in triplicate, and each sample was analyzed by MALDI TOF MS in triplicate (9 spectra recorded in total for each reaction at each time point). For each time point, the total ion count for each species (0, 1 and 2 heterocycles) was recorded, averaged and the percentage of each species was calculated. The rate of each reaction relative to the wild-type reaction (PatE'+LynD) was determined. LC–MS of reaction mixtures was performed on a Waters LC-MS system (LCT mass spectrometer and 2795 HPLC) using a Waters MassPrep column (2.1×10 mm). Solvent B was 0.1% formic acid and Solvent A was MeCN containing 0.1% formic acid. Gradient 0-0.5 min 98% B, 0.5-2.5 min linear to 2% B, 2.5-4.5 min 2% B, 4.5-4.6 min linear to 98% B, 1.6-12 min 98% B at 0.05 ml min-1. The following conditions were used on the mass spectrometer: ESI+ve, capillary voltage 3.5 kV, cone voltage 40 V, mass range 500-2500 m/z, RF lens 500. The spectra were combined across the eluted protein peak and the charged ion series processed using Water's MaxEnt algorithm to give protein mass, using peak width at half height on the strongest peak in the ion envelope. The data was calibrated externally against horse heart myoglobin (16,951.5 Da).

MALDI MS was acquired using a 4800 MALDI TOF/TOF Analyzer (ABSciex, Foster City, Calif.) equipped with a Nd:YAG 355 nm laser in linear mode and calibrated using the [M+H]+ and [M+2H]2+ peaks of ubiquitin. The spot was analyzed in positive MS mode between 3000 and 10000 m/z, by averaging 1000 laser spots.

Fragmentation MS of the peptides were carried out on an ABSciex 5600 mass spectrometer with Eksigent nanoLC and ThermoScientific Aclaim Pepmap RSLC column 75 uM×150 mm. Trap and elute methodology was used with a 6 minute trap wash. Trapping solvent A was 98% water, 2% MeCN, 0.05% Trifluoroacetic acid. Gradient solvent A was 98% water, 2% MeCN, and 0.1% formic acid and gradient solvent B was 98% MeCN, 2% water, and 0.1% formic acid. Gradient 0-0.5 min 5% B, 0.5-5 min linear to 40% B, 5-6 min linear to 95% B, 6-9 min 95% B, 9-10 min linear to 2% B, hold at 2% B until 20 mins at 300 nl min-1, and 45° C. The following conditions were used on the mass spec: ESI+ve, 0.25 s MS accumulation and 0.15 s MSMS accumulation, collision energy of 45 V with rolling collision energy optimization applied. The data was calibrated externally prior to analysis with 8 peptides from a tryptic digest of 25 fmol μl-1 Beta-galactosidase.

MALDI mass spectrometry for the time course was carried out on an ABSciex 4800 MALDI TOF/TOF mass spectrometer. 0.5 μl of sample was co-spotted with 0.5 μl of matrix (10 mg ml-1 alpha cyano-4-hydroxycinnamic acid in 50% MeCN and 50% 0.1% TFA) and the sample left to dry. Spectra were collected over the range 500-4000 m/z (reflectron for peptides <4000 m/z) or 3000-10000 m/z (linear for peptides >4000 m/z) with 20 subspectra of 50 shots accumulated randomly across the spot. The data was calibrated externally prior to analysis with 6 peptides from ABSciex standard 6 peptide mix (PN 4465940) in reflectron or the [M+H]$^+$ and [M+2H]$^{2+}$ peaks of ubiquitin in linear.

1.3 Crystallization, Data Collection, and Crystallographic Analysis

Co-crystallization trials of LynD with various peptide and nucleotide substrates were set up at 7.5 mg ml$^{-1}$ LynD with a 1.1 molar excess of PatE' (or variants), 5 mM nucleotide and 3 mM MgCl$_2$. LynD crystals in complex with PatE'-C51A and ATP were obtained in 16% PEG 3350, 0.1 M Mg formate. The crystals were cryoprotected in 37% PEG 3350, 0.1 M Mg formate, 1 mM ATP and flash-cooled in liquid nitrogen. These crystals belonged to space group P2$_1$2$_1$2$_1$ with cell dimensions a=81.8 Å b=116.1 Å, c=183.5 Å. Diffraction data was collected at Diamond beamline I24 at 100 K and processed with Xia2 {Winter, 2009, Journal of Applied Crystallography, 43, 186-190}.

LynD crystals in complex with PatE and AMP were obtained in 13% (w/v) PEG 3350, 0.1 M Tris pH 8.5, 0.2 M CaCl$_2$ and 0.6% (w/v) myo-inositole. The crystals were cryoprotected in 35% PEG 4000, 0.2 M CaCl$_2$), 0.1 M Tris pH 8.5, 1 mM AMP and flash-cooled in liquid nitrogen. These crystals belonged to space group P2$_1$2$_1$2$_1$ with cell dimensions a=65.8 Å b=152.8 Å, c=182.8 Å. Diffraction data was collected at Diamond beamline I02 at 100 K and processed with Xia2 {Winter, 2009, Journal of Applied Crystallography, 43, 186-190}. LynD crystals in complex with PatE-C51A and β-γ-imido-ATP were obtained in 28% PEG 4000, 0.1 M Tris pH 8.9, 0.2 M LiSO$_4$. The crystals were cryoprotected in 40% PEG 4000, 0.1 M Tris pH 8.9, 5 mM β-γ-imido-ATP and flash-cooled in liquid nitrogen. These crystals belonged to space group P2$_1$2$_1$2$_1$ with cell dimensions a=65.9 Å b=152.9 Å, c=182.5 Å. Diffraction data was collected at ESRF beamline ID29 at 100 K and processed with Xia2 {Winter, 2009, Journal of Applied Crystallography, 43, 186-190}.

The structure of LynD in complex with PatE' and AMP was determined by molecular replacement using Phaser {McCoy et al., 2005, Acta Crystallographica Section D-Biological Crystallography, 61, 458-464; Storoni et al., 2004, Acta Crystallographica Section D-Biological Crystallography, 60, 432-438} with TruD as a search model (PDB: 4BS9). The partially refined structure was then used as a search model for the remaining structures. In each case, complete manual rebuilding was performed with COOT {Emsley and Cowtan, 2004, Acta Crystallographica Section D-Biological Crystallography, 60, 2126-2132} and refinement was performed using CCP4 REFMAC5 {Murshudov et al., 2011, Acta Crystallogr D Biol Crystallogr, 67, 355-67} and Phenix Refin e {Adams et al., 2004, Journal of Synchrotron Radiation, 11, 53-55}. The statistics of data collection and refinement are summarized in Table 1. All molecular graphics figures were generated with the program Pymol {DeLano, 2002, DeLano Scientific, San Carlos, Calif., USA}.

1.4 ITC Analysis of LynD (and Mutants) with Substrate Peptide, and Nucleotide.

ITC experiments were performed using a VP-ITC instrument (MicroCal) in heterocyclization reaction buffer (150 mM NaCl, 10 mM HEPES pH 7.4, 1 mM TCEP) supplemented with 5 mM MgCl$_2$. For substrate binding experiments a cell solution of 10 µM LynD (and mutants) and a syringe solution of 150 µM PatE' (and mutants) was prepared by diluting protein and peptide with the buffer used for dialysis. For nucleotide binding experiments, the cell concentration was increased to 20 µM, and the ATP/AMP concentration in the syringe solution was 300 µM. Substrate, and ATP experiments were performed at 20° C., and AMP experiments at 25° C. Cell and syringe solutions were degassed for 15 min at 18 and 23° C. Titration method was as follows: one injection of 2 µl followed by injections of 5 µl at 0.5 µl/min, with a delay of 4 min between every injection. The stirring speed was 307 rpm throughout. Raw data was processed using MicroCal Origin software, and the baseline was adjusted and the integrations limits were selected manually. Data was non-linearly fitted to the one-site model (Origin) setting the stoichiometry to 1.

Purification of pyrophosphate from heterocyclization reactions was achieved by passing the reaction mixture through a 5 kDa cut-off protein concentrator. The flow-through was applied to CaptoQ resin (GE Healthcare), washed with 15 column volumes dH$_2$O and pyrophosphate eluted with 1M Na acetate pH 7.0.

Accurate mass measurements were carried out on ABSciex 5600 mass spectrometer with nanospray source. Samples were diluted 50% with ACN and infused at 1 ul/min using the inbuilt syringe pump. Negative ionization spectra were collected from 60-400 m/z in MS mode. Masses 176.9 and 178.9 m/z were isolated in Q1, fragmented with collision energy 30V in Q2 and the fragments measured from 50-200 m/z on the TOF analyzer. The TOF was externally calibrated with a mixture of Periodate (190.8847 m/z) and sulphanilic acid (172.0074 m/z)

2. Results 2.1 Structure of LynD

Full-length LynD heterocyclase was expressed, purified and its ability to perform heterocyclization reactions with a precursor peptide PatE variant (denoted PatE') in the presence of ATP/Mg$^2$ (Table 4) confirmed as described previously {Koehnke et al., 2013, Angew Chem Int Ed Engl, 52, 13991-6}. PatE' is 64 amino acids long, has a full leader but possesses a single core peptide (ITACITFC) and C-terminal His$_6$-tag. LynD retention time in gel filtration suggested LynD was a dimer and diffraction quality crystals were only obtained when incubated with a nucleotide and PatE'. The same orthorhombic form (but different unit cells) with two monomers in the asymmetric unit was obtained for all three complexes (LynD/AMP/PatE' 2.86 Å, LynD/ATP/PatE'C51A 2.14 Å, LynD/β,γ-imido-ATP/PatEC51A 3.01 Å). The two protomers are composed of the same three domains and form the same antiparallel dimer by head-to-tail association of domains 1 and 2 with a large interface (buried surface area of ~3280 Å$^2$) first seen for TruD {Koehnke et al., 2013, Angew Chem Int Ed Engl, 52, 13991-6}. The structure of LynD/AMP/PatE was determined by molecular replacement using TruD (PDB 4BS9) as the search model and partly refined. This structure was used as a search model for the 2.14 Å data, a complete model was built and refined with these data and then molecular replaced into the lower resolution data. Full structural statistics are given in Table 1. PatE' binds to LynD in an identical fashion in all three structures and as the overall Cα rmsd between the structures was low (Cα rmsd of <1.06 over 1,400 residues) our discussion refers to the high resolution LynD/ATP/PatEC51A structure (only the nucleotide binding is discussed for the other two complexes). The ordered residues comprise 6-143, 151-229, 240-336, and 342-775 in chain A and 4-226, 240-336, and 343-775 in chain B. The missing residues are presumed to be disordered. A Zn$^{2+}$ ion seen in TruD is coordinated in the same manner (Koehnke et al., 2013, Angew Chem Int Ed Engl, 52, 13991-6).

2.2 Nucleotide Binding and Utilization

Domain 3 (residues 316-775) is structurally homologous to the *E. coli* YcaO domain (Dunbar et al., 2014, Nat Chem Biol, 10, 823-9) (Cα rmsd of 2.34 over 282 residues) and binds nucleotide in an identical location. In LynD, the adenosine ring N7 atom makes a hydrogen bond with the side chain of Q415 and the N1 atom with N536. The ring sits between a cation-π stacking interaction with R344 on one face and van der Waals interactions to C419 and T351 on the other. The lack of extensive hydrogen bond recognition of the ring is consistent with ability of these enzymes to use other nucleotide triphosphates {Koehnke et al., 2013, Angew Chem Int Ed Engl, 52, 13991-6}. The O2' and O3' atoms of the ribose molecule form hydrogen bonds with the main chain of A534 and the side chain of E426 whilst the α-phosphate makes a salt bridge with R636 and hydrogen bonds with Q544 and S419, very similar to the *E. coli* YcaO domain {Dunbar et al., 2014, Nat Chem Biol, 10, 823-9}. The recognition of the adenosine is subtly different in *E. coli* YcaO {Dunbar et al., 2014, Nat Chem Biol, 10, 823-9} as the adenosine ring has been built in a different conformer in this structure.

2.3 Substrate Recognition and Activation

Only residues 21-35 of PatE' are ordered in the structure: 021 to S23 adopt a coil, S24 to E28 adopt a helical turn, S30 to A33 adopt a β-strand conformation and L34 and G35 adopt a coil. The β-strand adds to the three-stranded antiparallel β-sheet in domain 1 of LynD, converting it to a four-stranded anti-parallel β-sheet. In addition to β-sheet hydrogen bonds the side chains of PatE E28 and E31 make both salt bridges and hydrogen bonds with LynD 047 (main chain), side chains of Y39 and R74. Both L26 and L29 of PatE' insert into hydrophobic pockets in Domain 1 of LynD. The interactions provide a structural rationale for the minimal leader (residues 26 to 34 of PatE) and site directed mutants previously reported {Koehnke et al., 2013, Angew Chem Int Ed Engl, 52, 13991-6}. LynD/PatE' interaction affinities were measured for a number of mutants of LynD (Tables 3 and 4). In the apo structure of TruD {Koehnke et al., 2013, Angew Chem Int Ed Engl, 52, 13991-6} residues 371-415 (LynD numbering) in Domain 3 were disordered but in LynD these are now ordered forming a strand turn helix strand motif that makes the entrance to and part of the nucleotide binding site. We suggest it is the leader peptide that leads to this ordering of LynD by reducing the volume available for this region and secondly by making specific contacts; a salt bridge between PatE' E32 and LynD R399 and a hydrophobic cluster of PatE L34 with V217 and L398 of LynD. These interactions depend upon the dimer, as it is the other subunit of LynD which supplies these residues and which is ordered by the leader peptide.

Figure 2:
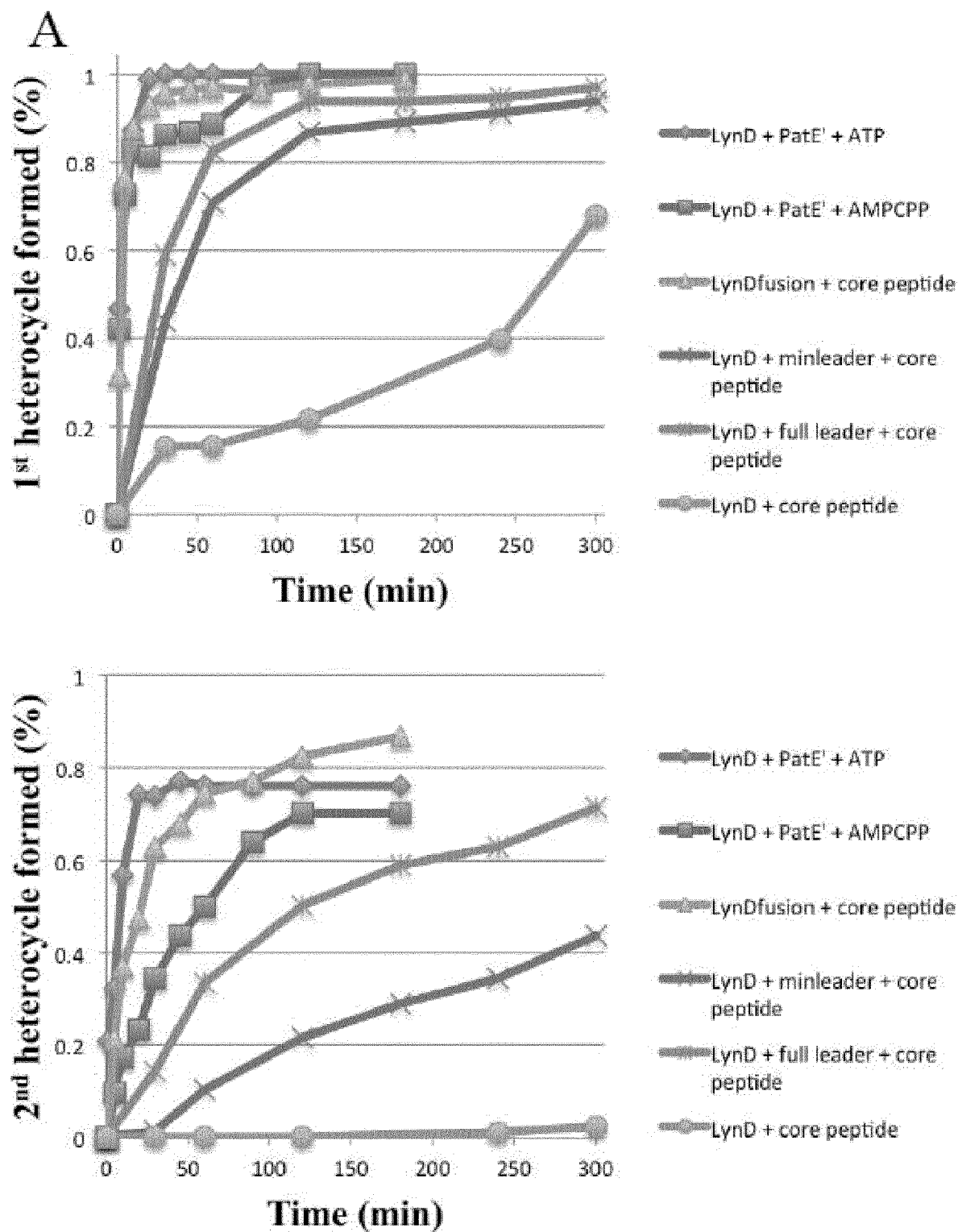
FIG. 2 shows the relative rates of various cis and trans activated heterocyclization reactions analysed by MALDI TOF MS. The top graph shows the time taken to complete $1^{st}$ heterocycle and the bottom graph shows the time taken to form the $2^{nd}$ heterocycle.
Figure 3:
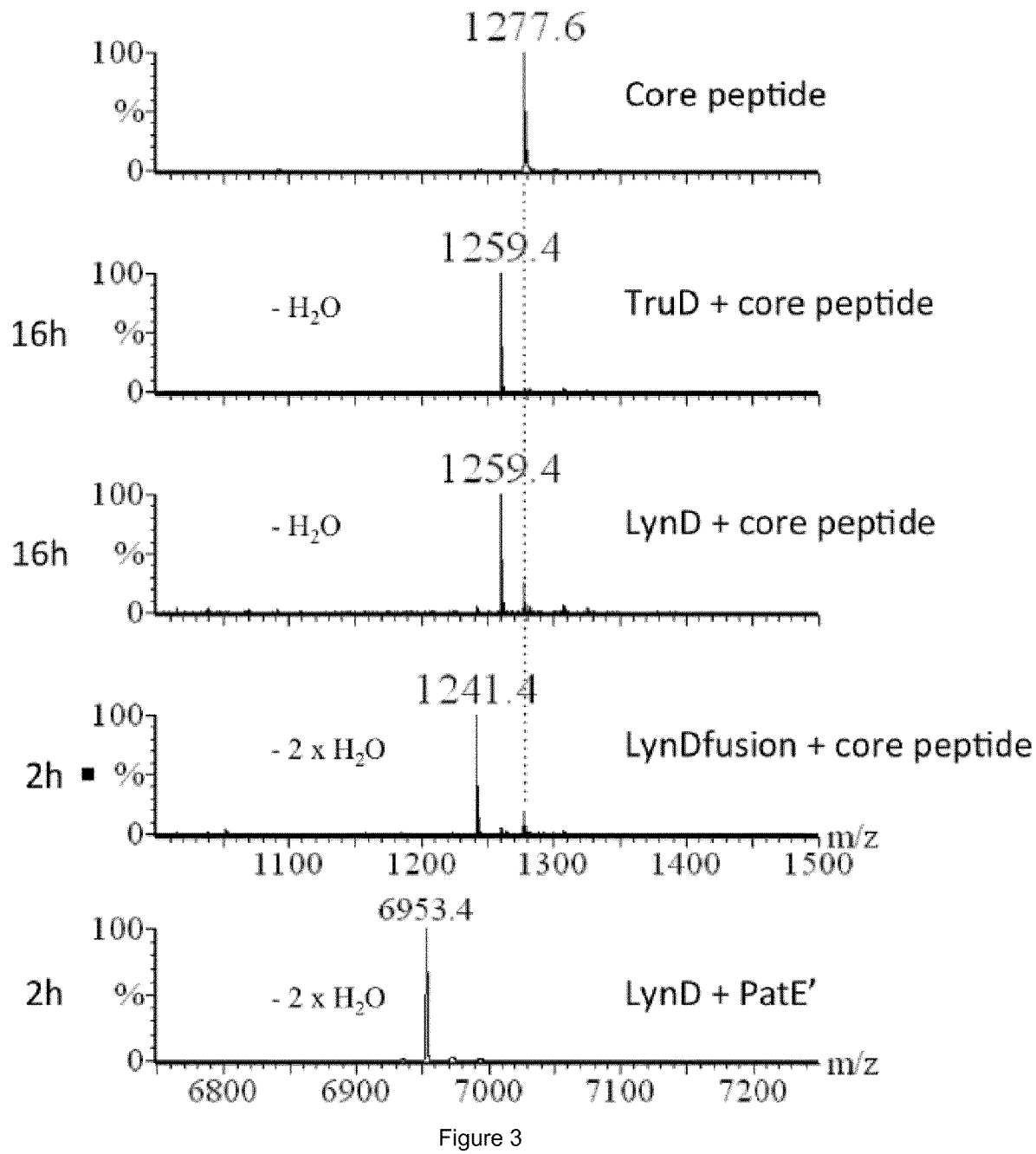
FIG. 3 shows LCMS analysis of heterocyclization reactions of core peptide (ITACITFCAYDG, SEQ ID NO:46) incubated with TruD, LynD and LynD fusion. After 16 h core peptide incubated with either TruD or LynD only 1 heterocycle is formed. In contrast when incubated with LynD fusion, the heterocyclization reaction is nearly complete—the sample containing predominantly 2 heterocycles after just 2 h. PatE' and LynD reaction after 2 h is shown as a reference.
Figure 4:
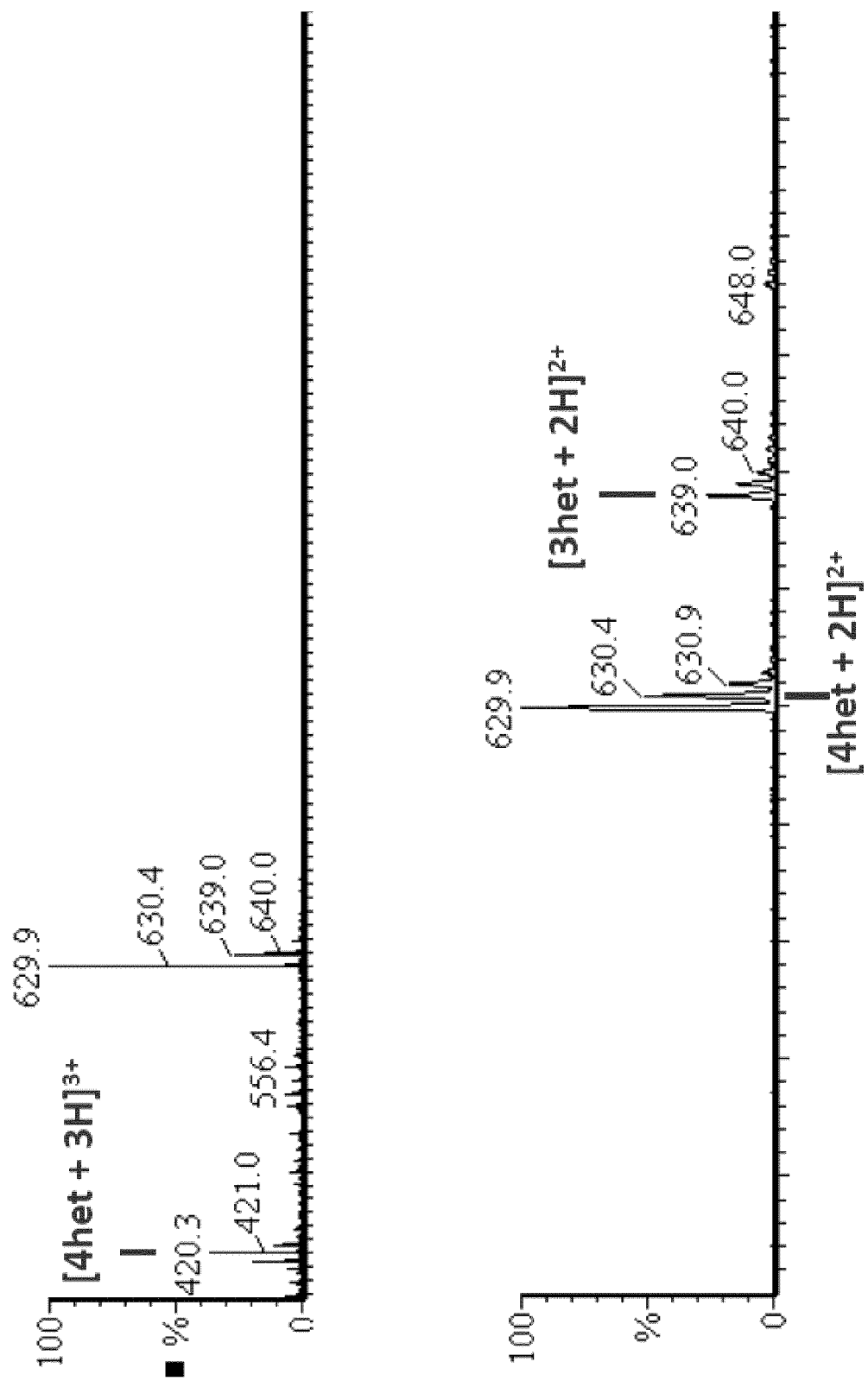
FIG. 4 shows full-range (upper panel) and zoomed (lower panel) LC-ESI-MS of substrate peptide ITACITACAYDGE (SEQ ID NO:47) processed with MicD Q21-5GA (heterocyclizable residues are underlined). The Reaction was performed in 100 mM Tris pH 8.0 supplemented with 150 mM NaCl, 5 mM ATP and 5 mM $MgCl_2$ and contained 20 μM enzyme and 100 μM peptide. The mixture was incubated at 27° C. for 16 h. The unprocessed substrate has a molecular weight of 1329.5 Da.
Figure 5:
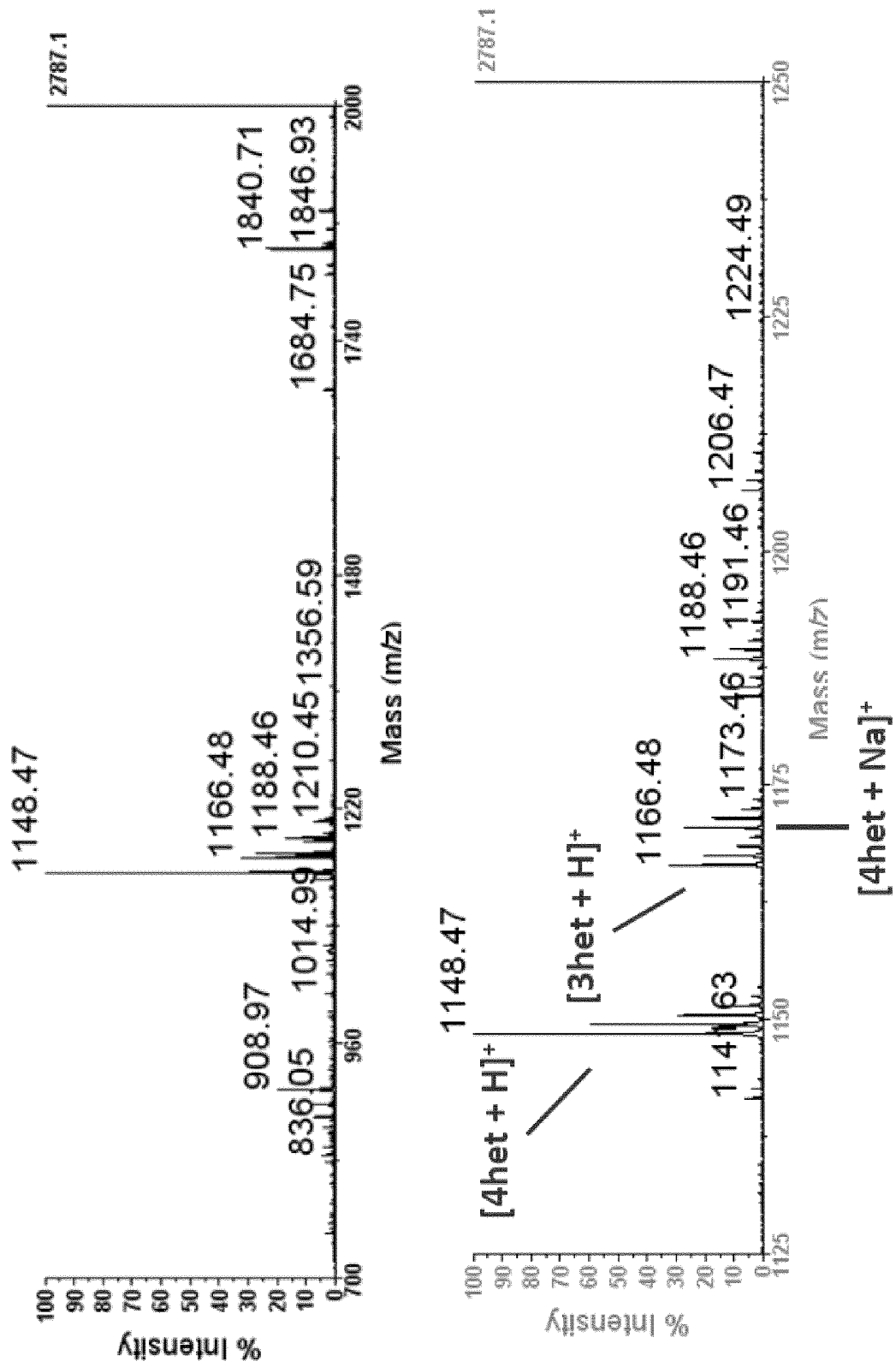
FIG. 5 shows full-range (upper panel) and zoomed (lower panel) MALDI-TOF-MS of substrate peptide ITACITACAYDGE (SEQ ID NO:47) processed with PatD Q21-7GA. Reaction was performed in 50 mM Bicine pH 9.0 supplemented with 150 mM NaCl, 5 mM ATP and 5 mM MgCl2 and contained 30 μM enzyme and 110 μM peptide. The mixture was incubated at 27° C. for 16 h. The unprocessed substrate has a molecular weight of 1219.5 Da.
Figure 6:
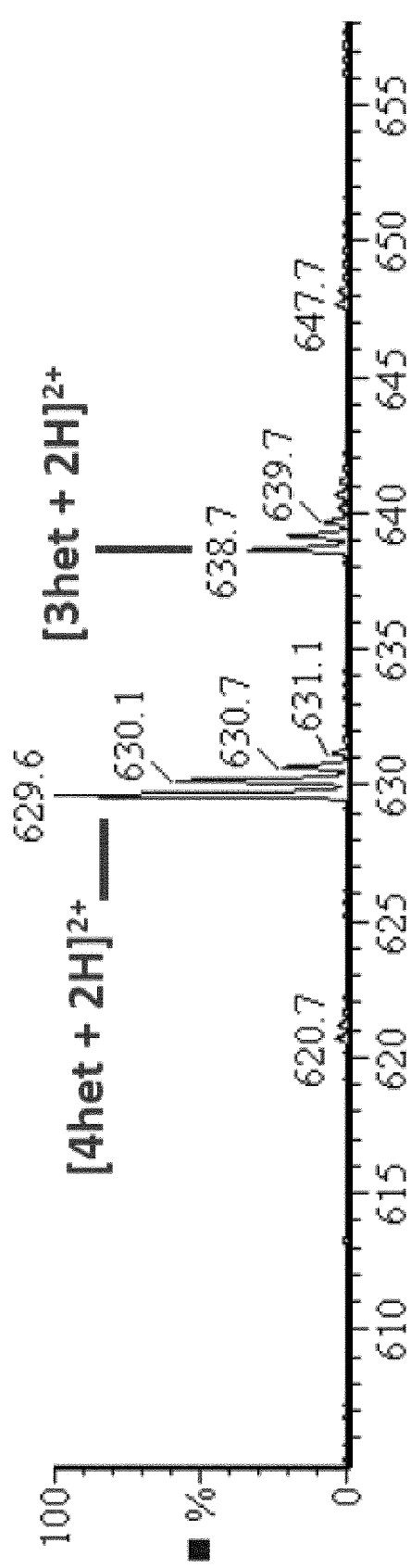
FIG. 6 shows LC-ESI-MS spectra (zoomed) of ITACITACAYDGE (SEQ ID NO:47) processed with MicD Q21-9GA. Each reaction contained 100 mM Tris pH 8.0, 150 mM NaCl, 5 mM ATP and 5 mM MgCl2, 20 μM of the respective enzyme and 100 μM substrate peptide, and was incubated at 27° C. for 16 h. The unprocessed substrate has a molecular weight of 1329.5 Da.
Figure 7:
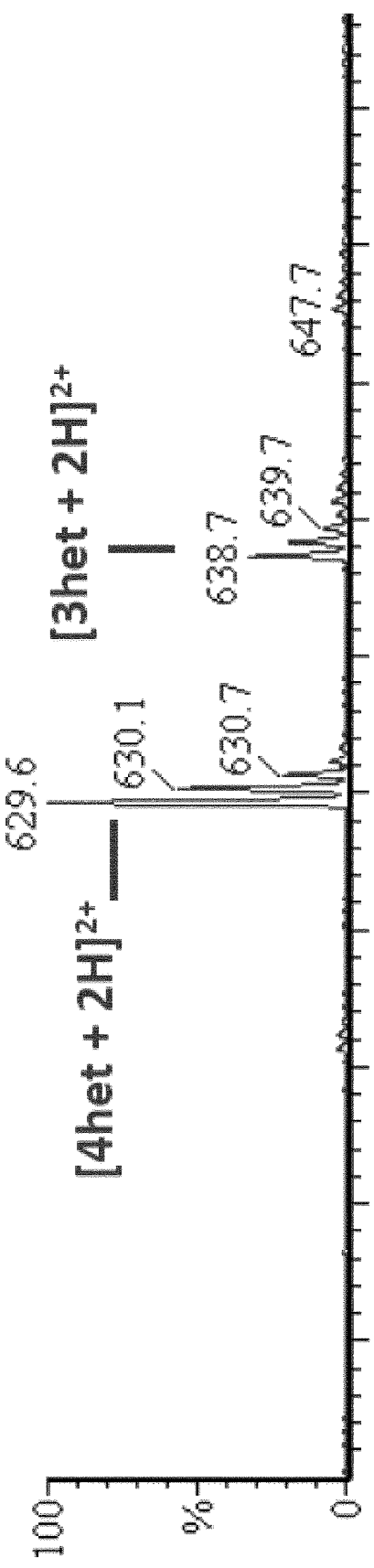
FIG. 7 shows LC-ESI-MS spectra (zoomed) of ITACITACAYDGE (SEQ ID NO:47) processed with MicD R16-5GA. Each reaction contained 100 mM Tris pH 8.0, 150 mM NaCl, 5 mM ATP and 5 mM MgCl2, 20 μM of the respective enzyme and 100 μM substrate peptide, and was incubated at 27° C. for 16 h. The unprocessed substrate has a molecular weight of 1329.5 Da.

Incubation of LynD with either full-length PatE leader (up to the core peptide) or minimal leader accelerates the turnover of the test peptide (6.7- and 5.0-fold, respectively), such that both heterocycles are observed in an overnight incubation (FIG. 2). In the absence of the leader predominantly one heterocycle is observed as previously reported (FIGS. 2 and 3) {Koehnke et al., 2013, Angew Chem Int Ed Engl, 52, 13991-6}. The acceleration was more pronounced with the full-length peptide than with the minimal peptide and reproduces a previous report of trans activation of PatD by full-length leader (FIG. 2) {Goto et al., 2014, Chem Biol, 21, 766-74}. In our hands this trans activation remained slower than seen for full length PatE'. Guided by structural analysis, the leader peptide (residues 21 to 38) was fused to the N-terminus of LynD to construct a self-activating enzyme. This engineered enzyme expressed to a higher soluble yield than native protein and ran normally as a dimer on gel filtration. It processed both cysteines in the test peptide at a rate comparable to the full length PatE' substrate (FIGS. 2 and 3).

The ability of heterocyclases to separate recognition from the catalytic site is highly desirable in biotechnology, conferring specificity by recognizing an invariant leader but tolerating a wide range of residues adjacent to the target cysteine (or serine/threonine). Such spatial separation and use of a leader is a feature of other post translational modifying enzymes such as those found in the lantibiotic pathway {Willey and van der Donk, 2007, Annu Rev Microbiol, 61, 477-501; Oman and van der Donk, 2010, Nat Chem Biol, 6, 9-18}. In the PatD heterocyclase class of enzymes the leader is not absolutely required for processing of the terminal cysteine of the cassette but it is essential for detectable processing of internal cysteine residues within a time frame of hours {Koehnke et al., 2013, Angew Chem Int Ed Engl, 52, 13991-6; Goto et al., 2014, Chem Biol, 21, 766-74; Ruffner et al., 2014, ACS Synth Biol} (FIG. 3A,B and S5). The structure shows that LynD uses the β sheet of domain 1 to bind a conserved region within the leader of PatE'. By anchoring the substrate peptide it converts an intermolecular reaction into an intramolecular one with the concomitant reduction in the entropy penalty and increase in local concentration, these two factors accelerate catalysis of both first and second hetereocyclisation (FIG. 3). The substrate leader peptide also makes contacts with domain 3, the catalytic domain, where it stabilizes a loop involved in the active site. Importantly the leader peptide bridges domain 1 of LynD from one monomer to domain 3 of LynD from the other monomer. Simple distance constraints suggest that processing of the core peptide must occur in the same domain 3 that contacts the leader (different monomer than domain 1) thus the dimer itself is a functional requirement. This is reminiscent of but different to the McсB system where domain 1 also acts a peptide clamp within a dimeric arrangement. However in McсB the region of domain 1 and the interactions between its 'leader' peptide are different from that observed here {Regni et al., 2009, EMBO J, 28, 1953-64}. The BalhC protein, which is required for efficient heterocyclization of cysteine residues in leader containing linear peptides by BalhD, clearly contains the peptide clamp domain and we propose it will operate in similar manner. The presence of a structurally and functionally conserved peptide clamp domain in three different enzymes that operate on different substrates suggests that the peptide clamp may be general for peptide processing enzymes that utilize leader peptides for recognition. The low level of sequence homology between McсB and TruD prevented confident identification of the conserved nature of the peptide clamp but with multiple structures of this domain, identification of homologues is now more reliable.

The stabilization of the active site loops by the leader peptide offers a molecular rational for the trans activation of PatD by the leader peptide {Goto et al., 2014, Chem Biol, 21, 766-74} and a molecular route by which catalysis and substrate binding/product release may be correlated. We show that the trans effect can be observed even with a very small minimal leader, but much stronger trans activation occurs with a full-length leader (FIGS. 2 and 3). Following the example from lantibiotic synthetase where the need for a peptide substrate leader was removed by fusing the leader to the lantibiotic synthetase enzyme {Oman et al., 2012, J Am Chem Soc, 134, 6952-5}, an engineered LynD was designed based on our structural and biochemical insights into the role of the leader in LynD. The fused enzyme was indeed as active at processing two cysteines within a test peptide as native LynD with PatE' substrate (FIGS. 2 and 3). The introduction of multiple heterocycles into a simple, short, linear peptide is a very highly desired chemical modification and up to this point required the synthesis of a long peptide, most of which is discarded making chemical synthesis of the peptide unattractive. However, the newly engineered LynD can act on peptides with no leader and for those where macrocyclization is required only three C-terminal residues (AYD), which are disposed of, are required.

2.4 Heterocyclization

Figure 8:
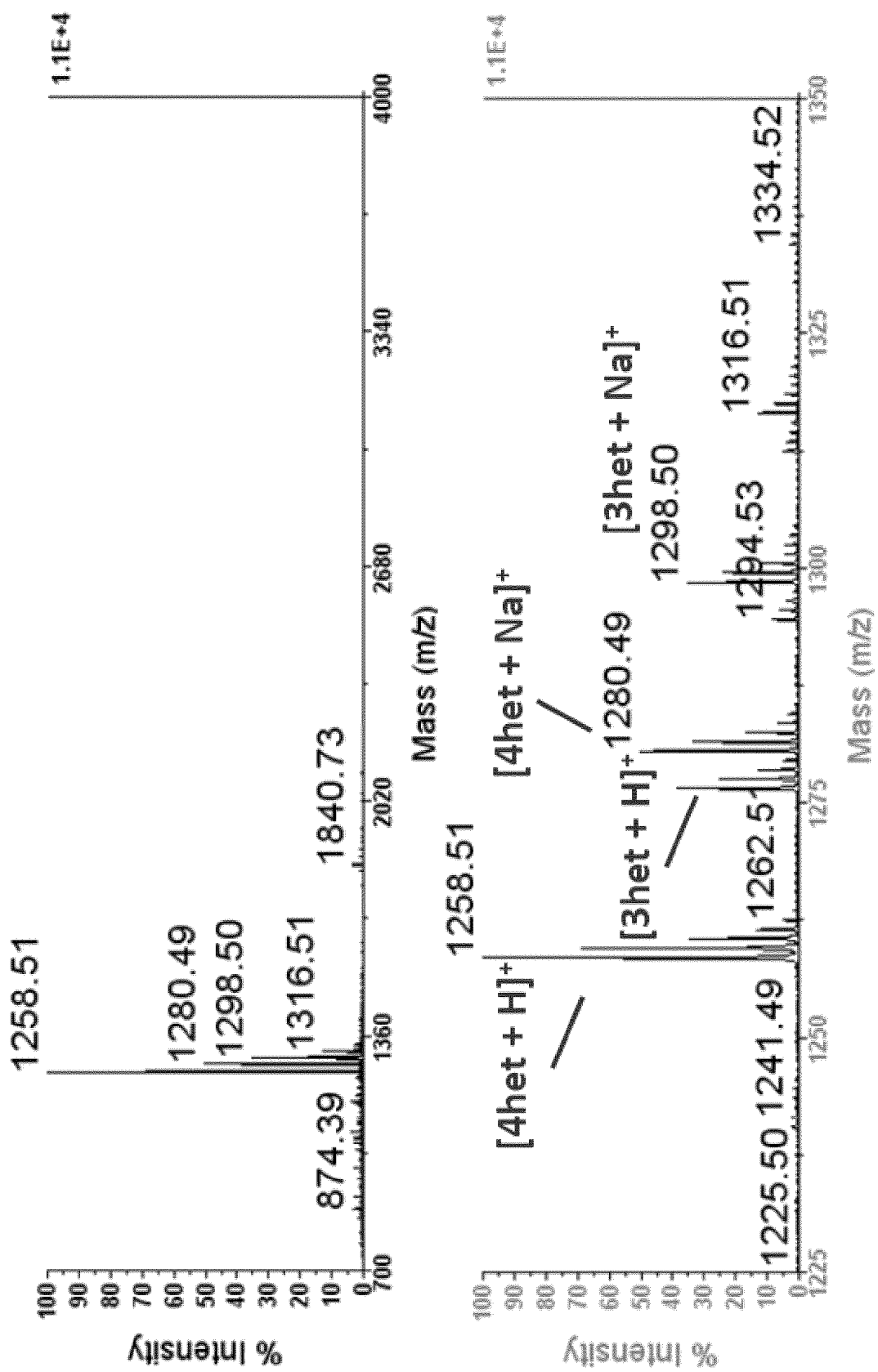
FIG. 8 shows the full-range (upper panel) and zoomed (lower panel) MALDI-TOF-MS of ITACITACAYDGE (SEQ ID NO:47) processed with MicD R16-GLEAS-5GA. Reaction was performed in 50 mM Bicine pH 9.0 supplemented with 150 mM NaCl, 5 mM ATP and 5 mM MgCl2 and contained 30 μM enzyme and 110 μM peptide. The mixture was incubated at 27° C. for 16 h. The unprocessed substrate has a molecular weight of 1329.5 Da.

Two enzymes (MicD and PatD) are capable of catalyzing the heterocyclization of Cysteine, Threonine and Serine residues. Using the fused-LynD enzyme as a template, MicD and fPatD enzymes were fused with leader peptide sequences to produce fused-MicD and fused-PatD enzymes. The ability of fused-MicD and fused-PatD to introduce thiazolines and oxazolines on leaderless substrates was demonstrated. Five variants of fused-MicD/PatD enzymes were characterized in this study: MicD-Q21-5G (SEQ ID NO: 33), MicD-Q21-9GA (SEQ ID NO: 34), MicD-R16-5GA (SEQ ID NO: 35), MicD-R16-GLEAS-5GA (SEQ ID NO: 36), and PatD-Q21-7GA (SEQ ID NO: 38; where 'Q21/R16' denotes the N-terminal residue of the native substrate's leader sequence that is fused to the protein, and 'XGA' describes the number of repeats of the amino acids G and A in the linker region before the 'KL'. The 'GLEAS' denotes an extension of the leader sequence prior to the GA linker region. Similarly to the fused-LynD enzyme, our fused-MicD/PatD enzymes were found to fully process synthetically produced patellamide-like core peptides to produce species in which all four of the cysteine and threonine residues were heterocyclized (denoted "4het"). Peaks that were attributable to residual amounts of species with three heterocyclized cysteine or threonine residues were detectable by LC-ESI-MS (FIGS. 4 to 7) No species with less than three heterocyclized cysteine or threonine residues were detectable by this method (FIGS. 4 to 7). The inclusion of an additional GLEAS sequence adjacent the linker had no effect on heterocyclization (FIG. 8).

Figure 9:
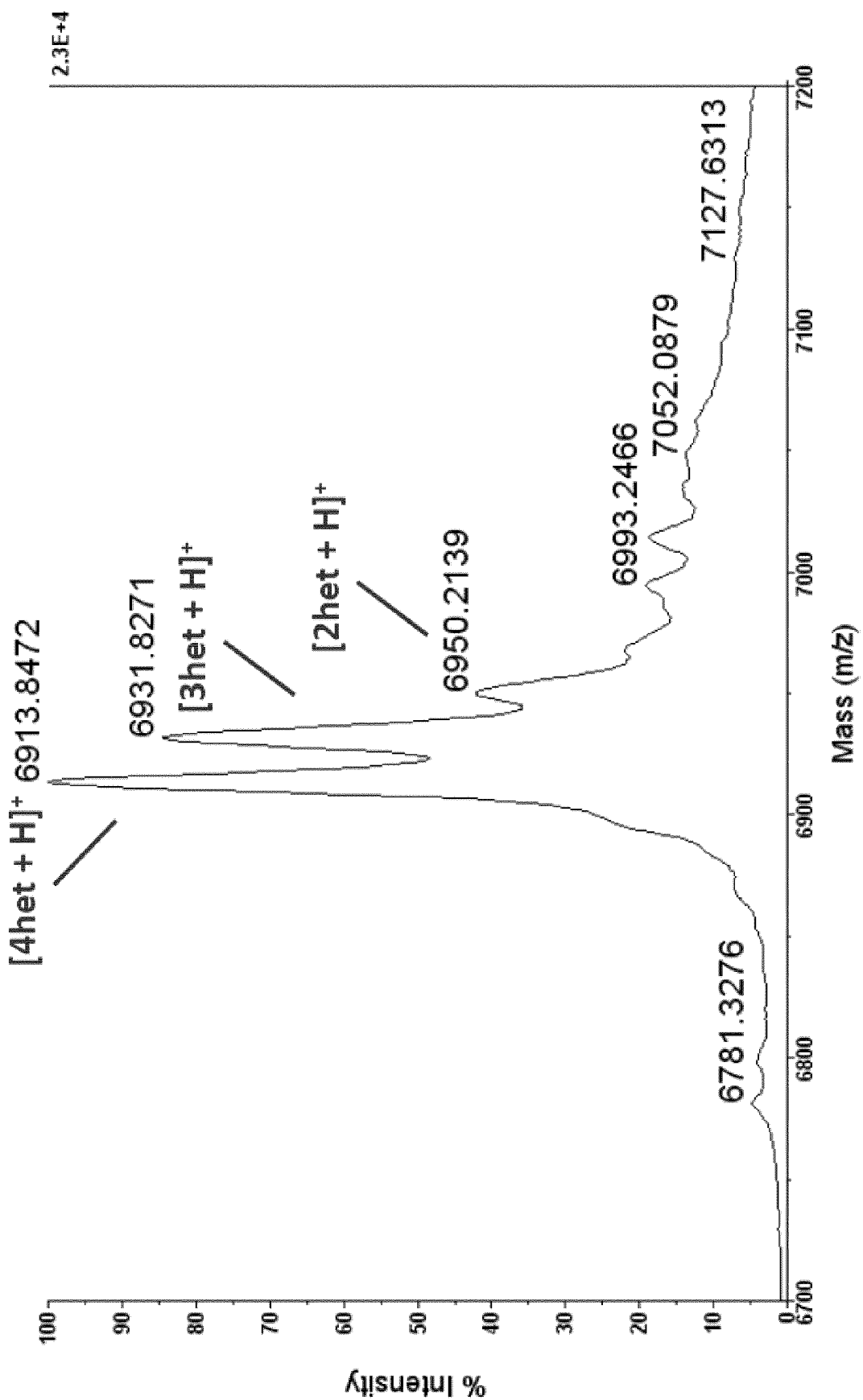
FIG. 9 shows MALDI-TOF-MS of the reaction of a full length PatE substrate (core sequence ITVCISVC, SEQ ID NO:61) and MicD Q21-5GA. Reaction Zoomed view with reaction products identified. The mass of the starting material is 6983.8 Da.

MicD-Q21-5G was found to heterocyclize full-length PatE inefficiently and produce a mixture of different heterocyclic species (FIG. 9). Modified heteroclases are therefore less active on wild-type cyanobactin substrates than synthetic leaderless substrates.

Figure 10:
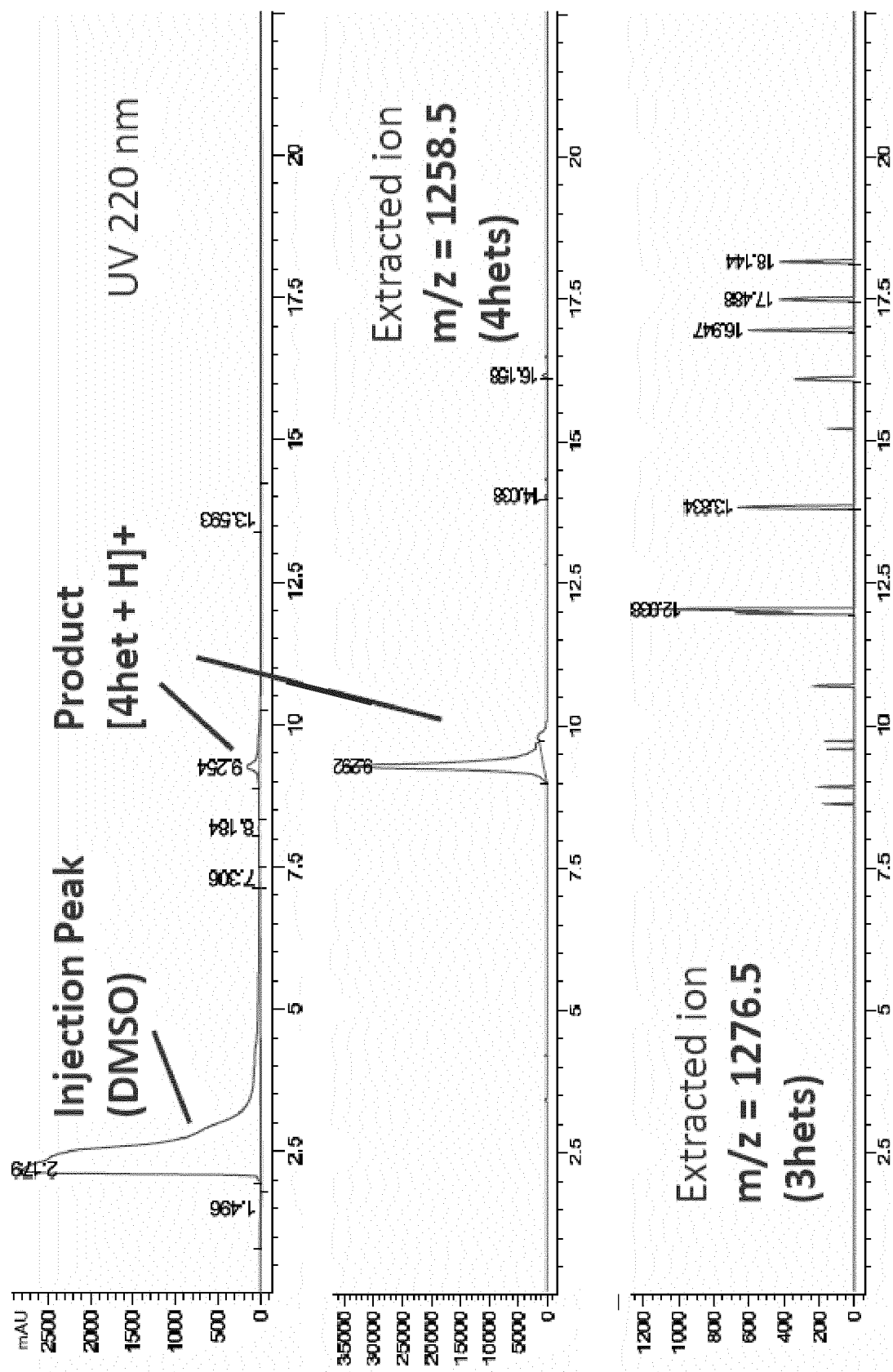
FIG. 10 shows HPLC-ESI-MS of the reaction product of ITACITACAYDGE (SEQ ID NO:47) processed with MicD-Q21-9GA. Upper Panel shows the UV absorbance at 220 nm. Only 1 peak (9.254 min) indicates the reaction product is only one species. Middle Panel shows the extracted ion chromatogram for m/z=1258.5 (4het+H) indicating species present contains 4 heterocycles. Lower Panel shows the extracted ion chromatogram for m/z=1276.5 (3het+H). Multiple peaks of low intensity compared with m/z=1258.5 can be attributed to noise. Product was purified from the enzyme and ATP using size exclusion chromatography (Superdex 30, GE Healthcare) and exchanged into 50 mM Bicine pH 9.0, 500 mM NaCl and 5% DMSO.

HPLC-ESI-MS analysis of the products of heterocyclization of ITACITACAYDGE by MicD-Q21-9G detected only a single four heterocycle species (FIG. 10). No species containing fewer than four heterocycles were detected.

We show that enzymatic heterocyclization can be efficiently and cost effectively coupled to chemical peptide synthesis allowing an explosion in diversity by the introduction of multiple non-natural amino acids in both linear and macrocylic heterocycle containing peptides.

```
Sequences
                                                                                           SEQ ID NO: 1
    1 mqstpllgiq phfhveviep kqvyllgega nhaltgqlyc qilpllngqy tlegivekld 61 gevppeyidy vlerlaekgy lteaapelss evaafwselg iappvaaeal rqpvtltpvg 121 nisevtvaal ttalrdigis vqtpteagsp talnvvltdd ylqpelakin kqalesqqtw 181 llvkpvgsvl wlgpvfvpgk tgcwdclahr lrgnreveas vlrqkqaqqg rngqsgsvig 241 clptaratlp stlqtglqfa atelakwivk yhvnatapgt vffptldgki itlnhsildl 301 kshilikrsq cptcgdpkil qhrgfeplkl esrpkqftsd gghrgttpeq tvqkyqhlis 361 pvtgvvtelv ritdpanplv htyraghsfg satslrglrn tlkhkssgkg ktdsqskasg 421 lceaverysg ifqgdeprkr atlaelgdla ihpeqclcfs dgqyanretl neqatvandw 481 ipqrfdasqa lewtpvwslt egthkylpta lcyyhyplpp ehrfargdsn gnaagntlee 541 allqgfmelv erdgvalwwy nrlrrpavdl gsfnepyfvq lqqfyrendr dlwvldltad 601 lgipafagvs nrktgsserl ilgfgahldp tiallravte vngigleldk vpdenlksda 661 tdwlitekla dhpyllpdtt qplktagdyp krwsddlytd vmtcvniagq agletividq 721 trpdiglnvv kvtvpgmrhf wsrfgegrly dvpvklgwld eplteaqmnp tpmpf
      (LynD; WP_009787121.1 GI:497472923)
                                                                                           SEQ ID NO: 2
    1 mqptalqikp hfhveiiepk qvyllgeggn haltgqlycq ilpflngeyt regivekldg 61 qvpeeyidfv lsrlvekgyl tevapelsle vaafwselgi apsvvaeglk qpvtvttagk 121 giregivanl aaaleeagiq vsdpkapkap kagdstaqlq vvltddylqp elaainkeal 181 erqqpwllvk pvgsilwlgp lfvpgetgcw hclaqrlrgn reveasvlqq kralgerngq 241 nkngaysclp taratlpstl qtglqwaate lakwmvkrhl nalapgtarf ptlagkiftf 301 nqttlelkah plsrrpqcpt cgdgellqrr gfeplklesr pkhftsdggh rattpeqtvg 361 kyqhligpit gvvtelvris dpanplvhty raghsfgssa gslrglrntl rykssgkgkt 421 dsqsrasglc ealerysgif lgdeprkrat laelgdlaih peqclhfsdr qydnrdalna
```

-continued

```
481 egsaaayrwi phrfaasqai dwtplwslte qkhkyvptai cyynyllppa drfckadsng
541 naagnsleea ilqgfmelve rdsvalwwyn rlrrpevels sfeepyflql qqfyrsqnre
601 lwvldltadl gipafaglsr rtvgsservs igfgahldpk iailraltev sqvgleldkv
661 pdekldgesk dwmlevtlet hpclapdpsq prktandypk rwsddiytdv macvemakva
721 gletlvldqt rpdiglnvvk vmipgmrtfw srygpgrlyd vpvqlgwlke plaeaemnpt
781 nipf
(PatD; AAY21153.1 GI:62910840)
```

SEQ ID NO: 3

```
  1 mqptalqikp hfhveiiepk qvyllgeggn haltgqlycq ilpflngeyt regivekldg
 61 qvpeeyidfv lsrlvekgyl tevapelsle vaafwselgi apsvvaeglk qpvtvttagk
121 giregivanl aaaleeagiq vsdprdpkap kagdstaqlq vvltddylqp elaainkeal
181 erqqpwllvk pvgsilwlgp lfvpgetgcw hclaqrlqgn reveasvlqq kralgerngq
241 nkngaysclp taratlpstl qtglqwaate lakwmvkrhl naiapgtarf ptlagkiftf
301 nqttlelkah plsrrpqcpt cgdretlqrr gfeplklesr pkhftsdggh ramtpeqtvg
361 kyqhligpit gvvtelvris dpanplvhty raghsfgsat slrglrnvlr hkssgkgktd
421 sqsrasglce alerysgifq gdeprkratl aelgdlaihp eqclhfsdrq ydnressner
481 atvthdwipq rfdaskandw tpvwslteqt hkylptalcy yrypfppehr fcrsdsngna
541 agntleeall qgfmelverd svclwwynry srpavdlssf depyflqlqq fyqtqnrdlw
601 vldltadlgi pafvgvsnrk agsserillg fgahldptva ilraltevnq igleldkvsd
661 eslkndatdw lvnatlaasp ylvadasqpl ktakdyprrw sddiytdvmt cvelakqagl
721 etivldqtrp diglnvvkvi vpgmrfwsrf gsgrlydvpv klgwreqpla eaqmnptpmp
781 f
(TruD; ACA04490.1 GI:167859097)
```

SEQ ID NO: 4

```
  1 mqstpllgiq phfhveveviep kqvyllgega nyaltgqlyc qilpllngqh sregivekld
 61 gevpseyidy vldrlaekgy lteaapelss evaafwselg iappvaaeal rqpvtltpvg
121 nisevtvaal ttalrdigis vqtsteaysp talnvvltdd ylqpelakin kqalesqqtw
181 llvkpvgsvl wlgpvfvpgk tgcwdclahr lrgnreveas vlqqkqaqqg rngqsgsvig
241 clptaratlp stlqtglqfa atelakcivk hhvnatapgt vffptldgki itlnhsildl
301 kshilikrsq cstcgdrqil hrqgfepvkl vsrrkhfthd gghraftpeq tvqkyqhlvs
361 pitgvvtelv rltdpanplv htykaghafg sattlrglrn tlkykssgkg ktdiqsrasg
421 lceaierysg ifqgdeprkr atlaelgdla lhpesllyfs dtqyanreel naggsaaayr
481 wipnrfdvsq aldwtpvwsl teqkhkyvpt afcyygyplp eeqrfckads ngnaagntle
541 eailqgflel verdslamww ynrirrpavd lstfdepyfv dlqqfyqqqn relwvldvta
601 dlgipafagf srrtvgtser isigfgahld ptiailralt evsqvgleld kipddkldge
661 skdwmlnvtv enhpwlapdp svpmktasdy pkrwsddiht dvmncvktaq taglevmvld
721 qtrpdiglnv vkvilpgmrt fwtrfgqgrl ydipvklgwl daplaeeeln qtnipf
(MicD; WP_002796590.1 GI:488884365)
```

SEQ ID NO: 5

```
  1 mqsttllqik phfhieviep kqvyllgeqg nhaltgelyc givplidgqh tieqiiqkld
 61 gqvpaeyidy vlnrlaekgy lteatpdlsp evaafwtelg laptvaaggl kgpvtlttvg
121 enisevtvaa latalrdmgi pvqnasdigs saalnivltd dylqpelaai nkqalqsqqt
181 wllvkpvgsv lwlgpvfvpq ktgcwsclah rlrgnreves svlrqkqaqq erngqqgrvv
241 sslptaratl pstlqtalqf aatelakwiv kqyvnatapg talfptldgk vitfnqtild
```

```
301 lkshllikrp qcptcgdpei mqrrgfeplk lesrrkrfth dgghrattpe qtlqkyqhli
361 gpvtgvvtel vritdpanpl vhtyraghsf gsatslrglr ntlrhkssgk gktdsqsras
421 gfceaverys gifqgdeprk ratfaeladl alhpaqclhf sdeqytnrea lnaggteaay
481 rwiphrfdas qaidwtpvws ltegrhkylp tglcyyhypm peanrfckad sngnaagntl
541 eeallqgfme lverdsvalw wynrlsrpgv dltsfnepyf vqlqqfyreq nrelwvidlt
601 adfgisafvg vsyrtvgtse riivgfgahl dptigilrtl tevsgiglel dkipdeqlkd
661 eskdwilgvt reshpclvpd psqpiktand ypkrwsddiy tdvmtcvkla qgigletlvl
721 dqtrpdigin vvkvilpgtr glwsrfgpgr lydvpvklgw rtvplveaem npmnipf
(TenDACA04483.1 GI:167859089)
```

SEQ ID NO: 6

```
  1 mmknevlnyk piidsycfvk eddegltffn rdtyinfhgg svedifalip lltgklsteg
 61 laeklelpie ymcdiiklld ekniiknydl qekykfmdke lqryerfisn ltgslssafe
121 giealytkki vlmgneelge svrkacgtkf sflemsqign asliiavdfc enenlfsean
181 elskcykvpf lrgvvqeqyf sigpifisne tgcyncflsr kitnyensyl sykymkkyns
241 ewnethvgvi pgtiemlsfn ilsfimkyfs dcmpceiigk eftynvfnls snlnpvlkvp
301 gcsicagank nimkdfvlns
(YP_893376.1 GI:118476225)
```

SEQ ID NO: 7

```
  1 mknevinykp ildsycfvke ddegltffnr dtyinfhggs vedifalipl ltgklsteql
 61 aeklelpley mcdiiklide kniiknydlq ekykfmdkel gryerfisni tgslssafeg
121 lealytkkiv lmgneelges vrkacgtkfs flemsqiqna sliiavdfce nenlfseane
181 lskcykvpfl rgvvqegyfs igpifisnet gcyncflsrk itnyensyls ykymkkynse
241 wnethvgvip gtiemlsfni lsfimkyfsd cmpceiigke ftynvfnlss ninpvikvpg
301 csicagankn imkdfvins
(YP_005117210.1 GI:376264498)
```

SEQ ID NO: 8

```
  1 mgiqnaleyi inkntgiihh vknemnfkll fpmhiyftfr nelvdvnegi kirgnysglg
 61 ysydsaesal isavgeiler ycscylntea liknsynslv ksnvyalnpl sitqpireqy
121 getygiskel dgdtifnwvq akdeiykknv lvpantiyfd vdeefllphi rdsistglat
181 gstrlqalen aalecierda imitwlnels vplidsqtip detiqyylkv adekgfevff
241 fdittdikvp tyfvlvrnly nkyphiliga kahydplial kgalmetlas lnlladpnnk
301 tteavdikdt iniksikdhm hyyasgntke afdflissp rpfnnysein nfeelkvkln
361 tmnlnlytyd lttedissig lyvyrvlmpe lafleitlpm iscnrlldap knmgyapaka
421 fnknphpfp
(YP_893377.1 GI:118476226)
```

SEQ ID NO: 9

```
  1 mgignaleyi inkntgiihh vknemdfklp fpmhlyftfr nelvdvnygv kirgdygglg
 61 ysydsaesal isavgeiler ycscyinten lincsfnslv kenvhalnpl sitqplreqh
121 gelygnskgi dgdttfnwiq akdeihkkni lvpantlyfd veeefllpqi rdsistglat
181 gssriqalen aalecierda imitwingls vplidpetvp demvqyylkv agekgfevlf
241 fdittdikip tcfvmvrnly nnypyiqvga kahynpltal kgalmetlas lllvnpnne
301 iaeavdiknt qsiksikdhm lyyasgndkd afdfltsssp kpfsyysein nfeelkvkln
361 amdlnlytyd lttedisslg lyvyrvimpe lafleitipm iscnrildap knmgytpakt
```

-continued

```
421 fnknphpfp
(WP_000512737.1 GI:446434882)
```

SEQ ID NO: 10

AAG $X_1$ $X_2$ $X_3$E $X_4$A $X_5$LQG $X_6X_7$E $X_8$ $X_9$ ERD $X_{10}$ $X_{11}$
where $X_1$ is N or T; $X_2$ is T, C or S; $X_3$ is L or I; $X_3$ is F, L, I or M;
$X_4$ is E or D; $X_5$ is I or V; $X_6$ is F or L; $X_7$ is M, L or F; $X_8$ is L or V; $X_9$ is
V or I; $X_{10}$ is S, A, or C; and $X_{11}$ is V or I

SEQ ID NO: 11

AAGNTLEEAILQGFMELVERDSV

SEQ ID NO: 12

$X_1$S$X_2X_3X_4$E$X_5X_6$ ERY $X_7$ $X_8$ $X_9$ $X_{10}$ $X_{11}$G$X_{12}$E
where $X_1$ is A, V or M; $X_2$ is G or A; $X_3$ is L or I; $X_3$ is L, V or F; $X_4$ is C
or G; $X_5$ is A or S; $X_6$ is I, V or L; $X_7$ is S or A, $X_8$ is G or F; $X_9$ is I, L,
T or V; $X_{10}$ is F or Y and $X_{11}$ is Q, E, T or L; $X_{12}$ is D, Y, E or N.

SEQ ID NO: 13

ASGLCEAIERYSGIFQGDE

SEQ ID NO: 14

LAELX$_1$EEX$_2$X$_3$,
where $X_1$ is S or T, preferably S, $X_2$ is A, V, T or N and $X_3$ is L or I

SEQ ID NO: 15

LAELSEEAL

SEQ ID NO: 16

LAELSEETL

SEQ ID NO: 17

LAELSEEAI

SEQ NO: 18

<u>MDKKNILPQQ GQPVIRLTAG QLSSQLAELSEEALGDAGLE ASK</u>ITACITF C*AYDGELEHH HHHH*
Amino acid sequence of PatE; Core peptide bold, leader underlined, His tag
italicised

SEQ ID NO: 19

```
  1 mnkknilpql gqpvirltag qlssqlaels eealgqvdas tlpvptlcsy dgvdastvpt 61 lcsydd
```
(TruE1 ACA04491.1 GI:167859098) Core peptide bold, leader underlined

SEQ ID NO: 20

```
  1 mnkknilpql gqpvirltag qlssqlaels eealgqvdas tfpvptvcsy dgvdastsla 61 pfcsydd
```
(TruE2 ACA04495.1 GI:167859103) Core peptide bold, leader underlined

SEQ ID NO: 21

```
  1 mnkknilpql gqpvirltag qlssqlaels eealgqvdas tsiapfcsyd gvdastslap 61 fcsydgvdas tslapfcsyd d
```
(TruE3 ACA04496.1 GI:167859105) Core peptide bold, leader underlined

SEQ ID NO: 22

```
  1 mdkknilpqq gkpvirittg qlpsflaels eealgdaqvg asatgcmcay dgagasatgc 61 mcaydgagas atacacaydg agasatacac aye
```
(TenE ACA04484.1 GI:167859090) Core peptide bold, leader underlined

SEQ ID NO: 23

```
  1 mdkknilpqq gkpvfrtttg klpsylaels eealgqngle ashcaticaf dgaeashcat 61 icafdgaeas hcaticafdg dea
```
(WP_002734081.1 GI:488821675) Core peptide bold, leader underlined

SEQ ID NO: 24

```
  1 mdkknllpnq gapvirgisg klpshlaels eealgqngle asytssicaf dgaeasvlat 61 fcafdgaeas vtvticafdg dea
```
(WP_002796589.1 GI:488884364) Core peptide bold, leader underlined

SEQ ID NO: 25

```
  1 mnkknispnp gqpvdrvptg qlpsalaels eealgsleal psgfmgtgcf phcsydgdde
```
(CDM96176.1 GI:585306494) Core peptide bold, leader underlined

```
                                                                SEQ ID NO: 26
  1 mdkknispnp qqpvdriptq qlpsalaels eealqsqacia qrkcrsaelc syegdde
(WP_008049969.1 GI:495325227) Core peptide bold, leader underlined
```

```
                                                                SEQ ID NO: 27
  1 mdkkniipqq aqpvvrvsqg tqadllaels eetlastpga qasmktndmt lacycvcsyd 61 gddae
(WP_015122227.1 GI:504935125) Core peptide bold, leader underlined
```

SEQ ID NO: 28 menarrqsse gkeaiqmeqk kildikltet gkinyahkpd

SEQ ID NO: 29

$X_4X_5X_6X_7X_8LAELX_1EEX_2X_3LX_9X_{10}X_{11}X_{12}$
where $X_1$ is S or T, preferably S; $X_2$ is A, V, T or N; $X_3$ is L or I or optionally absent; $X_4$ is T, Q or K; $X_5$ is Q, L or K; $X_6$ is A, P or S; $X_7$ is A, D or S; $X_8$ is E, L, A, H or Q or Y; $X_9$ is G or A, preferably G; $X_{10}$ is S, D, G, or absent; $X_{11}$ is T, L, N, A or V or absent; and $X_{12}$ is T, P, A, E, G, D or absent.

SEQ ID NO: 30

$X_{17}X_{16}X_{15}X_{14}X_{13}X_4X_5X_6X_7X_8LAELX_1EEX_2X_3LX_9X_{10}X_{11}X_{12}$
where $X_1$ is S or T, preferably S; $X_2$ is A, V, T or N; $X_3$ is L, I or absent; $X_4$ is T, Q or K; $X_5$ is Q, L or K; $X_6$ is A, P or S; $X_7$ is A, D or S; $X_8$ is E, L, A, H or Q or Y; $X_9$ is G or A, preferably G; $X_{10}$ is S, D, G, or absent; $X_{11}$ is T, L, N, A or V or absent; $X_{12}$ is T, P, A, E, G, D or absent; $X_{13}$ is G or absent; $X_{14}$ is A, T, S, Q or absent; $X_{15}$ is T, I, P, S or absent; $X_{16}$ is L, I, T, G, or V or absent; and $X_{17}$ is R or absent.

SEQ ID NO: 31

$X_1$QLSSQLAELSEEALGDAG
where $X_1$ is absent, G, AG, TAG, LTAG or RLTAG

SEQ ID NO: 32

QLSSQLAELSEEALGDAG

SEQ ID NO: 33

GQLSSQLAELSEEALGDAG

SEQ ID NO: 34

AGQLSSQLAELSEEALGDAG

SEQ ID NO: 35

TAGQLSSQLAELSEEALGDAG

SEQ ID NO: 36

LTAGQLSSQLAELSEEALGDAG

SEQ ID NO: 37

RLTAGQLSSQLAELSEEALGDAG

SEQ ID NO: 38

AGAGAGAGAGA

SEQ ID NO: 39

MSHHHHHHDYDENLYFQGSQLSSQLAELSEEALGDAGAGAGAGAGAGAMQSTPLLQIQPHFHVEVIEPKQVYLLGEQANHALT

GQLYCQILPLLNGQYTLEQIVEKLDGEVPPEYIDYVLERLAEKGYLTEAAPELSSEVAAFWSELGIAPPVAAEALRQPVTLTP

VGNISEVTVAALTTALRDIGISVQTPTEAGSPTALNVVLTDDYLQPELAKINKQALESQQTWLLVKPVGSVLWLGPVFVPGKT

GCWDCLAHRLRGNREVEASVLRQKQAQQQRNGQSGSVIGCLPTARATLPSTLQTGLQFAATEIAKWIVKYHVNATAPGTVFFP

TLDGKIITLNHSILDLKSHILIKRSQCPTCGDPKILQHRGFEPLKLESRPKQFTSDGGHRGTTPEQTVQKYQHLISPVTGVVT

ELVRITDPANPLVHTYRAGHSFGSATSLRGLRNTLKHKSSGKGKTDSQSKASGLCEAVERYSGIFQGDEPRKRATLAELGDLA

IHPEQCLCFSDGQYANRETLNEQATVAHDWIPQRFDASQAIEWTPVWSLTEQTHKYLPTALCYYHYPLPPEHRFARGDSNGNA

AGNTLEEAILQGFMELVERDGVALWWYNRLRRPAVDLGSFNEPYFVQLQQFYRENDRDLWVLDLTADLGIPAFAGVSNRKTGS

SERLILGFGAHLDPTIAILRAVTEVNQIGLELDKVPDENLKSDATDWLITEKLADHPYLLPDTTQPLKTAQDYPKRWSDDIYT

DVMTCVNIAQQAGLETLVIDQTRPDIGLNVVKVTVPGMRHFWSRFGEGRLYDVPVKLGWLDEPLTEAQMNPTPMPF
(His tag-underlined, TEV protease site-double underlined, Linker? dotted underlined)

SEQ ID NO: 40

MSHHHHHHDYDENLYFQGSQLSSQLAELSEEALGDAGAGAGAGAGAKLMQSTPLLQIQPHFHVEVIEPKQVYLLGEQANYALT

GQLYCQILPLLDGQHSREQIVEKLDGEVPSEYIDYVLDRLAEKGYLTEAAPELSSEVAAFWSELGIAPPVAAEALRQSVTLTP

VGNISEVTVAALTTALRDIGISVQTPTEAGSPTALNVVLTDDYLQPELAKINKQALESQQTWLLVKPVGSVLWLGPVFVPGKT

GCWDCLAHRLRGNREVEASVLQQKQAQQQRNGQSGSVIGCLPTARATLPSTLQTGLQFAATEIAKWIVKHHVKATAPGTVFFP

TLDGKIITFNHTVIDLKSHVLVRRSQCPSCGDRQILHRQGFEPVKLVSRRKHFTHDGGHRAFTPEQTVQKYQHLVSPITGVVT

ELVRLTDPANPLVHTYKAGHAFGSATTLRGLRNTLKYKSSGKGKTDIQSRASGLCEAIERYSGIFQGDEPRKRATLAELGDLA

LHPESLLYFSNTQYANREELNAQGSAAAYRWIPNRFDVSQAIDWTPVWSLTEQKHKYVPTAFCYYGYPLPEEQRFCKADSNGN

AAGNTLEEAILQGFLELVERDSIAMWWYNRIRRPAVDLSTFDEPYFVDLQQFYQQQNRELWVLDVTADLGIPAFAGFSRRTVG

TSERISIGFGAHLDPTIAILRALTEVSQVGLELDKIPDDKLDGESKDWMLNVTVENHPWLAPDPSVPMKTASDYPKRWSDDIH

TDVMNCVKTAQTAGLEVMVLDQTRPDIGLNVVKVIIPGMRTFWTRFGQGRLYDIPVKLGWLDAPLAEEELNQTNIPF
MicroD_Q21_5GA (His tag-underlined, TEV protease site-double
underlined, Linker-dotted underline)

SEQ ID NO: 41

MSHHHHHHDYDENLYFQGSQLSSQLAELSEEALGDAGAGAGAGAGAGAGAGAKLMQSTPLLQIQPHFHVEVIEPKQVYLLG

EQANYALTGQLYCQILPLLDGQHSREQIVEKLDGEVPSEYIDYVLDRLAEKGYLTEAAPELSSEVAAFWSELGIAPPVAAEAL

RQSVTLTPVGNISEVTVAALTTALRDIGISVQTPTEAGSPTALNVVLTDDYLQPELAKINKQALESQQTWLLVKPVGSVLWLG

PVFVPGKTGCWDCLAHRLRGNREVEASVLQQKQAQQQRNGQSGSVIGCLPTARATLPSTLQTGLQFAATEIAKWIVKHHVKAT

APGTVFFPTLDGKIITFNHTVIDLKSHVLVRRSQCPSCGDRQILHRQGFEPVKLVSRRKHFTHDGGHRAFTPEQTVQKYQHLV

SPITGVVTELVRLTDPANPLVHTYKAGHAFGSATTLRGLRNTLKYKSSGKGKTDIQSRASGLCEAIERYSGIFQGDEPRKRAT

LAELGDLALHPESLLYFSNTQYANREELNAQGSAAAYRWIPNRFDVSQAIDWTPVWSLTEQKHKYVPTAFCYYGYPLPEEQRF

CKADSNGNAAGNTLEEAILQGFLELVERDSIAMWWYNRIRRPAVDLSTFDEPYFVDLQQFYQQQNRELWVLDVTADLGIPAFA

GFSRRTVGTSERISIGFGAHLDPTIAILRALTEVSQVGLELDKIPDDKLDGESKDWMLNVTVENHPWLAPDPSVPMKTASDYP

KRWSDDIHTDVMNCVKTAQTAGLEVMVLDQTRPDIGLNVVKVIIPGMRTFWTRFGQGRLYDIPVKLGWLDAPLAEEELNQTNI

PF
MicroD_Q21_9GA (His tag-underlined, TEV protease site-double
underlined, Linker-dotted underline)

SEQ ID NO: 42

MSHHHHHHDYDENLYFQGSRLTAGQLSSQLAELSEEALGDAGAGAGAGAGAKLMQSTPLLQIQPHFHVEVIEPKQVYLLGEQA

NYALTGQLYCQILPLLDGQHSREQIVEKLDGEVPSEYIDYVLDRLAEKGYLTEAAPELSSEVAAFWSELGIAPPVAAEALRQS

VTLTPVGNISEVTVAALTTALRDIGISVQTPTEAGSPTALNVVLTDDYLQPELAKINKQALESQQTWLLVKPVGSVLWLGPVF

VPGKTGCWDCLAHRLRGNREVEASVLQQKQAQQQRNGQSGSVIGCLPTARATLPSTLQTGLQFAATEIAKWIVKHHVKATAPG

TVFFPTLDGKIITFNHTVIDLKSHVLVRRSQCPSCGDRQILHRQGFEPVKLVSRRKHFTHDGGHRAFTPEQTVQKYQHLVSPI

TGVVTELVRLTDPANPLVHTYKAGHAFGSATTLRGLRNTLKYKSSGKGKTDIQSRASGLCEAIERYSGIFQGDEPRKRATLAE

LGDLALHPESLLYFSNTQYANREELNAQGSAAAYRWIPNRFDVSQAIDWTPVWSLTEQKHKYVPTAFCYYGYPLPEEQRFCKA

DSNGNAAGNTLEEAILQGFLELVERDSIAMWWYNRIRRPAVDLSTFDEPYFVDLQQFYQQQNRELWVLDVTADLGIPAFAGFS

RRTVGTSERISIGFGAHLDPTIAILRALTEVSQVGLELDKIPDDKLDGESKDWMLNVTVENHPWLAPDPSVPMKTASDYPKRW

SDDIHTDVMNCVKTAQTAGLEVMVLDQTRPDIGLNVVKVIIPGMRTFWTRFGQGRLYDIPVKLGWLDAPLAEEELNQTNIPF
MicroD_R16_5GA (His tag-underlined, TEV protease site-double
underlined, Linker-dotted underline)

SEQ ID NO: 43

MSHHHHHHDYDENLYFQGSRLTAGQLSSQLAELSEEALGDAGLEASGAGAGAGAGAKLMQSTPLLQIQPHFHVEVIEPKQVYL

LGEQANYALTGQLYCQILPLLDGQHSREQIVEKLDGEVPSEYIDYVLDRLAEKGYLTEAAPELSSEVAAFWSELGIAPPVAAE

ALRQSVTLTPVGNISEVTVAALTTALRDIGISVQTPTEAGSPTALNVVLTDDYLQPELAKINKQALESQQTWLLVKPVGSVLW

LGPVFVPGKTGCWDCLAHRLRGNREVEASVLQQKQAQQQRNGQSGSVIGCLPTARATLPSTLQTGLQFAATEIAKWIVKHHVK

ATAPGTVFFPTLDGKIITFNHTVIDLKSHVLVRRSQCPSCGDRQILHRQGFEPVKLVSRRKHFTHDGGHRAFTPEQTVQKYQH

-continued

LVSPITGVVTELVRLTDPANPLVHTYKAGHAFGSATTLRGLRNTLKYKSSGKGKTDIQSRASGLCEAIERYSGIFQGDEPRKR

ATLAELGDLALHPESLLYFSNTQYANREELNAQGSAAAYRWIPNRFDVSQAIDWTPVWSLTEQKHKYVPTAFCYYGYPLPEEQ

RFCKADSNGNAAGNTLEEAILQGFLELVERDSIAMWWYNRIRRPAVDLSTFDEPYFVDLQQFYQQQNRELWVLDVTADLGIPA

FAGFSRRTVGTSERISIGFGAHLDPTIAILRALTEVSQVGLELDKIPDDKLDGESKDWMLNVTVENHPWLAPDPSVPMKTASD

YPKRWSDDIHTDVMNCVKTAQTAGLEVMVLDQTRPDIGLNVVKVIIPGMRTFWTRFGQGRLYDIPVKLGWLDAPLAEEELNQT

NIPF

MicroD_R16_GLEAS_5GA (His tag-underlined, TEV protease site-double underlined, Linker-dotted underlined)

SEQ ID NO: 44

MS<u>HHHHHH</u>DYD<u>ENLYFQ</u>GSQLSSQLAELSEEALGDAGAGAGAGAGAKLMQPTALQIKPHFHVEIIEPKQVYLLGEQGNHALTG

QLYCQILPFLNGEYTREQIVEKLDGQVPEEYIDFVLSRLVEKGYLTEVAPELSLEVAAFWSELGIAPSVVAEGLKQPVTVTTA

GKGIREGIVANLAAALEEAGIQVSDPKAPKAPKAGDSTAQLQVVLTDDYLQPELAAINKEALERQQPWLLVKPVGSILWLGPL

FVPGETGCWHCLAQRLRGNREVEASVLQQKRALQERNGQNKNGAVSCLPTARATLPSTLQTGLQWAATEIAKWMVKRHLNAIA

PGTARFPTLAGKIFTFNQTTLELKAHPLSRRPQCPTCGDQEILQRRGFEPLKLESRPKHFTSDGGHRATTPEQTVQKYQHLIG

PITGVVTELVRISDPANPLVHTYRAGHSFGSSAGSLRGLRNTLRYKSSGKGKTDSQSRASGLCEAIERYSGIFLGDEPRKRAT

LAELGDLAIHPEQCLHFSDRQYDNRDALNAEGSAAAYRWIPHRFAASQAIDWTPLWSLTEQKHKYVPTAICYYNYLLPPADRF

CKADSNGNAAGNSLEEAILQGFMELVERDSVALWWYNRLRRPEVELSSFEEPYFLQLQQFYRSQNRELWVLDLTADLGIPAFA

GLSRRTVGSSERVSIGFGAHLDPKIAILRALTEVSQVGLELDKVPDEKLDGESKDWMLEVTLETHPCLAPDPSQPRKTANDYP

KRWSDDIYTDVMACVEMAKVAGLETLVLDQTRPDIGLNVVKVMIPGMRTFWSRYGPGRLYDVPVQLGWLKEPLAEAEMNPTNI

PF

PatD_Q21_5GA (His tag-underlined, TEV protease site-double underlined, Linker-dotted underlined)

SEQ ID NO: 45

MS<u>HHHHHH</u>DYD<u>ENLYFQ</u>GSQLSSQLAELSEEALGDAGAGAGAGAGAGAGKLMQPTALQIKPHFHVEIIEPKQVYLLGEQGNH

ALTGQLYCQILPFLNGEYTREQIVEKLDGQVPEEYIDFVLSRLVEKGYLTEVAPELSLEVAAFWSELGIAPSVVAEGLKQPVT

VTTAGKGIREGIVANLAAALEEAGIQVSDPKAPKAPKAGDSTAQLQVVLTDDYLQPELAAINKEALERQQPWLLVKPVGSILW

LGPLFVPGETGCWHCLAQRLRGNREVEASVLQQKRALQERNGQNKNGAVSCLPTARATLPSTLQTGLQWAATEIAKWMVKRHL

NAIAPGTARFPTLAGKIFTFNQTTLELKAHPLSRRPQCPTCGDQEILQRRGFEPLKLESRPKHFTSDGGHRATTPEQTVQKYQ

HLIGPITGVVTELVRISDPANPLVHTYRAGHSFGSSAGSLRGLRNTLRYKSSGKGKTDSQSRASGLCEAIERYSGIFLGDEPR

KRATLAELGDLAIHPEQCLHFSDRQYDNRDALNAEGSAAAYRWIPHRFAASQAIDWTPLWSLTEQKHKYVPTAICYYNYLLPP

ADRFCKADSNGNAAGNSLEEAILQGFMELVERDSVALWWYNRLRRPEVELSSFEEPYFLQLQQFYRSQNRELWVLDLTADLGI

PAFAGLSRRTVGSSERVSIGFGAHLDPKIAILRALTEVSQVGLELDKVPDEKLDGESKDWMLEVTLETHPCLAPDPSQPRKTA

NDYPKRWSDDIYTDVMACVEMAKVAGLETLVLDQTRPDIGLNVVKVMIPGMRTFWSRYGPGRLYDVPVQLGWLKEPLAEAEMN

PTNIPF

PatD_Q21_7GA (His tag-underlined, TEV protease site-double underlined, Linker-dotted underlined)

TABLE 5

| | Species | Accession Number |
|---|---|---|
| 1 | *Oscillatoria nigro-viridis* | WP_015177263.1 GI:504990161 |
| 2 | *Microcystis aeruginosa* | WP_002796590.1 GI:488884365 |
| 3 | *Microcystis aeruginosa* | WP_016515303.1 GI:513846071 |
| 4 | *Oscillatoria nigro-viridis* | WP_015177263.1 GI:504990161 |
| 5 | *Microcystis aeruginosa* | WP_002796590.1 GI:488884365 |
| 6 | *Arthrospira* sp | CDM96171.1 GI:585306489 |
| 7 | *Arthrospira platensis* | WP_014276985.1 GI:504042991 |
| 8 | *Oscillatoriales* | WP_007355589.1 GI:494597335 |
| 9 | *Pleurocapsa* sp. PCC 7319 | WP_019509121.1 GI:518338914 |
| 10 | *Rivularia* sp. PCC 7116 | WP_015122225.1 GI:504935123 |
| 11 | *Cyanothece* sp. PCC 7425 | WP_012626011.1 GI:501725564 |
| 12 | *Calothrix* sp. PCC 7103 | WP_019490842.1 GI:518320635 |
| 13 | *Trichodesmium erythraeum* | WP_011611942.1 GI:499931208 |
| 14 | *Cyanothece* sp. PCC 7822 | WP_013335045.1 GI:503100251 |
| 15 | *Bradyrhizobium japonicum* | WP_028137897.1 GI:654679070 |
| 16 | *Pseudanabaena* sp. PCC 6802 | WP_019499725.1 GI:518329518 |
| 17 | *Tolypothrix bouteillei* licb1 | KGG71500.1 GI:692216992 |
| 18 | *Prochlorococcus* sp. | KGG26424.1 GI:691703159 |

TABLE 5-continued

| | Species | Accession Number | |
|---|---|---|---|
| 19 | *Corallococcus coralloides* | WP_014397424.1 GI:504210322 | |
| 20 | *Oscillatoria acuminata* | WP_015151318.1 GI:504964216 | 5 |

The invention claimed is:

1. A modified heterocyclase, wherein the N-terminus of the modified heterocyclase consists of a cyanobactin leader peptide selected from the group consisting of SEQ ID NO: 29 and SEQ ID NO: 30, and wherein the C-terminus of said modified heterocyclase comprises a YcaO-domain cyanobactin heterocyclase such that the modified heterocyclase is capable of introducing heterocyclic groups into a substrate that lacks a leader peptide.

2. The modified heterocyclase according to claim 1 wherein the YcaO-domain cyanobactin heterocyclase comprises an amino acid sequence having at least 25% sequence identity to residues 1 to 109 of SEQ ID NO: 1, residues 1 to 108 of SEQ ID NO: 2, residues 1 to 108 of SEQ ID NO: 3, residues 1 to 109 of SEQ ID NO: 4, residues 1 to 109 of SEQ ID NO: 5, SEQ ID NO: 6 or SEQ ID NO: 7.

3. The modified heterocyclase according to claim 1 wherein the YcaO-domain cyanobactin heterocyclase comprises an amino acid sequence of SEQ ID NO: 10 and/or SEQ ID NO: 12.

4. The modified heterocyclase according to claim 3 wherein the YcaO-domain cyanobactin heterocyclase comprises an amino acid sequence having at least 25% sequence identity to any one of SEQ ID NOs: 1 to 7 or a sequence of a database accession number selected from the group consisting of WP_015177263.1 GI:504990161, WP_002796590.1 GI:488884365, WP_016515303.1 GI:513846071, WP_015177263.1 GI:504990161, WP_002796590.1 GI:488884365, CDM96171.1 GI:585306489, WP_014276985.1 GI:504042991, WP_007355589.1 GI:494597335, WP_019509121.1 GI:518338914, WP_015122225.1 GI:504935123, WP_012626011.1 GI:501725564, WP_019490842.1 GI:518320635, WP_011611942.1 GI:499931208, WP_013335045.1 GI:503100251, WP_028137897.1 GI:654679070, WP_019499725.1 GI:518329518, KGG71500.1 GI:692216992, KGG26424.1 GI:691703159, WP_014397424.1 GI:504210322, and WP_015151318.1 GI:504964216.

5. The modified heterocyclase according to claim 1 wherein the cyanobactin leader sequence consists of SEQ ID NO: 29.

6. The modified heterocyclase according to claim 5 wherein the cyanobactin leader sequence consists of residues 21 to 36 of SEQ ID NOs: 18-23, residues 21 to 38 of SEQ ID NO: 24, residues 21-35 of SEQ ID NO: 25, residues 21 to 36 of SEQ ID NOs: 26 and 27 or SEQ ID NO: 28.

7. The modified heterocyclase according to claim 6 wherein the cyanobactin leader sequence consists of SEQ ID NO: 32.

8. The modified heterocyclase according to claim 1, wherein the YcaO-domain cyanobactin heterocyclase comprises an amino acid sequence having at least 25% sequence identity to residues 19 to 823 of SEQ ID NO: 39, residues 19 to 824 of SEQ ID NO: 40, residues 19 to 832 of SEQ ID NO: 41, residues 19 to 829 of SEQ ID NO: 42, residues 19 to 834 of SEQ ID NO: 43, residues 19 to 832 of SEQ ID NO: 44 or residues 19 to 836 of SEQ ID NO: 45.

9. The modified heterocyclase according to claim 7, wherein the YcaO-domain cyanobactin heterocyclase comprises the amino acid sequence of residues 19 to 823 of SEQ ID NO: 39, residues 19 to 824 of SEQ ID NO: 40, residues 19 to 832 of SEQ ID NO: 41, residues 19 to 829 of SEQ ID NO: 42, residues 19 to 834 of SEQ ID NO: 43, residues 19 to 832 of SEQ ID NO: 44 or residues 19 to 836 of SEQ ID NO: 45.

10. The modified heterocyclase according to claim 1, comprising the amino acid sequence of any one of SEQ ID NOS: 39 to 45.

11. An isolated nucleic acid encoding a modified heterocyclase according to claim 1.

12. A vector comprising an isolated nucleic acid according to claim 11 operably linked to a regulatory element.

13. A recombinant cell comprising an isolated nucleic acid according to claim 11.

14. A method of introducing heterocyclic residues into a target molecule comprising:
   treating a target molecule comprising one or more heterocyclisable residues with a modified heterocyclase according to claim 1.

15. The method according to claim 14 wherein the target molecule is a peptide or peptide analogue.

16. The method according to claim 14 wherein the target molecule lacks a cyanobactin leader sequence.

17. The method according to claim 14 wherein the modified heterocyclase converts one or more of; cysteine residues in the target molecule into thiazoline residues; selenocysteines into selenazoline residues; serine residues into oxazoline residues; threonine residues into oxazoline residues; 2,3-diaminopropanoic acid into imadazoline residues; homocysteine into 5,6-dihydro-4H-1,3-thiazine; homoserine into 5,6-dihydro-4H-1,3-oxazine; and/or 2,4-diaminobutanoic acid into 5,6-dihydro-4H-1λ2-pyrimidine.

* * * * *

UNITED STATES PATENT AND TRADEMARK OFFICE
CERTIFICATE OF CORRECTION

PATENT NO. : 10,647,977 B2  
APPLICATION NO. : 15/524219  
DATED : May 12, 2020  
INVENTOR(S) : James Naismith Page 1 of 1

It is certified that error appears in the above-identified patent and that said Letters Patent is hereby corrected as shown below:

On the Title Page

The Assignee name "THE UNIVERSITY COURT OF THE UNIVERSITY OF ABERDEEN, Aberdeen (GB); THE UNIVERSITY COURT OF THE UNIVERSITY OF ST. ANDREWS, St. Andrews, Fife (GB)" should read -- OXFORD UNIVERSITY INNOVATION LIMITED, Oxford (GB) --.

Signed and Sealed this  
First Day of September, 2020

Andrei Iancu  
*Director of the United States Patent and Trademark Office*